(12) United States Patent
Ran et al.

(10) Patent No.: US 11,939,341 B2
(45) Date of Patent: Mar. 26, 2024

(54) ORGANIC COMPOUND, ELECTROLUMINESCENT MATERIAL, AND APPLICATION THEREOF

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Quan Ran, Shanghai (CN); Wei Gao, Shanghai (CN); Lei Zhang, Shanghai (CN); Wenpeng Dai, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

(*) Notice: Subject to any disclaimer, the term of this patent is extended or adjusted under 35 U.S.C. 154(b) by 547 days.

(21) Appl. No.: 17/161,692

(22) Filed: Jan. 29, 2021

(65) Prior Publication Data
US 2021/0147442 A1 May 20, 2021

(30) Foreign Application Priority Data
Oct. 30, 2020 (CN) .......................... 202011198042.2

(51) Int. Cl.
*C07D 495/20* (2006.01)
*C07D 471/04* (2006.01)
(Continued)

(52) U.S. Cl.
CPC ......... *C07D 495/20* (2013.01); *C07D 471/04* (2013.01); *C07D 471/20* (2013.01);
(Continued)

(58) Field of Classification Search
None
See application file for complete search history.

(56) References Cited

U.S. PATENT DOCUMENTS

2019/0348609 A1* 11/2019 Yen .................... H10K 85/6572

FOREIGN PATENT DOCUMENTS

| CN | 105924450 A | 9/2016 |
|---|---|---|
| CN | 107253950 A | 10/2017 |

(Continued)

*Primary Examiner* — Jay Yang
(74) *Attorney, Agent, or Firm* — KILPATRICK TOWNSEND & STOCKTON LLP

(57) ABSTRACT

Provided are an organic compound, an electroluminescent material and an application thereof. The organic compound has a structure represented by Formula I. With the design of the spiro parent structure and the introduction of specific substituents, the organic compound can prevent materials from stacking and reduce the crystallinity of the molecule. The design of the spiro structure and substituents make the organic material have a high triplet state energy level Ti, and the nitrogen heterocycle and its linking groups make the organic compound have characteristics of good electron and hole transport performances. The organic compound has suitable HOMO and LUMO energy levels, facilitating the coordination of adjacent layers in terms of energy level. The organic compound also has advantages of high glass-transition temperature and good molecular thermal stability. Therefore, the organic compound can effectively improve the light emitting efficiency and lifetime of the device.

17 Claims, 1 Drawing Sheet

(51) Int. Cl.
    *C07D 471/20*     (2006.01)
    *C07D 471/22*     (2006.01)
    *C07D 493/20*     (2006.01)
    *C07D 493/22*     (2006.01)
    *C07D 495/22*     (2006.01)
    *C07D 519/00*     (2006.01)
    *H01L 51/00*     (2006.01)
    *H10K 85/60*     (2023.01)
    *H10K 50/18*     (2023.01)

(52) U.S. Cl.
    CPC ......... *C07D 471/22* (2013.01); *C07D 493/20* (2013.01); *C07D 493/22* (2013.01); *C07D 495/22* (2013.01); *C07D 519/00* (2013.01); *H10K 85/633* (2023.02); *H10K 85/653* (2023.02); *H10K 85/654* (2023.02); *H10K 85/656* (2023.02); *H10K 85/6572* (2023.02); *H10K 85/6574* (2023.02); *H10K 85/6576* (2023.02); *H10K 50/18* (2023.02)

(56) References Cited

FOREIGN PATENT DOCUMENTS

| | | |
|---|---|---|
| CN | 109694378 A | 4/2019 |
| CN | 110759939 A | 2/2020 |
| KR | 101321988 B1 | 10/2013 |

\* cited by examiner

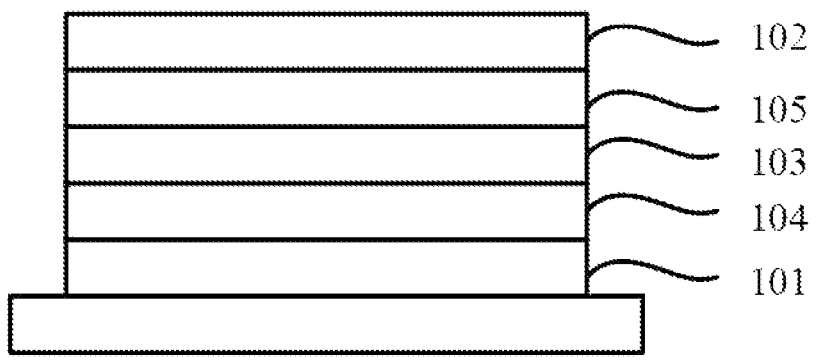

ORGANIC COMPOUND, ELECTROLUMINESCENT MATERIAL, AND APPLICATION THEREOF

CROSS-REFERENCE TO RELATED APPLICATIONS

The application claims the benefit of the earlier filing date of Chinese Patent Application No. 202011198042.2, filed on Oct. 30, 2020 to the State Intellectual Property Office, the contents of which are incorporated by reference herein in its entirety.

FIELD

The present disclosure belongs to the field of organic electroluminescent materials, and specifically, relates to an organic compound, an electroluminescent material, and an application thereof.

BACKGROUND

Organic Light Emitting Diode (OLED) is a new generation of display technology that has developed rapidly in recent years. It has been widely used in flat panel display, flexible display, solid-state lighting, automotive display and other industries due to its own various advantages such as ultra-thinness, self-illumination, wide viewing angle, fast response, high light emitting efficiency, good temperature adaptability, simple production process, low driving voltage, low energy consumption, and flexibility.

In OLED devices, the choice of material is crucial, as the structure and properties of the material directly affect the final performance of the device. According to the light emitting mechanism, organic electroluminescent materials can be divided into electrofluorescent materials and electrophosphorescent materials, where the principle of electrofluorescent materials is the radiative decay and transition of singlet excitons while the principle of the electrophosphorescent materials is light emitted during the process of the radiative decay of triplet excitons to the ground state. According to the spin quantum statistics theory, since the probability of the formation of singlet excitons and triplet excitons is 1:3, the internal quantum efficiency of electrofluorescent materials does not exceed 25% and their external quantum efficiency is generally less than 5%, while the internal quantum efficiency of electrophosphorescent materials can theoretically reach 100% and their external quantum efficiency can reach 20%. In 1998, Pro. Ma Yuguang, Jilin University and Prof. Forrest, Princeton University, USA, had reported the discoveries of doping osmium complex and platinum complex as dyes into the light emitting layer, respectively. They, for the first time, successfully produced and explained the phenomenon of phosphorescent electroluminescence, and had pioneered the application of the prepared phosphorescent materials to organic light emitting devices.

Due to the long lifetime of phosphorescent heavy metal material, which can reach the level of μs, under the high current density, the heavy metal phosphorescent material may cause triplet-triplet annihilation and concentration quenching, resulting in device performance degradation. Therefore, the heavy metal phosphorescent material is usually doped into a suitable host material to form a host-guest doping system to optimize energy transfer and maximize light emitting efficiency and lifetime. In the current research, the heavy metal doping material has been commercially matured, and it is difficult to develop alternative doping materials. Therefore, it is a common idea among researchers to focus on the development of phosphorescent host materials.

4,4'-bis(N-carbazole)biphenyl (CBP),

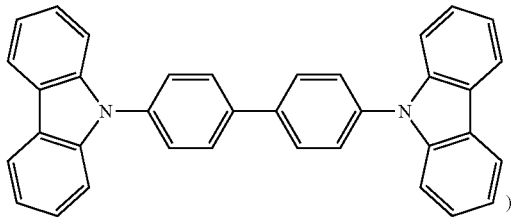 [SMILES: c1ccc2c(c1)c1ccccc1n2-c1ccc(-c2ccc(-n3c4ccccc4c4ccccc43)cc2)cc1]

)

has good hole transport performance, and is one of the most widely used phosphorescent host materials. However, the glass transition temperature of CBP is low, and its thermal stability is poor, which affects the lifetime of the device. Moreover, the transport of electrons and holes of CBP is unbalanced, the light emitting region is not ideal, and the efficiency roll-off phenomenon of the device is serious, so that the efficiency of energy transfer from the host material to the guest material is low, reducing the efficiency of the device.

There is currently a lot of research work devoted to the development of new phosphorescent host materials. For example, CN104073246A discloses an organic electrophosphorescent host material as well as a preparation method thereof and an organic electroluminescent device. The structure of the organic electrophosphorescent host material includes an indenofluorenyl group and a pyrido-indole group linked by a single bond, and thus the organic electrophosphorescent host material has good solubility, film formation and stability as well as high electron transport performance, facilitating the charge balance of carriers in the recombination region and improving the light emitting efficiency of the device. CN103012481A discloses a phosphorescent host material and a preparation method and an application thereof. The phosphorescent host material is composed of carbazole with a hole transport capability and a unit of diphenylphosphine oxide and benzothiazole/benzoxazole with an electron transport capability, has good thermal stability and hole transport and electron transport properties, and can be used as red and green phosphorescent host materials. However, in the current research of phosphorescent host materials, there are still problems such as high turn-on voltage, high energy consumption, poor light emitting efficiency and low working life, and the phosphorescent host materials cannot meet the comprehensive performance requirements of energy consumption, efficiency, the ability to process and lifetime.

Therefore, it is a research focus in the art to develop more kinds of phosphorescent host materials with better comprehensive performance to meet the usage requirements of high-performance OLED devices.

SUMMARY

To develop more kinds of phosphorescent host materials with better performances, a first object of the present disclosure is to provide an organic compound having a structure represented by Formula I:

Formula I

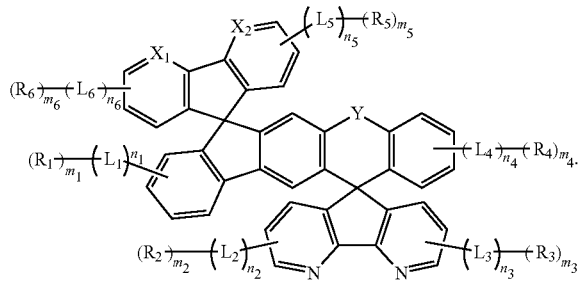

In Formula I, $X_1$ and $X_2$ are each independently selected from C or N.

In Formula I, Y is any one selected from the group consisting of O, S, N—$R_{N1}$, $CR_{C1}R_{C2}$, O=S=O, $SiR_{S1}R_{S2}$, O=P—$Ar_1$, and S=P—$Ar_2$.

$R_{N1}$, $R_{C1}$, $R_{C2}$, $R_{S1}$, and $R_{S2}$ are each independently any one selected from the group consisting of substituted or unsubstituted C1 to C20 straight or branched chain alkyl, substituted or unsubstituted C6 to C40 aryl, and substituted or unsubstituted C3 to C40 heteroaryl.

$Ar_1$ and $Ar_2$ are each independently any one selected from the group consisting of substituted or unsubstituted C6 to C40 aryl and substituted or unsubstituted C3 to C40 heteroaryl.

In Formula I, $L_1$, $L_2$, $L_3$, $L_4$, $L_5$, and $L_6$ are each independently any one selected from the group consisting of a single bond, substituted or unsubstituted C6 to C40 arylene, and substituted or unsubstituted C3 to C40 heteroarylene, where "$L_1$ is a single bond" means that $R_1$ is directly linked to a benzene ring, and similarly, when $L_2$, $L_3$, $L_4$, $L_5$, and $L_6$ are single bonds, $R_2$, $R_3$, $R_4$, $R_5$, and $R_6$ are linked to a six-membered aromatic ring.

In Formula I, $R_1$, $R_2$, $R_3$, $R_4$, $R_5$, and $R_6$ are each independently any one selected from the group consisting of deuterium, halogen, cyano, substituted or unsubstituted C1 to C20 straight or branched chain alkyl, substituted or unsubstituted C1 to C20 alkoxy, substituted or unsubstituted C1 to C20 alkylthio, substituted or unsubstituted C3 to C20 cycloalkyl, substituted or unsubstituted C6 to C40 aryl, substituted or unsubstituted C6 to C40 arylamine, substituted or unsubstituted C3 to C40 heteroaryl, and substituted or unsubstituted C2 to C40 nonaromatic heterocyclyl.

In Formula I, $n_1$, $n_4$, $n_5$, $n_6$, $m_1$, $m_4$, $m_5$, and $m_6$ are each independently an integer of 0-4, for example, 0, 1, 2, 3, or 4.

In Formula I, $n_2$, $n_3$, $m_2$, and $m_3$ are each independently an integer of 0-3, for example, 0, 1, 2, or 3.

In the present disclosure, C1 to C20 may each independently be C2, C3, C4, C5, C6, C8, C10, C12, C14, C16, C18, or C19, etc.

C6 to C40 may each independently be C6, C8, C10, C12, C13, C14, C15, C16, C18, C20, C22, C24, C26, C28, C30, C32, C34, C36, or C38, etc.

C3 to C40 may each independently be C4, C5, C6, C8, C10, C12, C13, C14, C15, C16, C18, C20, C22, C24, C26, C28, C30, C32, C34, C36, or C38, etc.

C3 to C20 may each independently be C4, C5, C6, C8, C10, C11, C13, C15, C17, C19, or C20, etc.

C2 to C40 may each independently be C3, C4, C5, C6, C8, C10, C12, C13, C14, C15, C16, C18, C20, C22, C24, C26, C28, C30, C32, C34, C36, or C38, etc.

In the present disclosure, the halogen includes fluorine, chlorine, bromine, or iodine. The same expressions hereinafter have the same meaning.

For the organic compound provided by the present disclosure, with the coordination of a spiro-parent nucleus structure in the molecular structure with substituents, the organic compound has a higher triplet energy level $E_T$, and thus can prevent the triplet energy backflow from the guest to the host, confine the triplet excitons to the light emitting layer as much as possible and improve the light emitting efficiency. At the same time, HOMO and LUMO energy levels of the organic compound can match the energy level of a material of an adjacent layer, to reduce hole and electron injection barriers and reduce a driving voltage of the device. Moreover, the energy gap $E_g$ between HOMO and LUMO of the organic compound is greater than the energy gap of the guest material, which facilitates the energy transfer from the host to the guest and the direct capture of carriers on the phosphorescent guest. The organic compound provided by the present disclosure also has a higher carrier transport rate and balanced carrier transport performance, facilitating the transport balance of holes and electrons in the device, obtaining a wider carrier recombination region, and improving the light emitting efficiency. The organic compound also has a suitable molecular weight and higher glass transition temperature $T_g$, and shows good thermal stability and film formability, so that the compound material as the phosphorescent host material forms a stable and uniform thin film in the process of vacuum thermal evaporation, reduces phase separation, and maintains device stability.

A second object of the present disclosure is to provide an electroluminescent material including the organic compound as described in the first object.

A third object of the present disclosure is to provide a display panel including an OLED device. The OLED device includes an anode, a cathode, and an organic thin film layer between the anode and the cathode, and a material of the organic thin film layer includes the electroluminescent material as described in the second object.

A fourth object of the present disclosure is to provide an electronic device including the display panel as described in the third object.

Compared with the related art, the present disclosure has beneficial effects described below.

The organic compound provided by the present disclosure is an organic small-molecule compound containing a spiro structure which can prevent materials from stacking, facilitating the reduction of the crystallinity of molecules and improvement of the light emitting performance and stability of materials. With the design of the spiro parent structure and the introduction of specific substituents, the organic compound has a high triplet energy level Ti and great electron and hole transport performance, enabling efficient energy transfer to the guest and efficiently improving the charge balance of carriers in the recombination region. The organic compound has suitable HOMO and LUMO energy levels, facilitating the coordination of adjacent layers in terms of energy level. The organic compound also has high glass-transition temperature and good molecular thermal stability. Therefore, the organic compound can effectively improve the light emitting efficiency and lifetime of the device. The organic compound, as the electroluminescent material, can be applied to the light emitting layer, electron blocking layer or hole blocking layer of the OLED device, especially suitable for the application to the light emitting layer as the phosphorescent host material, significantly improving the light emitting efficiency of the device, reducing the turn-on voltage and energy consumption of the device, and prolonging the working life of the device.

BRIEF DESCRIPTION OF DRAWINGS

The FIGURE is a structural view of an OLED device provided by the present disclosure, where 101 denotes an anode, 102 denotes a cathode, 103 denotes a light emitting layer, 104 denotes a first organic thin film layer, and 105 denotes a second organic thin film layer.

DETAILED DESCRIPTION

The embodiments of the present disclosure are further described below through specific embodiments. The examples described herein are used for a better understanding of the present disclosure and should not be construed as specific limitations to the present disclosure.

A first object of the present disclosure is to provide an organic compound, where the organic compound has a structure represented by Formula I:

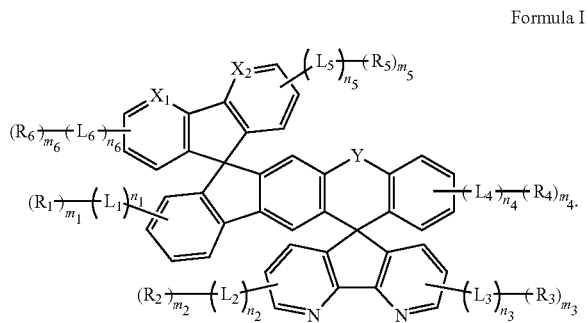

Formula I

In Formula I, $X_1$ and $X_2$ are each independently selected from C or N.

In Formula I, Y is any one selected from the group consisting of O, S, N—$R_{N1}$, $CR_{C1}R_{C2}$, O=S=O, $SiR_{S1}R_{S2}$, O=P—$Ar_1$, and S=P—$Ar_2$.

$R_{N1}$, $R_{C1}$, $R_{C2}$, $R_{S1}$, and $R_{S2}$ are each independently any one selected from the group consisting of substituted or unsubstituted C1 to C20 straight or branched chain alkyl, substituted or unsubstituted C6 to C40 aryl, and substituted or unsubstituted C3 to C40 heteroaryl.

$Ar_1$ and $Ar_2$ are each independently any one selected from the group consisting of substituted or unsubstituted C6 to C40 aryl and substituted or unsubstituted C3 to C40 heteroaryl.

In Formula I, $L_1$, $L_2$, $L_3$, $L_4$, $L_5$, and $L_6$ are each independently any one selected from the group consisting of a single bond, substituted or unsubstituted C6 to C40 arylene, and substituted or unsubstituted C3 to C40 heteroarylene, where "$L_1$ is a single bond" means that $R_1$ is directly linked to a benzene ring, and similarly, when $L_2$, $L_3$, $L_4$, $L_5$, and $L_6$ are single bonds, $R_2$, $R_3$, $R_4$, $R_5$, and $R_6$ are linked to a six membered aromatic ring.

In Formula I, $R_1$, $R_2$, $R_3$, $R_4$, $R_5$, and $R_6$ are each independently any one selected from the group consisting of deuterium, halogen, cyano, substituted or unsubstituted C1 to C20 straight or branched chain alkyl, substituted or unsubstituted C1 to C20 alkoxy, substituted or unsubstituted C1 to C20 alkylthio, substituted or unsubstituted C3 to C20 cycloalkyl, substituted or unsubstituted C6 to C40 aryl, substituted or unsubstituted C6 to C40 arylamine, substituted or unsubstituted C3 to C40 heteroaryl, and substituted or unsubstituted C2 to C40 nonaromatic heterocyclyl.

In Formula I, $n_1$, $n_4$, $n_5$, $n_6$, $m_1$, $m_4$, $m_5$, and $m_6$ are each independently an integer of 0-4, for example, 0, 1, 2, 3, or 4.

In Formula I, $n_2$, $n_3$, $m_2$, and $m_3$ are each independently an integer of 0-3, for example, 0, 1, 2, or 3.

In the present disclosure, C1 to C20 may each independently be C2, C3, C4, C5, C6, C8, C10, C12, C14, C16, C18, or C19, etc.

C6 to C40 may each independently be C6, C8, C10, C12, C13, C14, C15, C16, C18, C20, C22, C24, C26, C28, C30, C32, C34, C36, or C38, etc.

C3 to C40 may each independently be C4, C5, C6, C8, C10, C12, C13, C14, C15, C16, C18, C20, C22, C24, C26, C28, C30, C32, C34, C36, or C38, etc.

C3 to C20 may each independently be C4, C5, C6, C8, C10, C11, C13, C15, C17, C19, or C20, etc.

C2 to C40 may each independently be C3, C4, C5, C6, C8, C10, C12, C13, C14, C15, C16, C18, C20, C22, C24, C26, C28, C30, C32, C34, C36, or C38, etc.

In the present disclosure, the halogen includes fluorine, chlorine, bromine, or iodine. The same expressions hereinafter have the same meaning.

The organic compound provided by the present disclosure has the structure represented by Formula I. The central backbone of the structure has a spiro structure, and the six-membered ring of the spiro structure is connected to linking groups $L_1$ to $L_6$ and specific substituents $R_1$ to $R_6$. The introduction of azafluorene to the spiro ring enables the organic compound to have good electron transport performance, and the connections of specific substituents $R_1$ to $R_6$ ensure the hole transport performance. With the design of the backbone structure and the connections of specific substituents, the organic compound has both good electron and hole transport performances, efficiently improving the charge balance of carriers in the recombination region. The spiro structure in the backbone reduces the intermolecular force, avoids stacking of materials, and reduces the crystallinity of the material, facilitating the usage for mass production. Meanwhile, the spiro structure also helps improve the triplet energy level of the molecule, can efficiently transfer energy to the guest, and confine more excitons of the light emitting layer to the light emitting layer to improve the utilization rate of excitons, increasing the light emitting efficiency.

The organic compound has a high triplet energy level En which can reach 2.61 to 2.86 eV. Therefore, the organic compound is suitable for the application to the light emitting layer of the OLED device as the phosphorescent host material, especially as the blue phosphorescent host material, and thus can ensure the effective energy transfer to the guest and prevent the energy backflow. The organic compound has good thermal stability and a high glass transition temperature due to its special structure and thus becomes more stable in the preparation of the device, facilitating the lifetime of the device.

In an embodiment, the substituents in the substituted straight or branched chain alkyl, substituted aryl, substituted heteroaryl, substituted arylene, substituted heteroarylene, substituted alkoxy, substituted alkylthio, substituted cycloalkyl, substituted arylamine, and substituted nonaromatic heterocyclyl are each independently at least one selected from the group consisting of deuterium, halogen, cyano, C1 to C10 (e.g., C2, C3, C4, C5, C6, C7, C8, or C9) straight or branched chain alkyl, C1 to C10 (e.g., C2, C3, C4, C5, C6, C7, C8, or C9) alkoxy, C1 to C10 (e.g., C2, C3, C4, C5, C6, C7, C8, or C9) alkylthio, C6 to C20 (e.g., C6, C9, C10, C12, C14, C16, or C18) aryl, C2 to C20 (e.g., C3, C4, C5, C6, C8, C10, C12, C14, C16 or C18) heteroaryl, and C6 to C18 (e.g., C6, C9, C10, C12, C14, C16 or C18) arylamine.

In an embodiment, Y is selected from the group consisting of O, S, N—$R_{N1}$, and $CR_{C1}R_{C2}$.

In an embodiment, $R_{N1}$, $R_{C1}$, and $R_{C2}$ are each independently any one selected from the group consisting of unsubstituted or $R_{y1}$-substituted C1 to C6 straight or branched chain alkyl, unsubstituted or $R_{y}i$-substituted C6 to C18 aryl, and unsubstituted or $R_{y}i$-substituted C3 to C12 heteroaryl.

The C1 to C6 straight or branched chain alkyl may be C1, C2, C3, C4, C5, or C6 straight or branched chain alkyl, exemplarily including but not limited to methyl, ethyl, n-propyl, isopropyl, n-butyl, tert-butyl, isobutyl, n-pentyl, or n-hexyl.

The C6 to C18 aryl may be C6, C9, C10, C12, C14, C16, or C18 aryl, exemplarily including but not limited to phenyl, biphenylyl, naphthyl, anthryl, phenanthryl, or fluorenyl.

The C3 to C12 heteroaryl may be C3, C4, C5, C6, C9, C10 or C12 heteroaryl, exemplarily including but not limited to pyrrolyl, pyridyl, pyrimidinyl, pyrazinyl, quinolyl, isoquinolyl, furanyl, thienyl, indolyl, or carbazolyl.

$R_{y1}$ is each independently any one selected from the group consisting of deuterium, halogen, cyano, C1 to C6 (e.g., C2, C3, C4, or C5) straight or branched chain alkyl, C1 to C6 (e.g., C2, C3, C4, or C5) alkoxy, C1 to C6 (e.g., C2, C3, C4, or C5) alkylthio, C6 to C12 (e.g., C6, C9, C10, or C12) aryl, C2 to C12 (e.g., C3, C4, C5, C6, C9, C10, or C12) heteroaryl, or C6 to C18 (e.g., C6, C9, C10, C12, C14, C16, or C18) arylamine.

In an embodiment, $L_1$, $L_2$, $L_3$, $L_4$, $L_5$, and $L_6$ are each independently any one selected from the group consisting of a single bond, phenylene

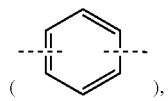

biphenylene

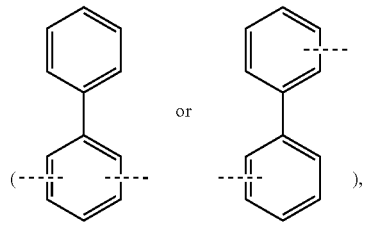

terphenylene

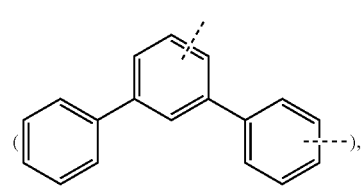

naphthylene

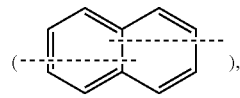

and C3 to C12 nitrogen-containing heteroarylene.

The C3 to C12 nitrogen-containing heteroarylene may be C3, C4, C5, C6, C8, C10, or C12 nitrogen-containing heteroarylene, exemplarily including but not limited to pyrrolylene, pyridylene, imidazolylidene, indolylene, carbazolylidene, quinolinylene, or isoquinolinylene.

In an embodiment, $R_1$, $R_4$, $R_5$, and $R_6$ are each independently any one selected from the group consisting of deuterium, unsubstituted or $R_{y2}$-substituted C1 to C6 (e.g., C2, C3, C4, or C5) straight or branched chain alkyl, unsubstituted or $R_{y2}$-substituted C6 to C18 (e.g., C6, C9, C10, C12, C14, C16, or C18) aryl, unsubstituted or $R_{y2}$-substituted C3 to C18 (e.g., C3, C4, C5, C6, C9, C10, or C12) heteroaryl, unsubstituted or $R_{y2}$-substituted diphenylamino, C1 to C6 (e.g., C2, C3, C4, or C5) alkoxy, and C1 to C6 (e.g., C2, C3, C4, or C5) alkylthio.

$R_{y2}$ is each independently any one selected from the group consisting of deuterium, halogen, cyano, C1 to C6 (e.g., C2, C3, C4, or C5) straight or branched chain alkyl, C1 to C6 (e.g., C2, C3, C4, or C5) alkoxy, C1 to C6 (e.g., C2, C3, C4, or C5) alkylthio, C6 to C12 (e.g., C6, C9, C10, or C12) aryl, C2 to C12 (e.g., C3, C4, C5, C6, C9, C10, or C12) heteroaryl, and C6 to C18 (e.g., C6, C9, C10, C12, C14, C16, or C18) arylamine.

In an embodiment, at least one of $R_1$, $R_2$, $R_3$, $R_4$, $R_5$, or $R_6$ is an electron-donating group, and in a preferred embodiment, at least one of $R_2$ or $R_3$ is the electron-donating group.

In the present disclosure, the "electron-donating group" refers to a group capable of improving an electron cloud density on a benzene ring, exemplarily including but not limited to, carbazolyl, arylamine, N-phenylcarbazolyl, phenothiazinyl, phenoxazinyl, acridinyl, hydroacridinyl, N-phenylphenothiazinyl, N-phenylphenoxazinyl, N-phenylhydroacridinyl, dibenzofuranyl, dibenzothienyl, azocarbazolyl, or a carbazolyl-containing condensed group.

In an embodiment, $R_2$ and $R_3$ are each independently any one selected from the group consisting of the following groups:

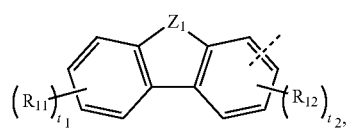

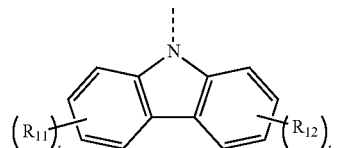

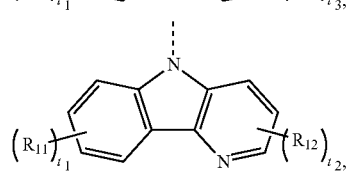

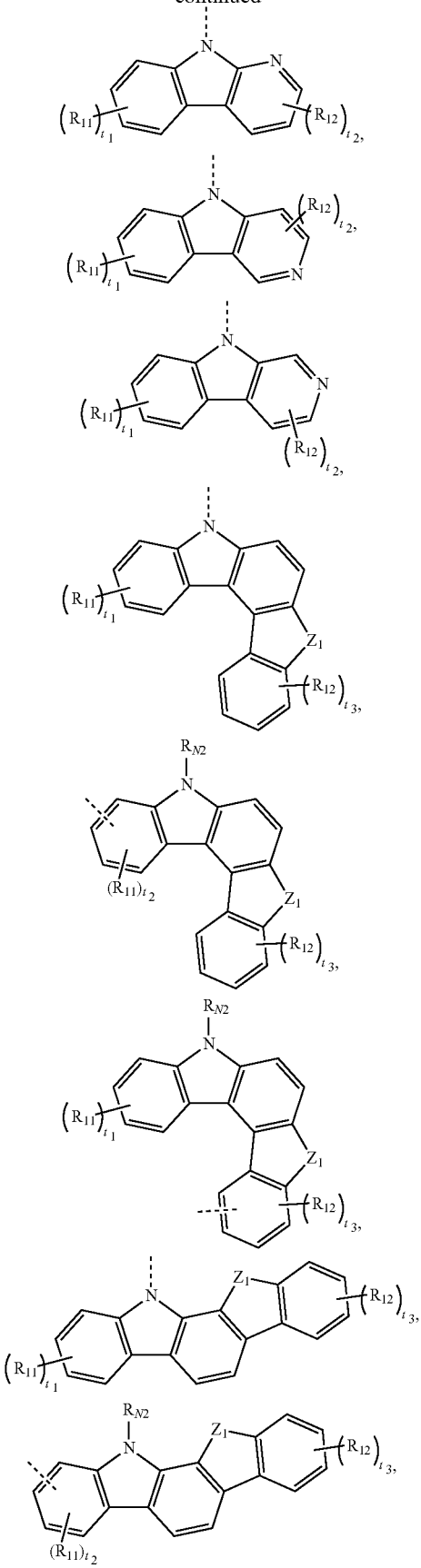
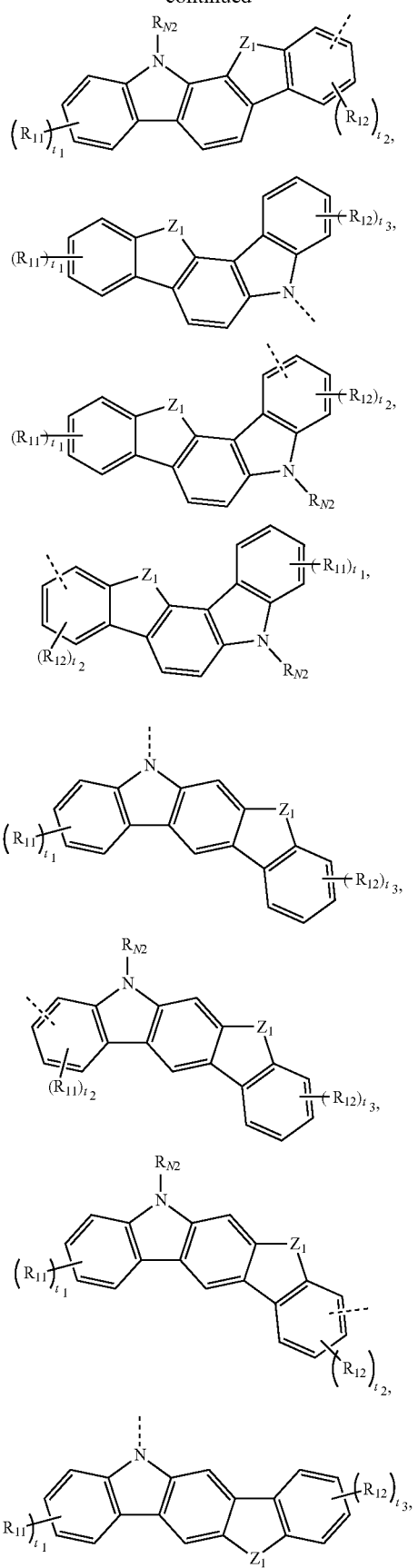

-continued

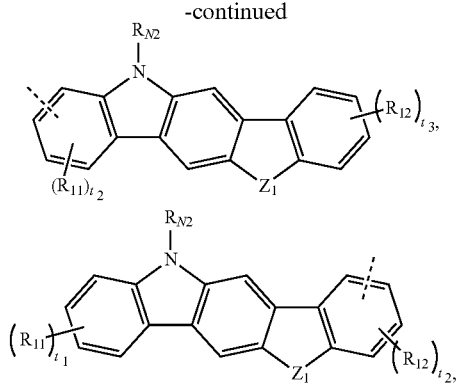

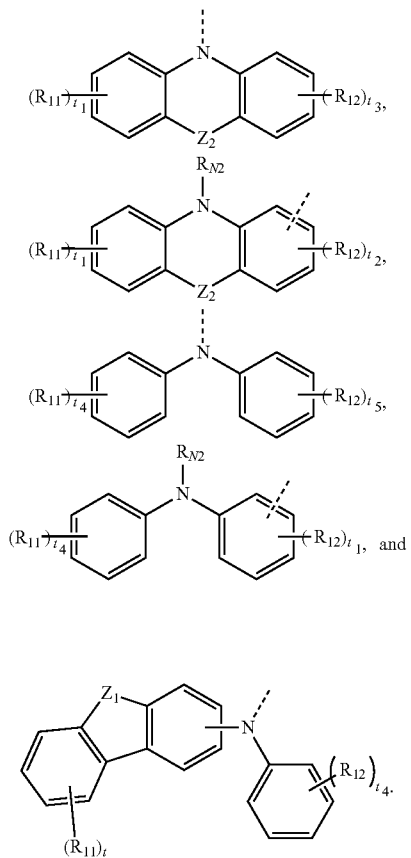

In the above groups, the dashed line represents a linkage site of the group.

$Z_1$ and $Z_2$ are each independently any one selected from the group consisting of O, S, N—$R_{N3}$, $CR_{C3}R_{C4}$, and $SiR_{S3}R_{S4}$.

$R_{N2}$, $R_{N3}$, $R_{C3}$, $R_{C4}$, $R_{S3}$, and $R_{S4}$ are each independently any one selected from the group consisting of hydrogen, deuterium, unsubstituted or $R_{y3}$-substituted C1 to C20 (e.g., C2, C3, C4, C5, C6, C8, C10, C12, C14, C16, C18, or C19) straight or branched chain alkyl, unsubstituted or $R_{y3}$-substituted C6 to C20 (e.g., C6, C8, C10, C12, C13, C14, C15, C16, or C18) aryl, and unsubstituted or $R_{y3}$-substituted C3 to C20 (e.g., C4, C5, C6, C8, C10, C12, C13, C14, C15, C16, or C18) heteroaryl; and $R_{C3}$ and $R_{C4}$ are not joined or joined to form a ring through chemical bond(s).

$R_{11}$, $R_{12}$, and $R_{y3}$ are each independently any one selected from the group consisting of deuterium, halogen, cyano, C1 to C10 (e.g., C2, C3, C4, C5, C6, C7, C8, or C9) straight or branched chain alkyl, C1 to C10 (e.g., C2, C3, C4, C5, C6, C7, C8, or C9) alkoxy, C1 to C10 (e.g., C2, C3, C4, C5, C6, C7, C8, or C9) alkylthio, C6 to C12 (e.g., C6, C9, C10, C12, C14, C16, or C18) aryl, C2 to C20 (e.g., C3, C4, C5, C6, C8, C10, C12, C14, C16, or C18) heteroaryl, and C6 to C18 (e.g., C6, C9, C10, C12, C14, C16, or C18) arylamine.

$t_1$ and $t_3$ are each independently an integer of 0-4, for example, 0, 1, 2, 3, or 4. $t_4$ and $t_5$ are each independently an integer of 0-5, for example, 0, 1, 2, 3, 4, or 5.

In an embodiment, $R_2$ and $R_3$ are each independently any one selected from the group consisting of the following groups and the following groups substituted with substituent(s):

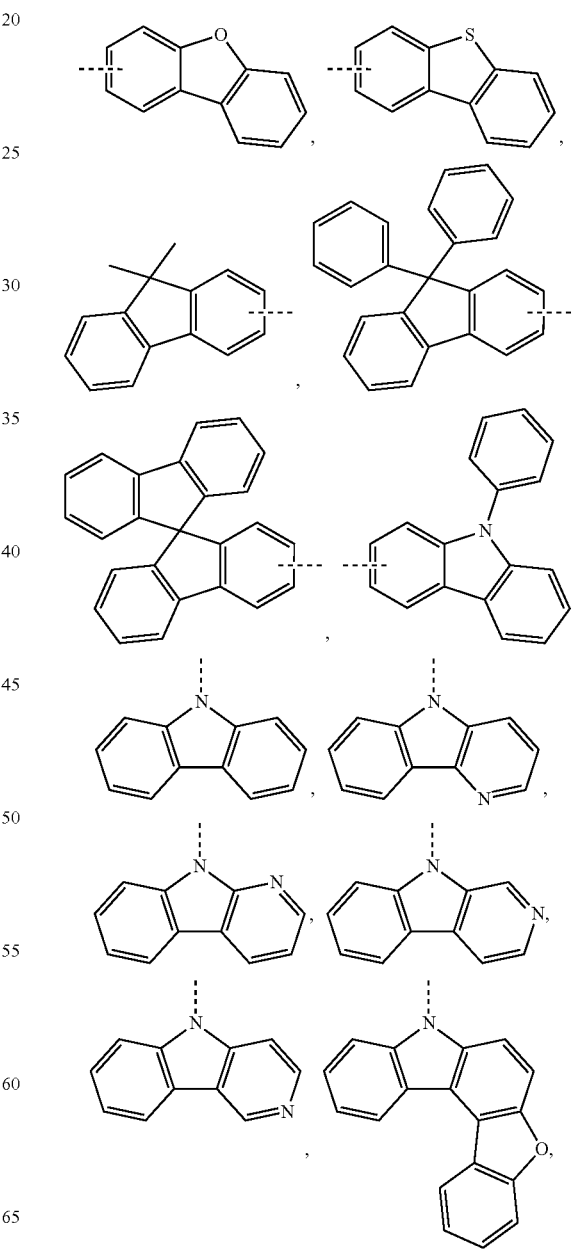

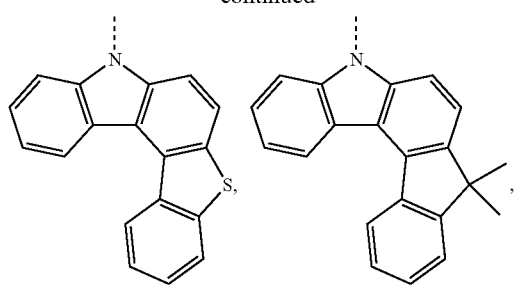
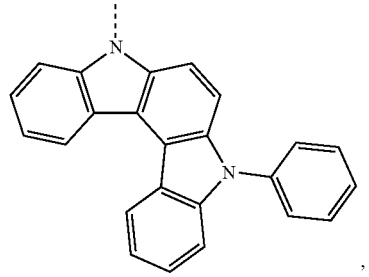
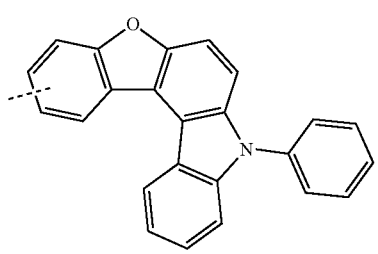
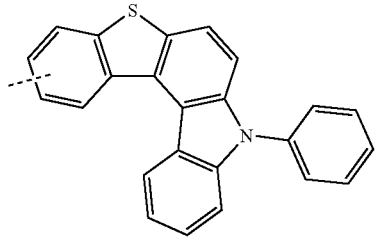
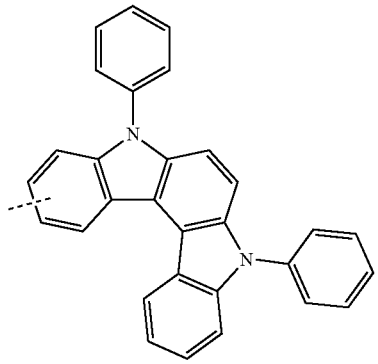
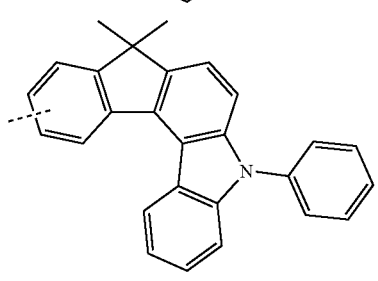
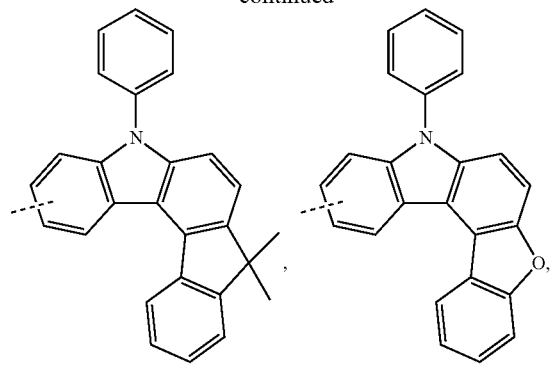
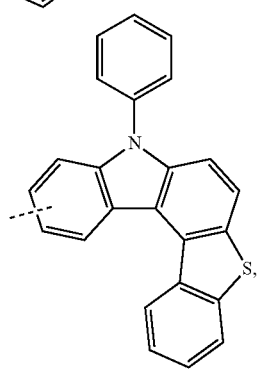
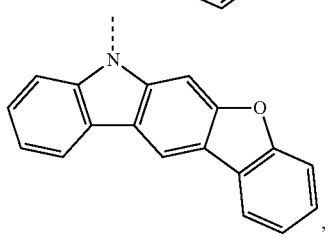
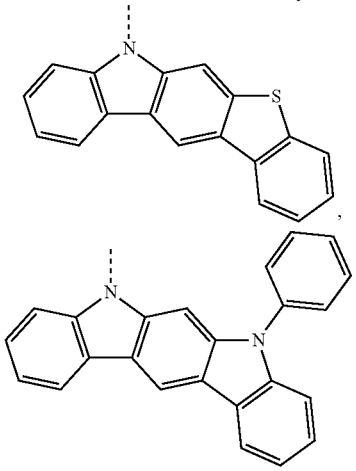
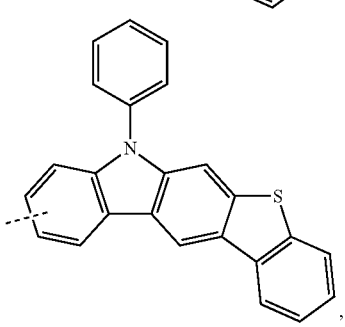

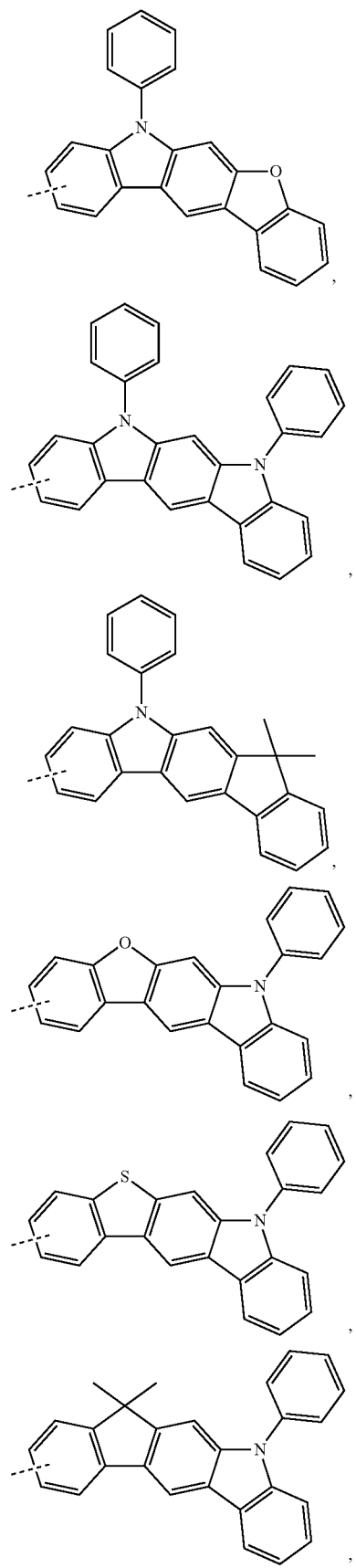
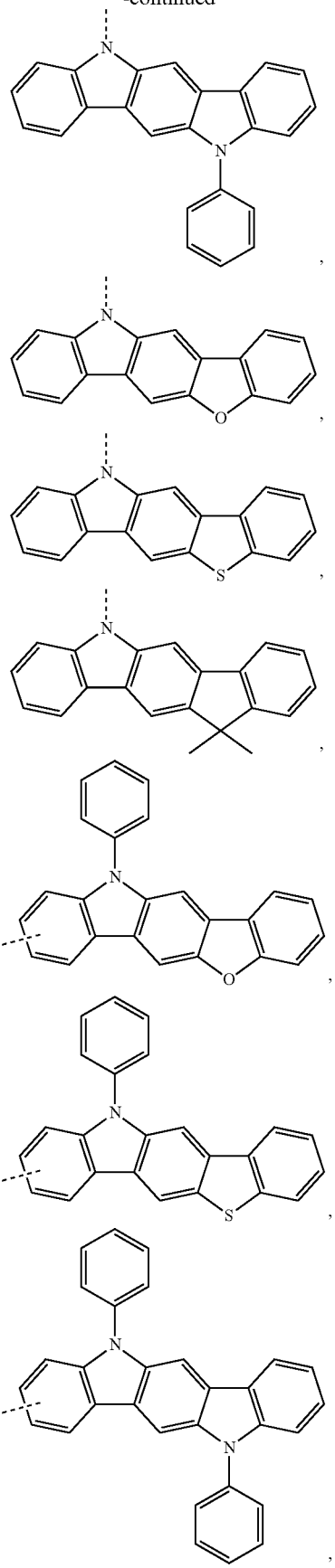

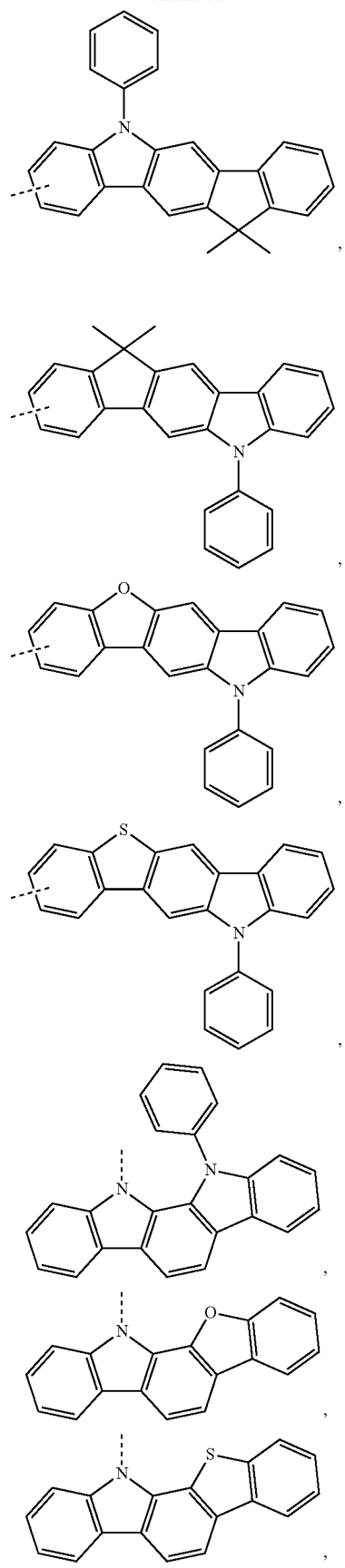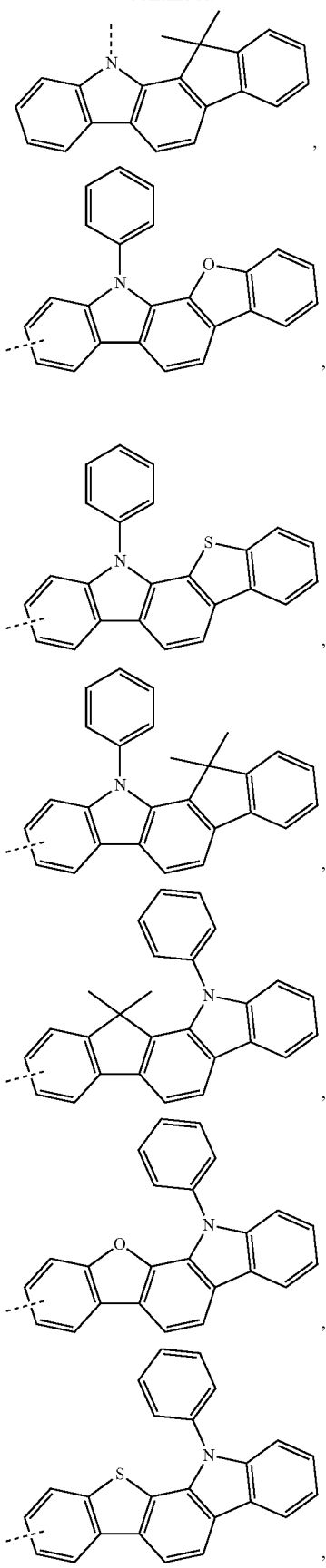

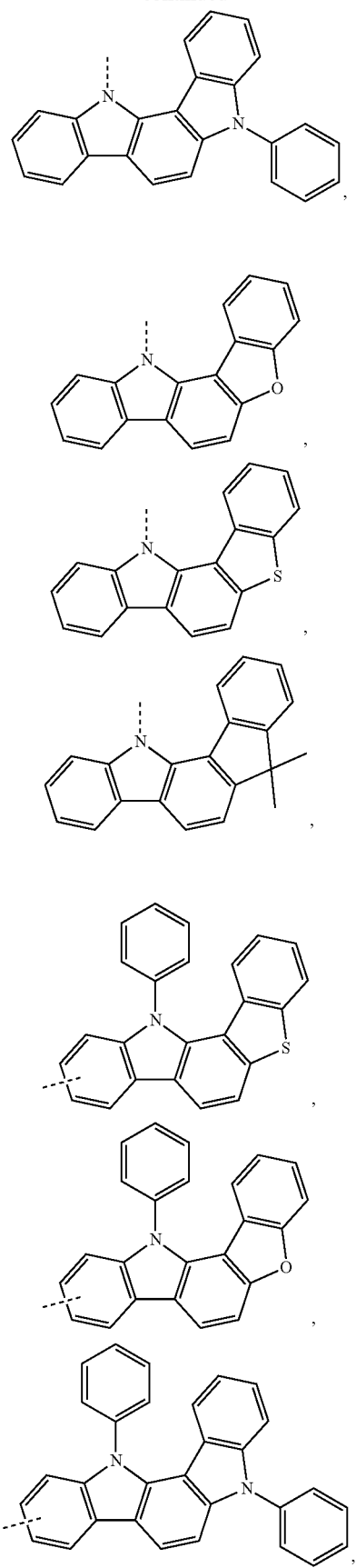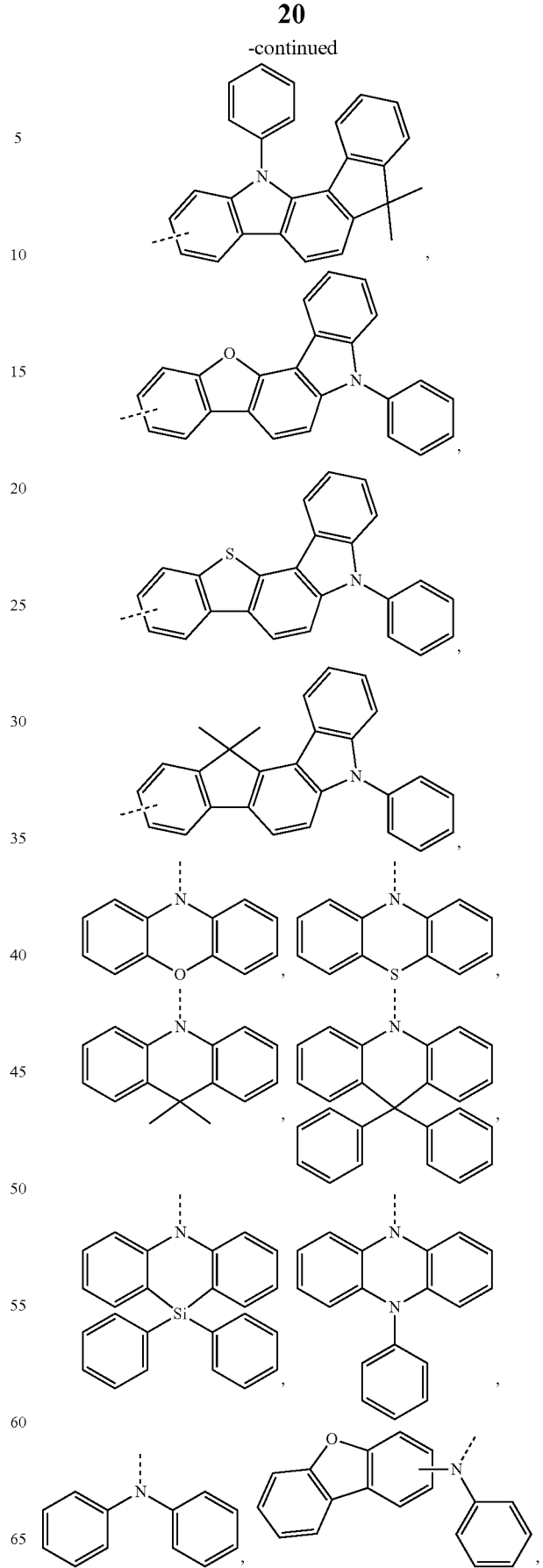

21
-continued

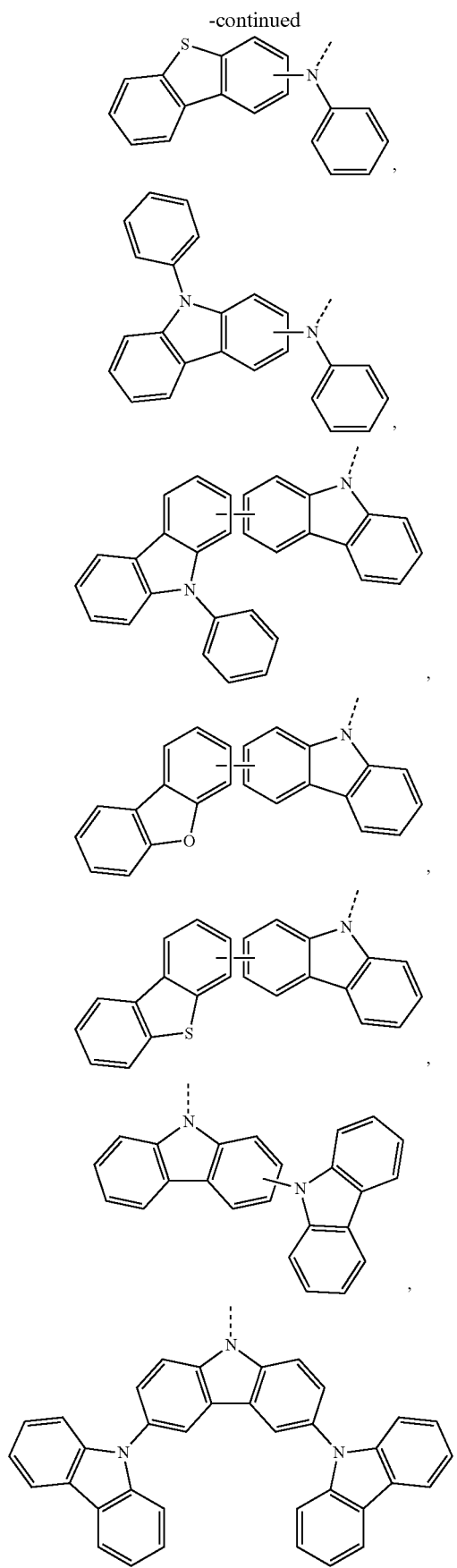

, and

22
-continued

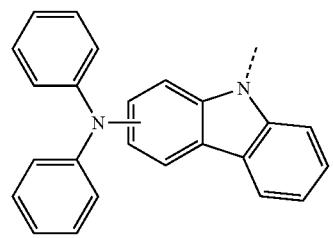

.

In the above groups, the dashed line represents a linkage site of the group.

The substituent(s) is(are) each independently at least one selected from the group consisting of deuterium, C1 to C10 (e.g., C2, C3, C4, C5, C6, C7, C8, or C9) straight or branched chain alkyl, C1 to C10 (e.g., C2, C3, C4, C5, C6, C7, C8, or C9) alkoxy, C1 to C10 (e.g., C2, C3, C4, C5, C6, C7, C8, or C9) alkylthio, C6 to C20 (e.g., C6, C9, C10, C12, C14, C16, or C18) aryl, C2 to C20 (e.g., C3, C4, C5, C6, C8, C10, C12, C14, C16, or C18) heteroaryl, and C6 to C18 (e.g., C6, C9, C10, C12, C14, C16, or C18) arylamine.

In an embodiment, $n_1$, $n_2$, $n_3$, $n_4$, $n_5$, $n_6$, $m_1$, $m_2$, $m_3$, $m_4$, $m_5$, and $m_6$ are each independently an integer of 0-2, for example, 0, 1 or 2, and $m_1$, $m_2$, $m_3$, $m_4$, $m_5$, and $m_6$ are not simultaneously 0.

In an embodiment, the organic compound is any one selected from the group consisting of the following compounds P1 to P233:

P1

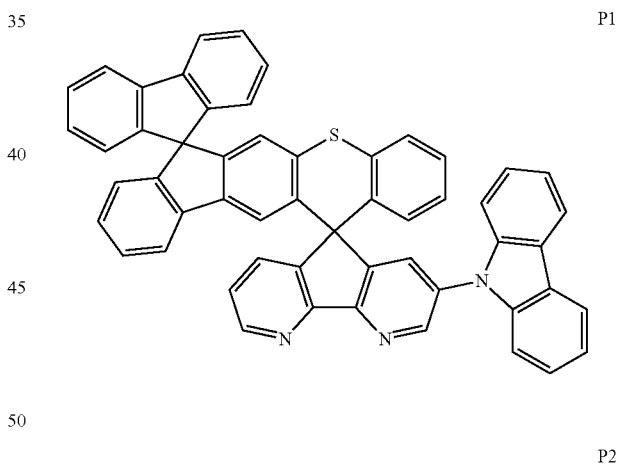

P2

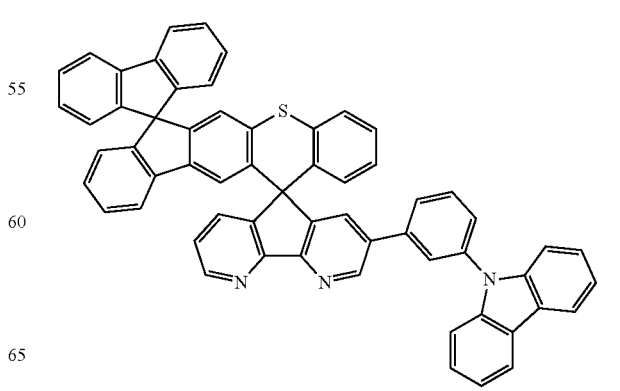

-continued
P3
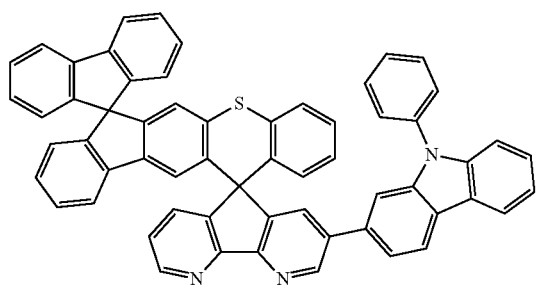
P4
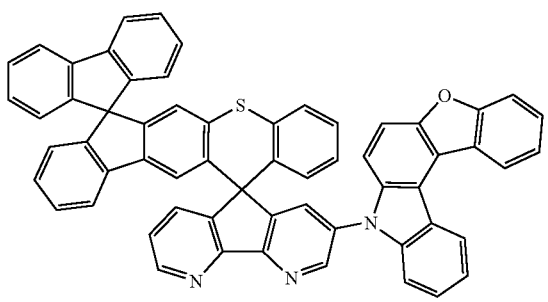
P5
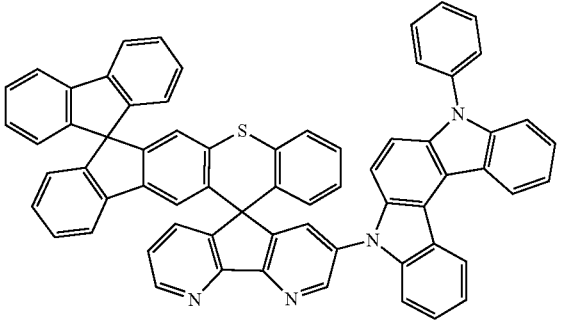
P6
-continued
P7
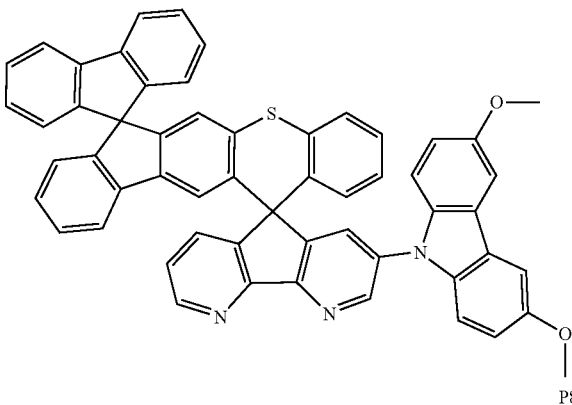
P8
P9
P10
P11
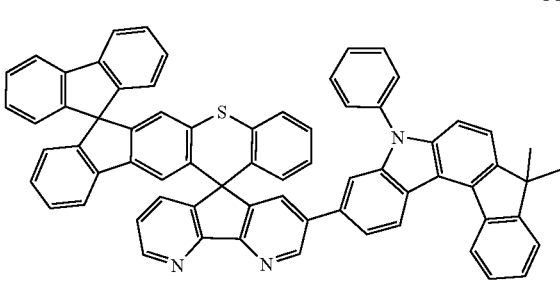

-continued
P12
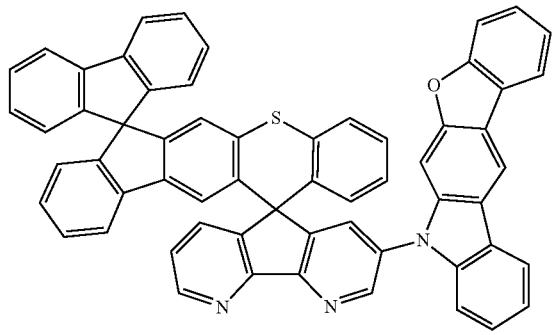
P13
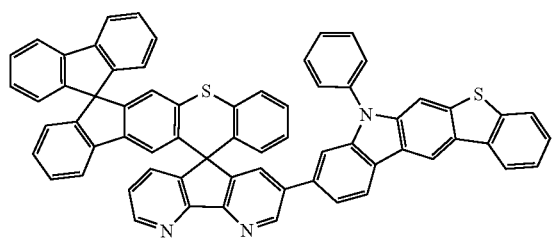
P14
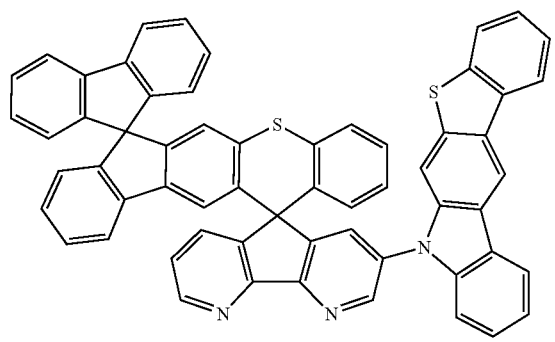
P15
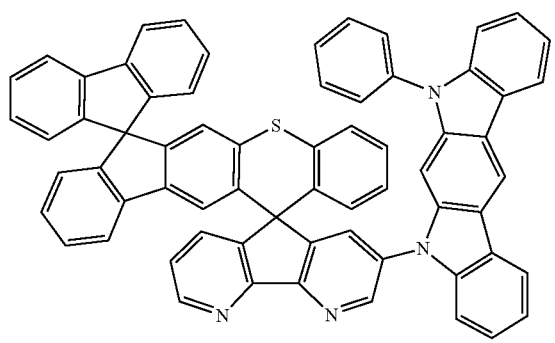
-continued
P16
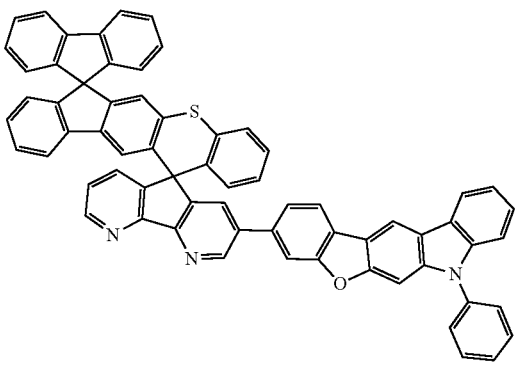
P17
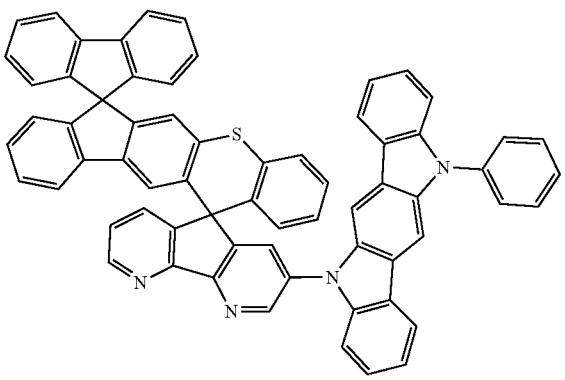
P18
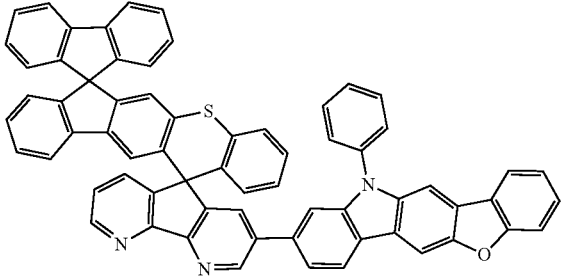
P19
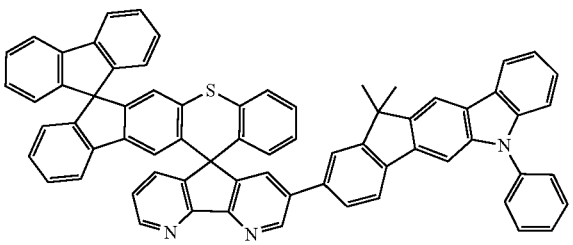

27
-continued
P20
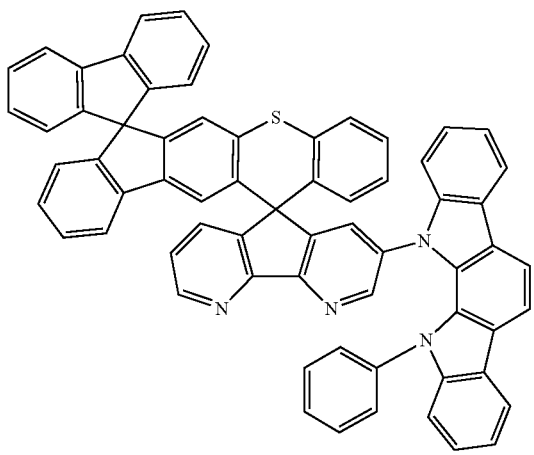
P21
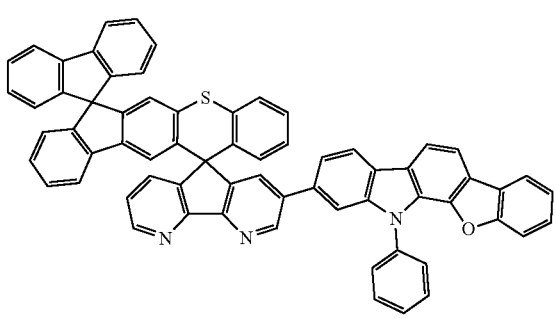
P22
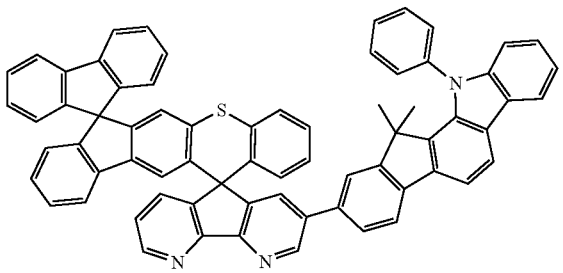
P23
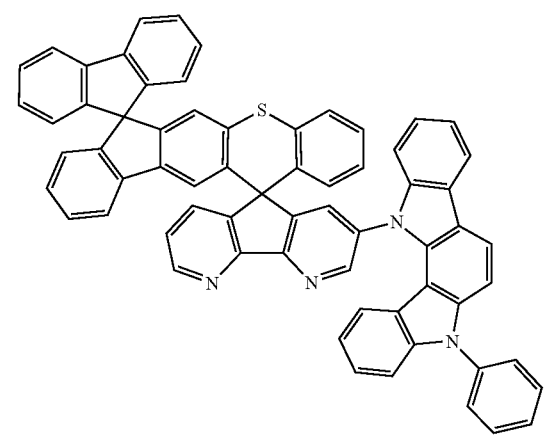
28
-continued
P24
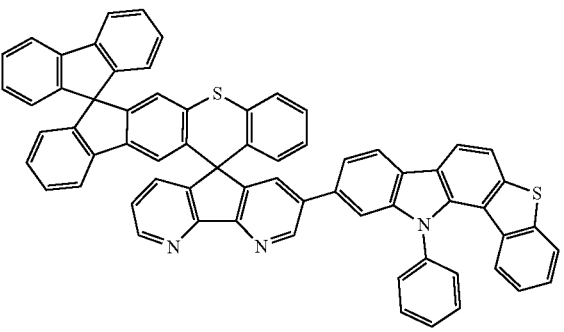
P25
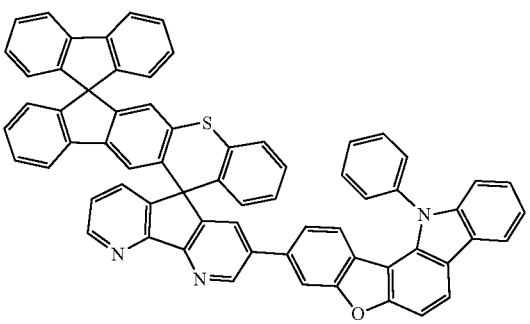
P26
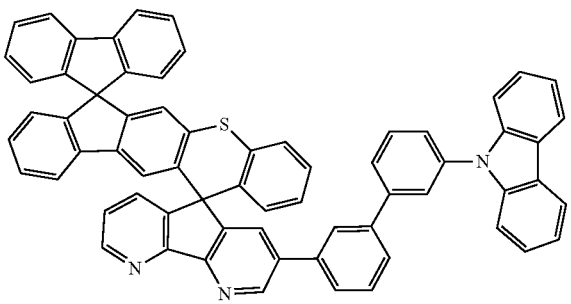
P27
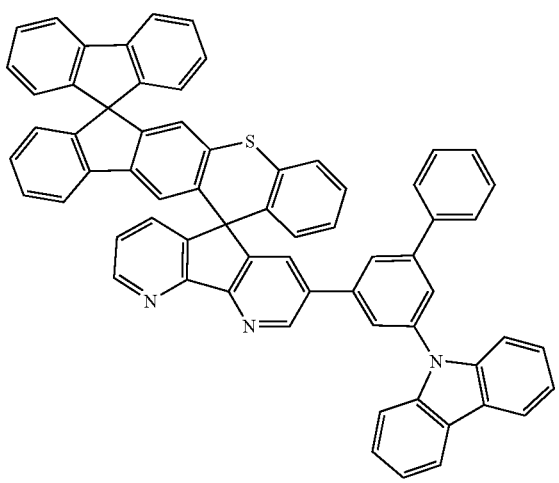

P28
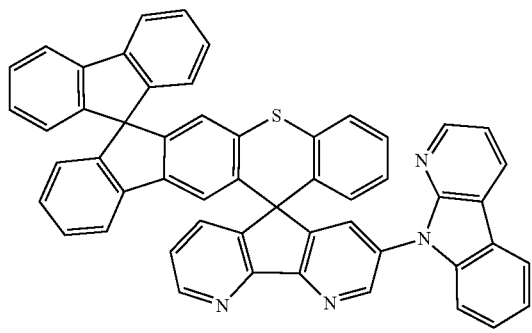
P29
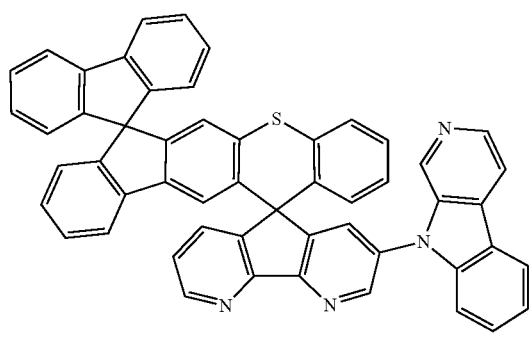
P30
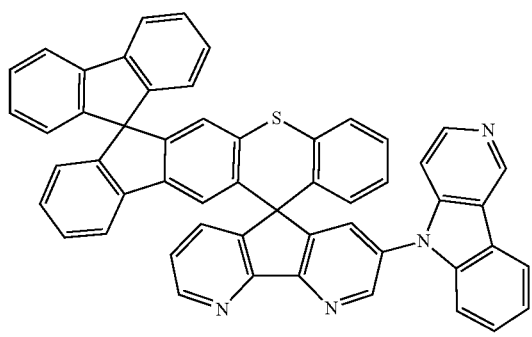
P31
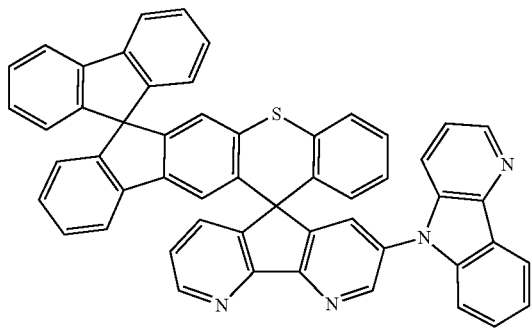
P32
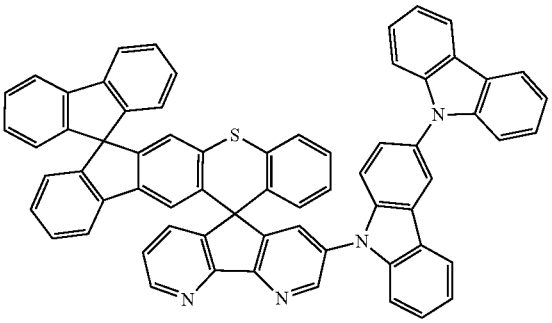
P33
P34
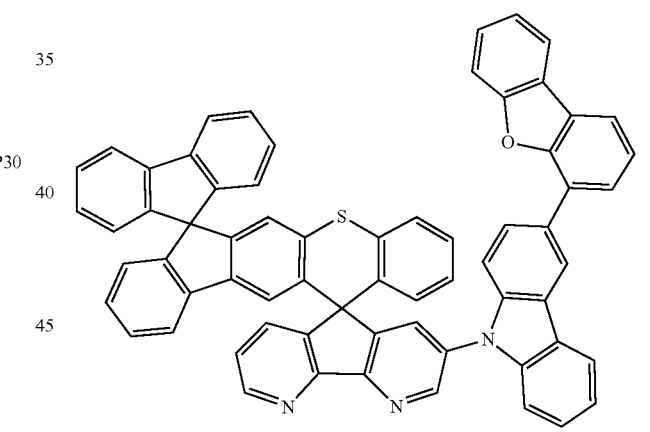
P35
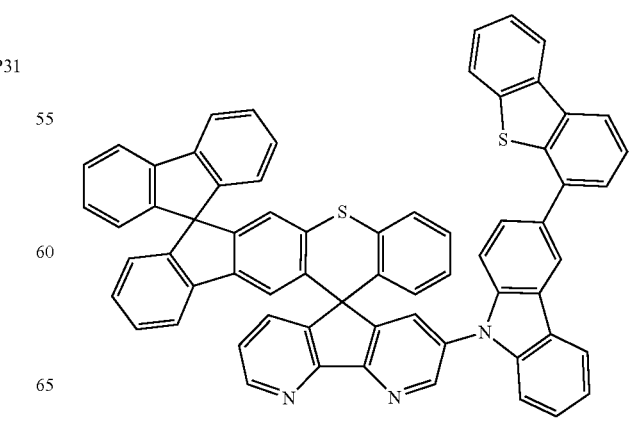

P36
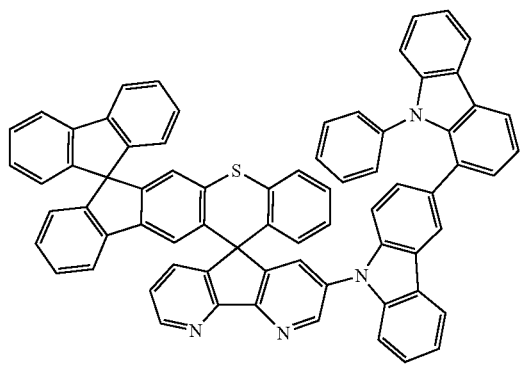
P37
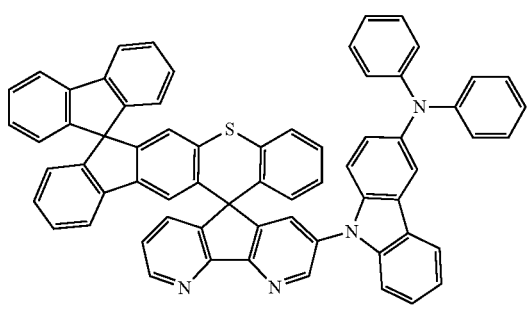
P38
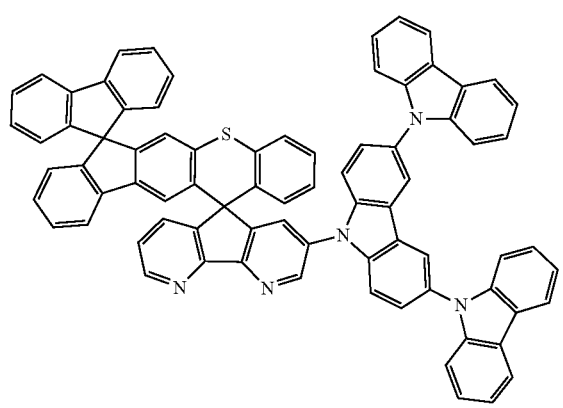
P39
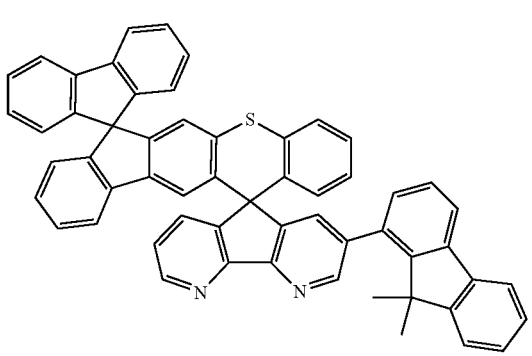
P40
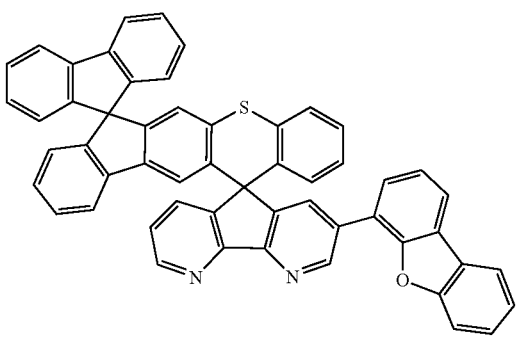
P41
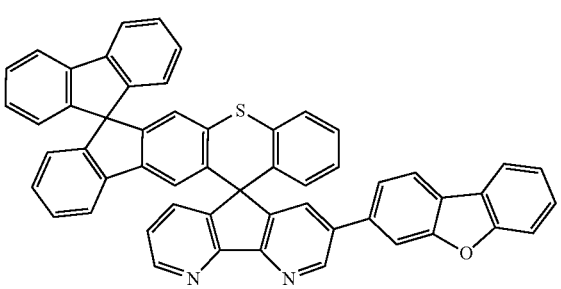
P42
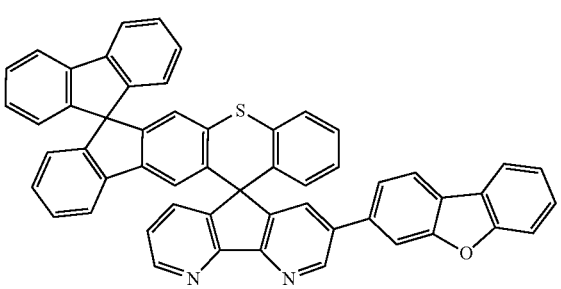
P43
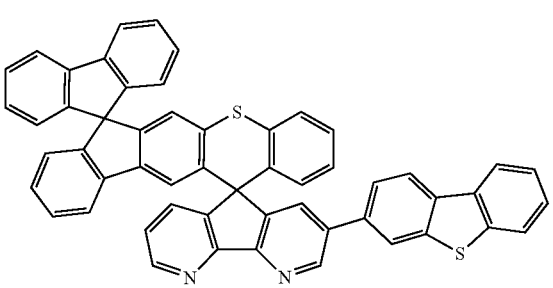

-continued
P44
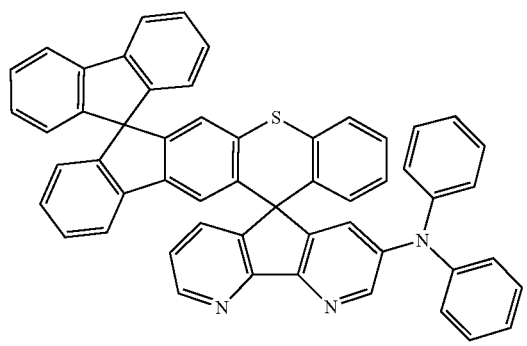
P45
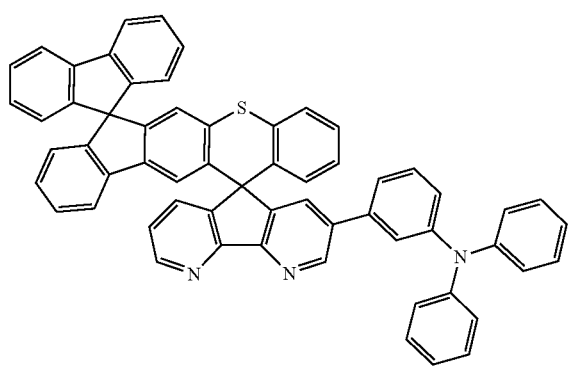
P46
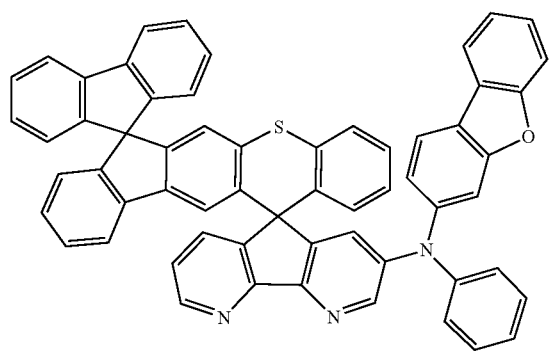
P47
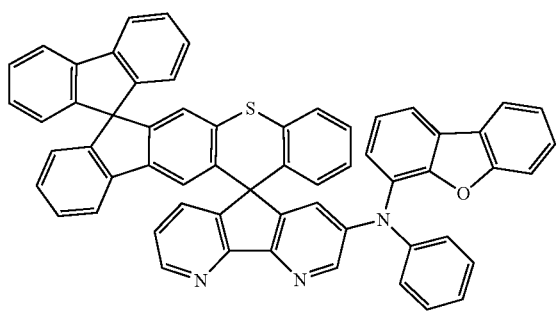
-continued
P48
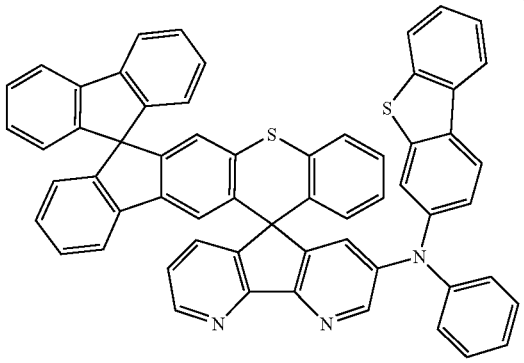
P49
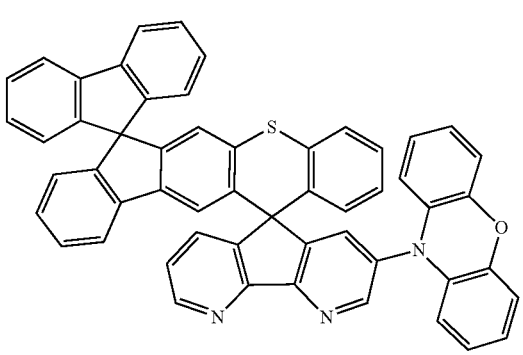
P50
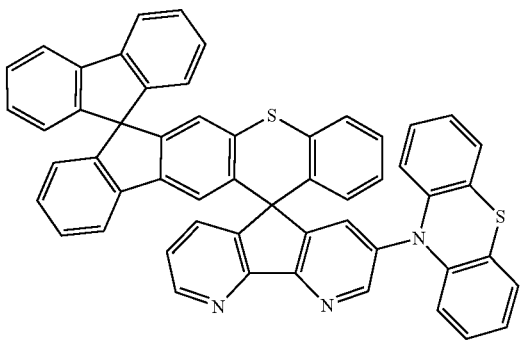
P51
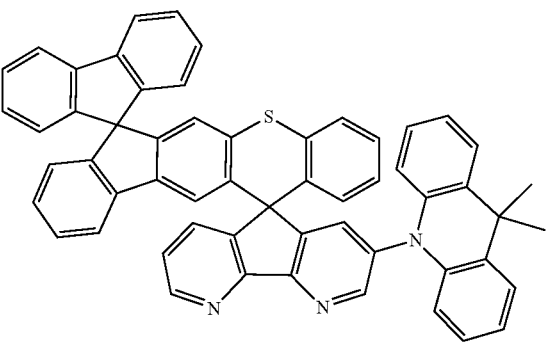

-continued
P52
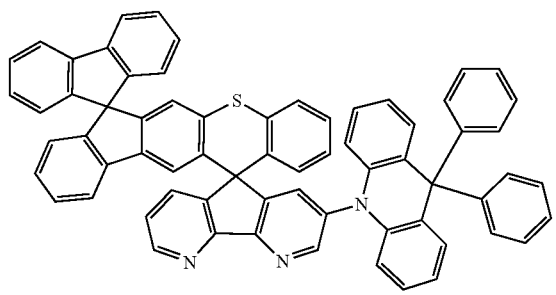
P53
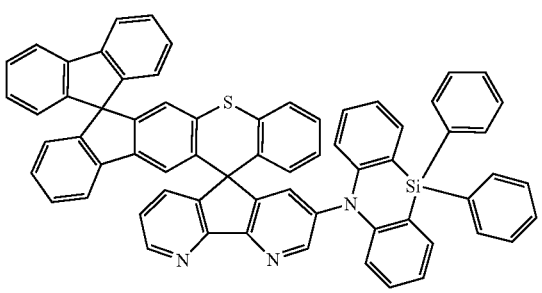
P54
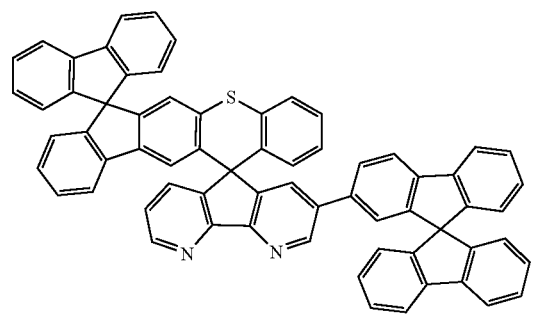
P55
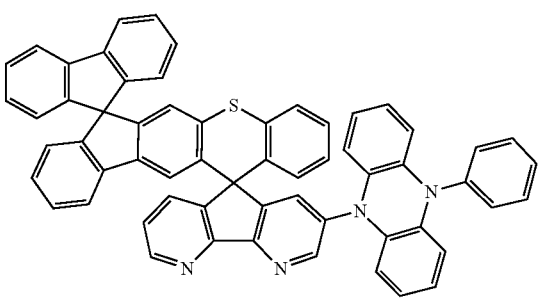
-continued
P56
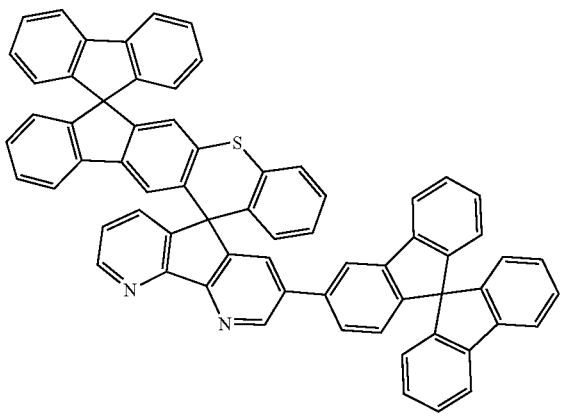
P57
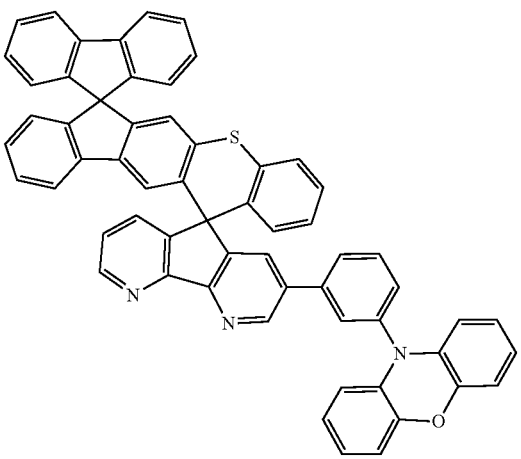
P58
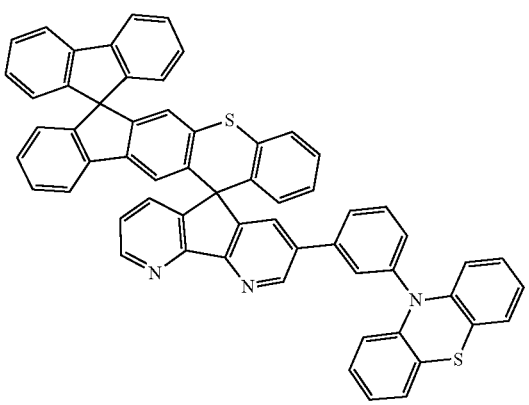

P59
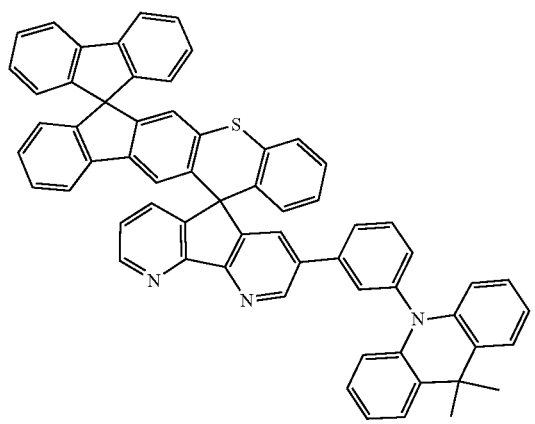
P60
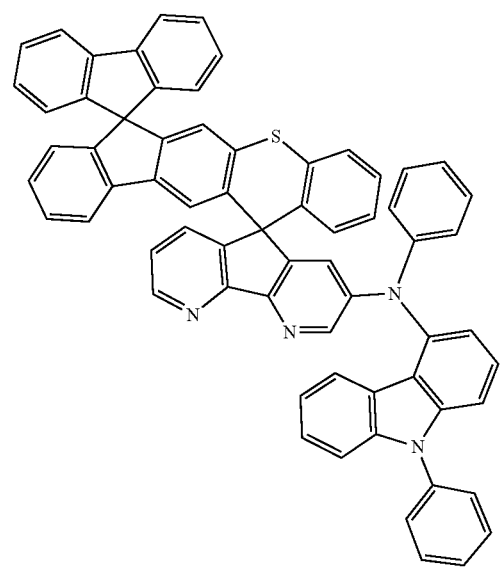
P61
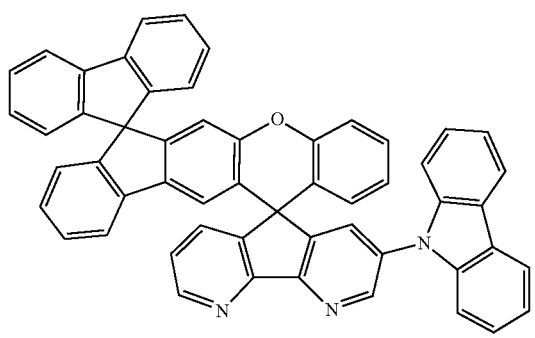
P62
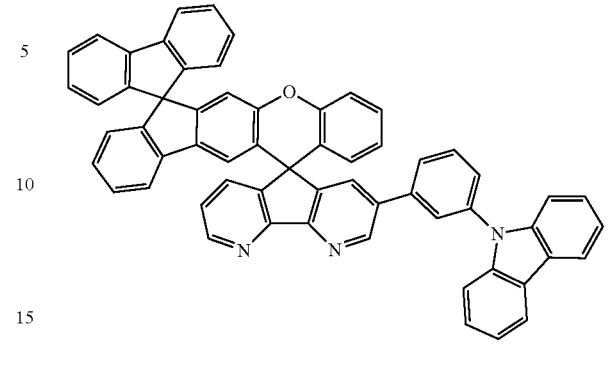
P63
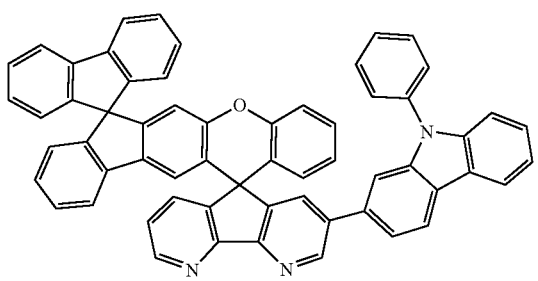
P64
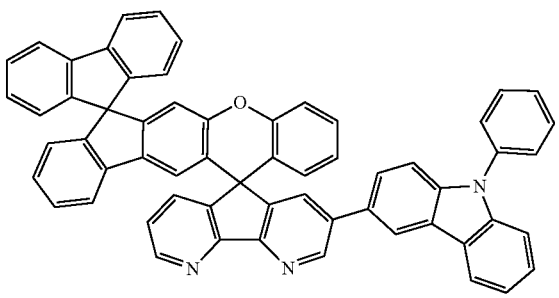
P65
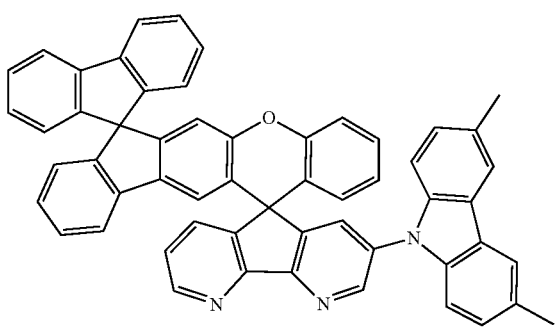

P66
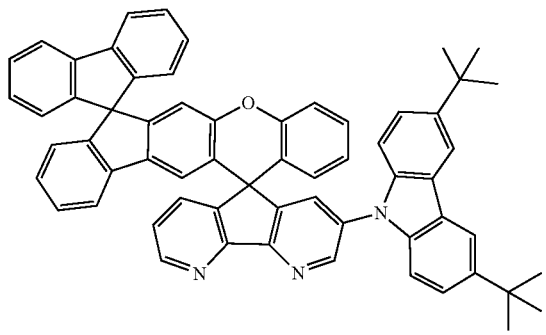
P67
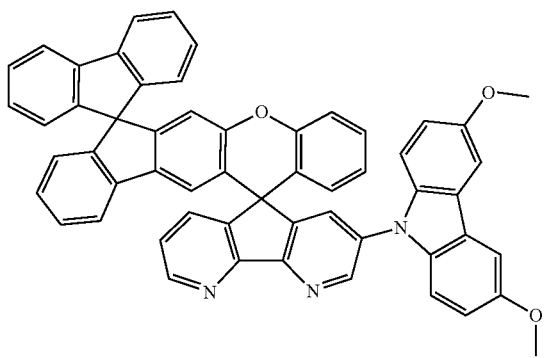
P68
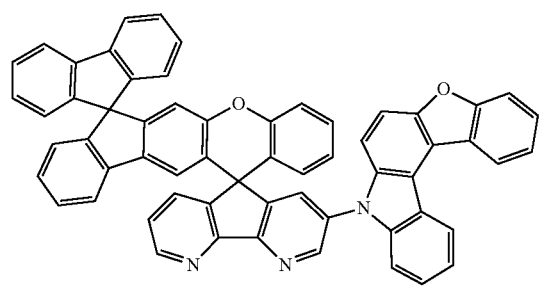
P69
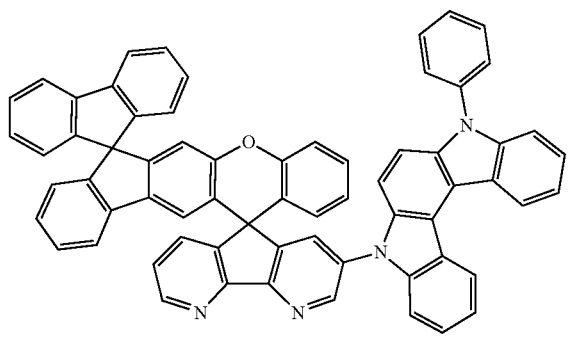
P70
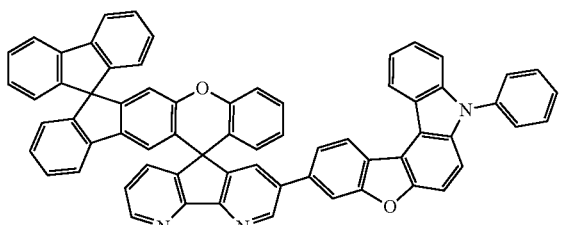
P71
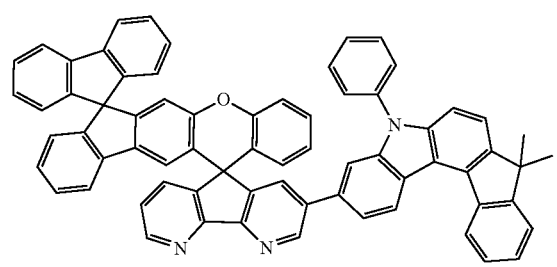
P72
P73
P74
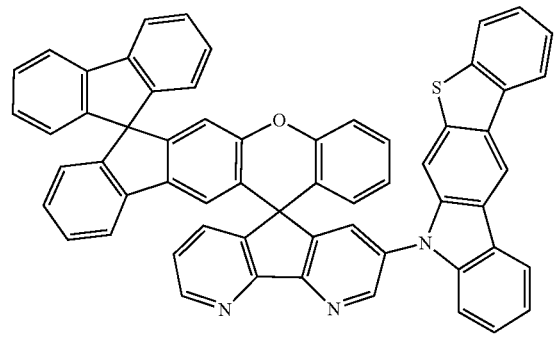

P75
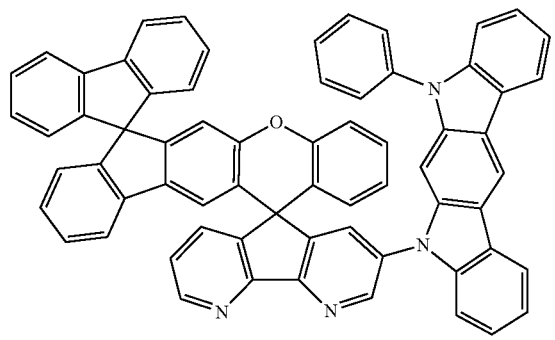
P79
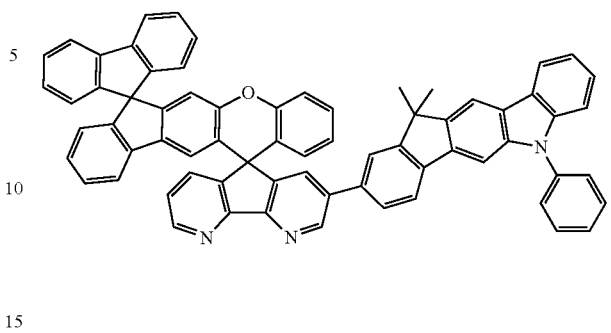
P76
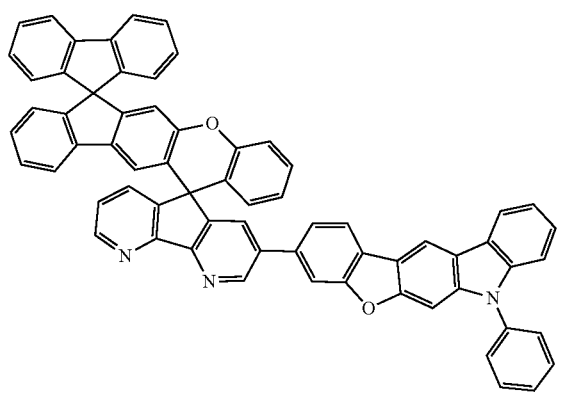
P80
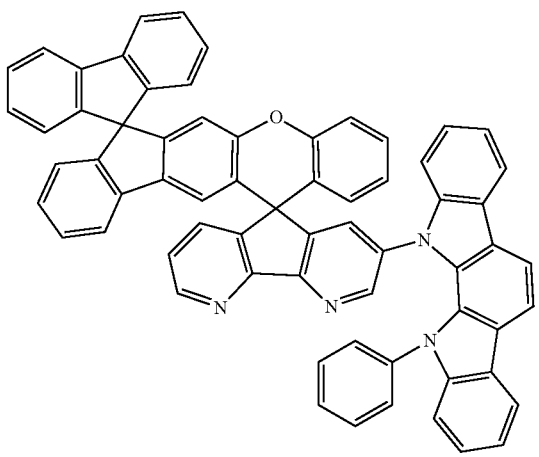
P77
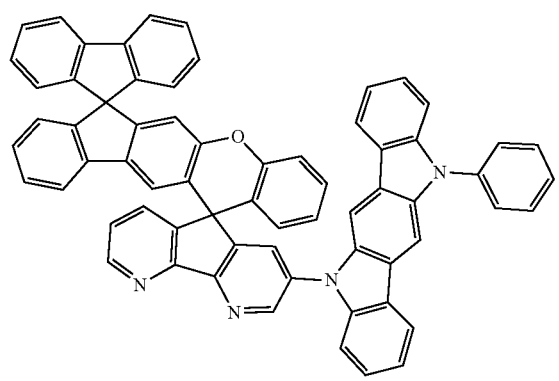
P81
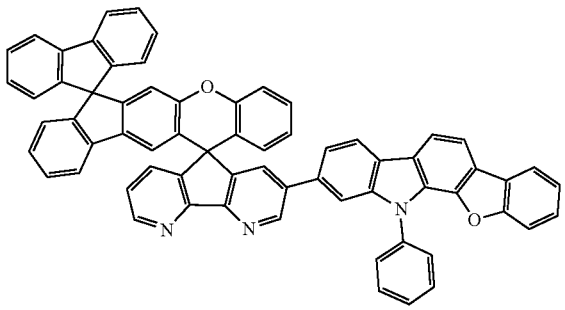
P78
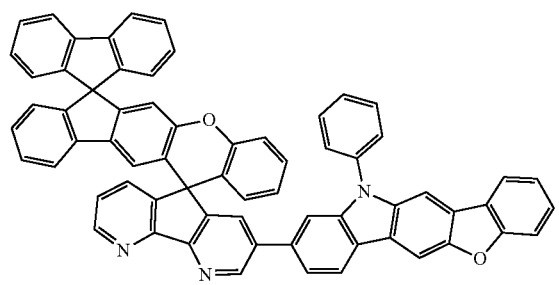
P82
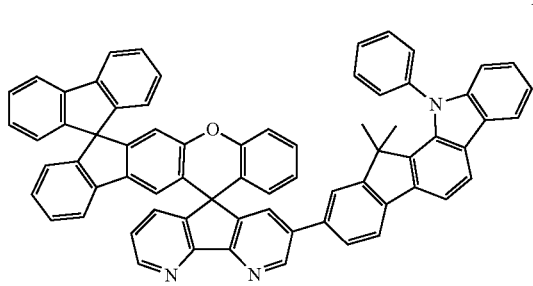

P83
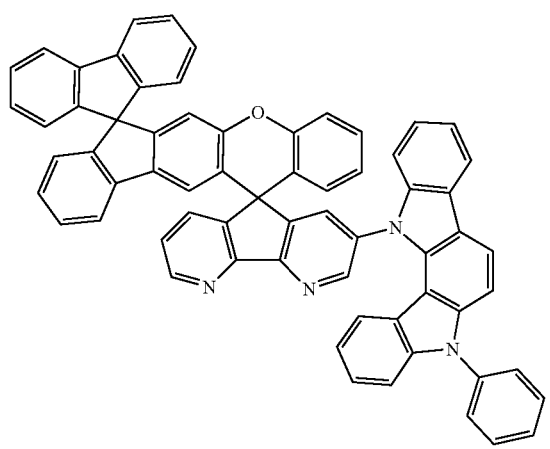
P84
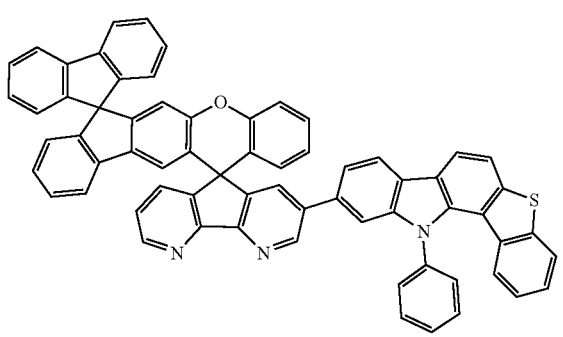
P85
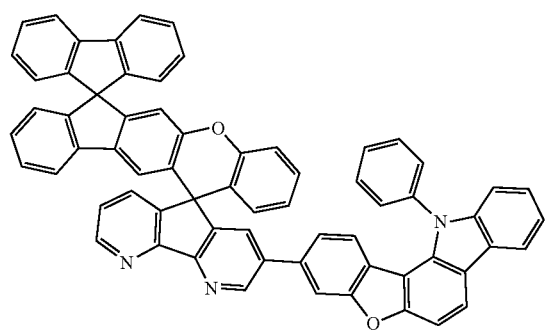
P86
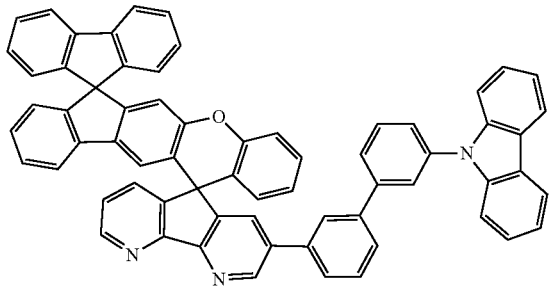
P87
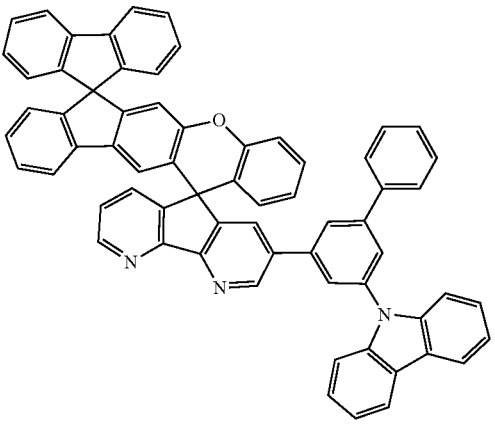
P88
P89
P90
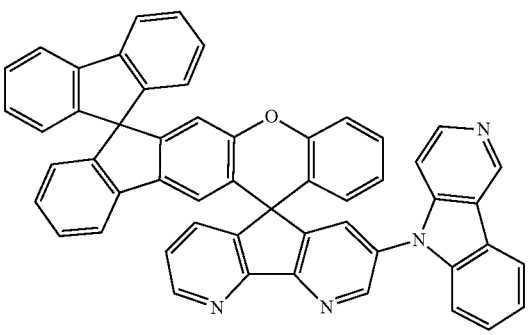

P91
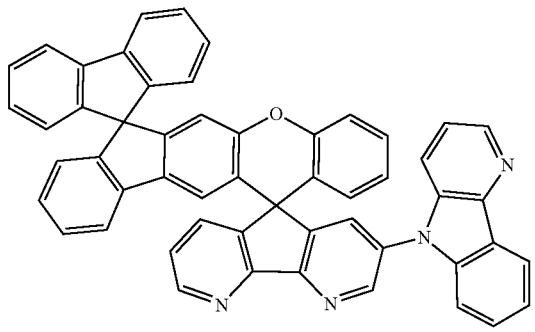
P92
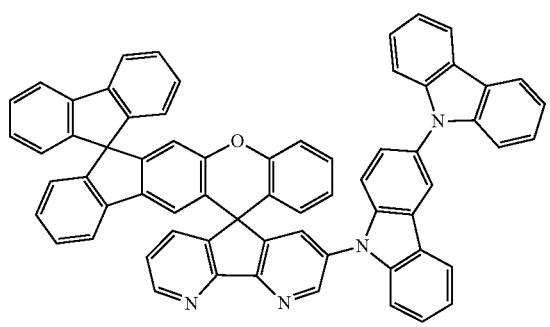
P93
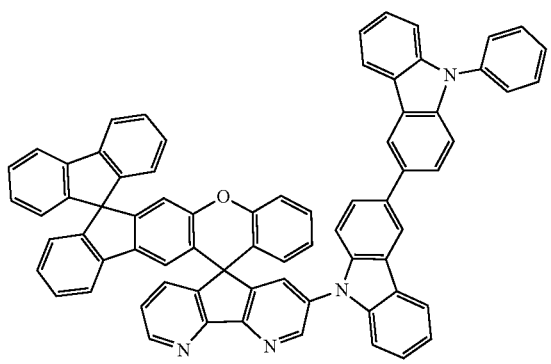
P94
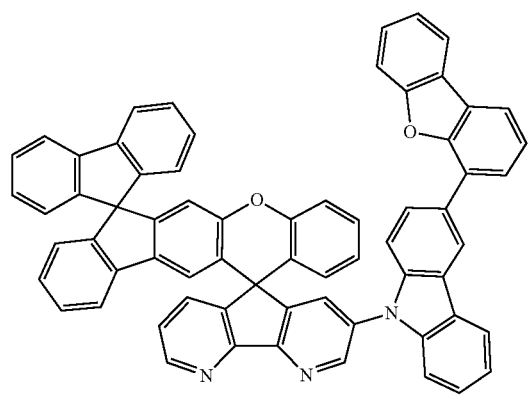
P95
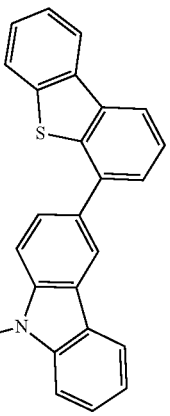
P96
P97
P98
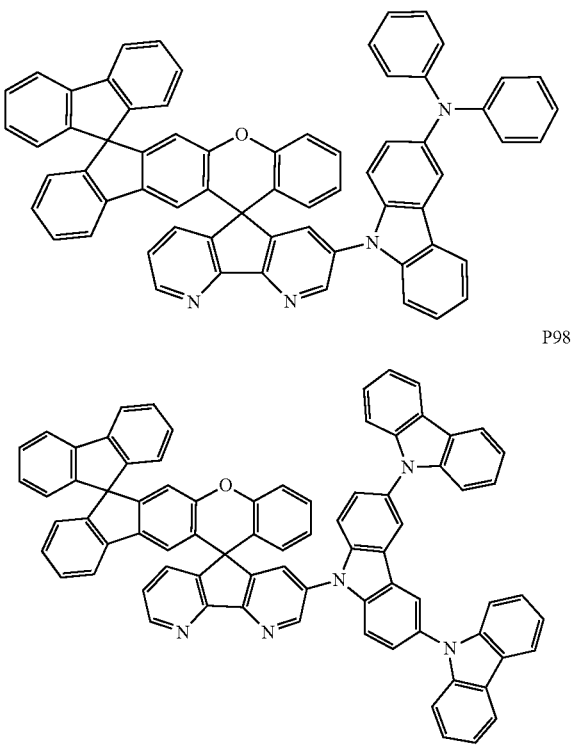

P99
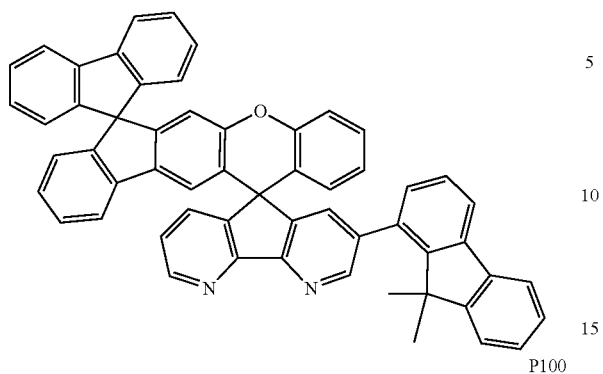
P100
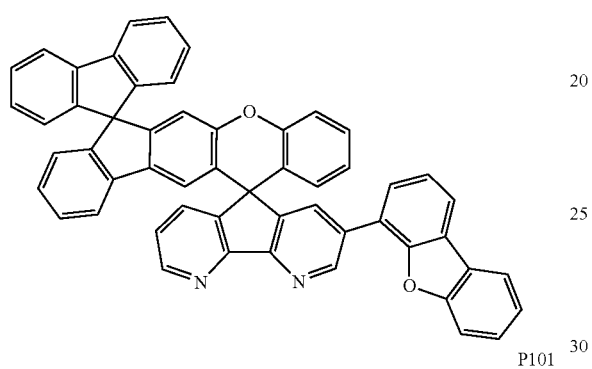
P101
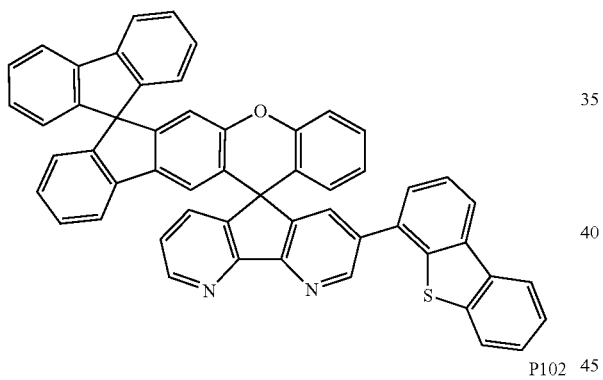
P102
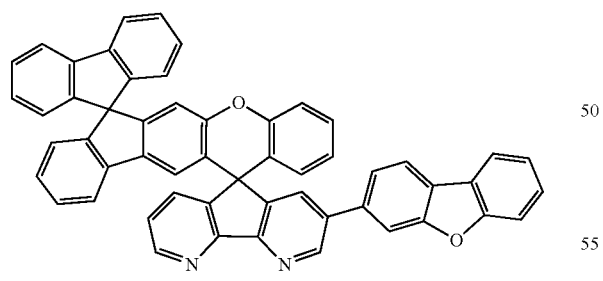
P104
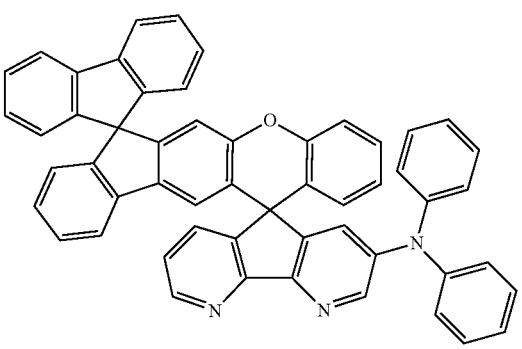
P105
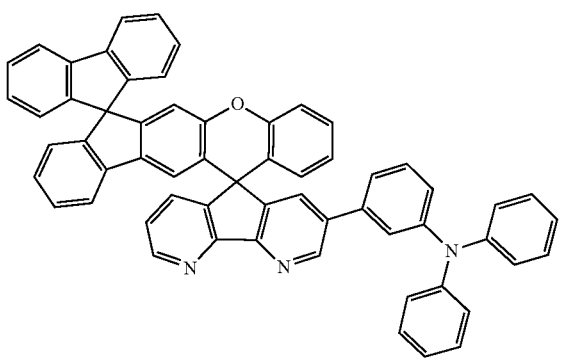
P106
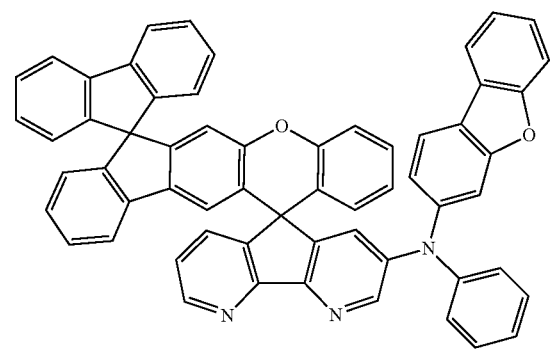
P107
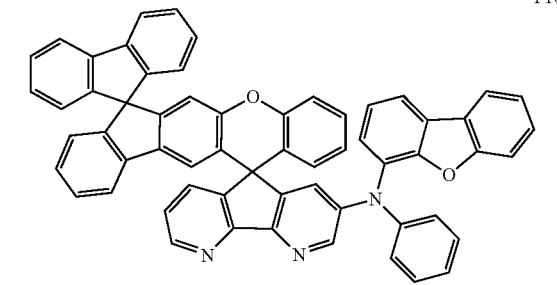

P108

P109

P110

P111

P112

P113

P114

P115

P116
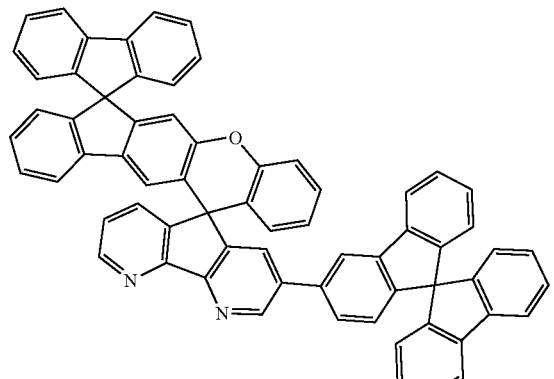
P119
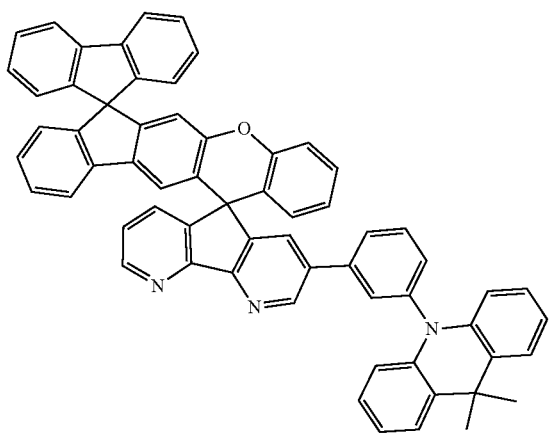
P117
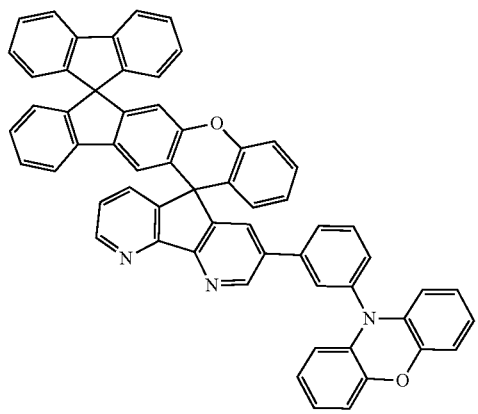
P120
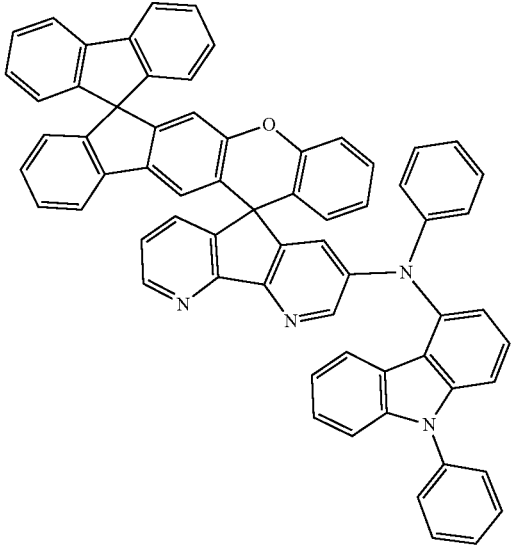
P118
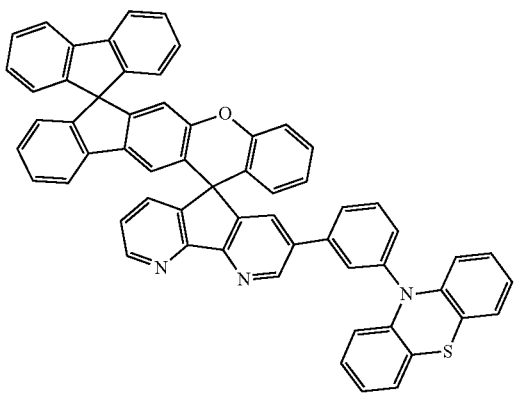
P121
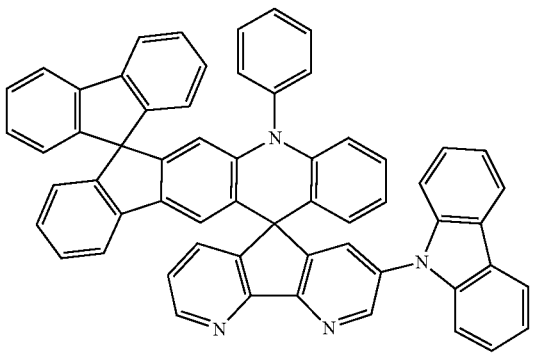

P122
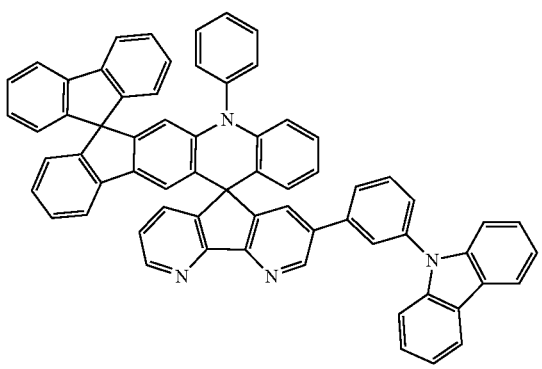
P123
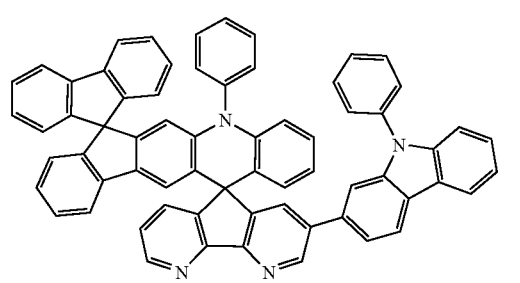
P124
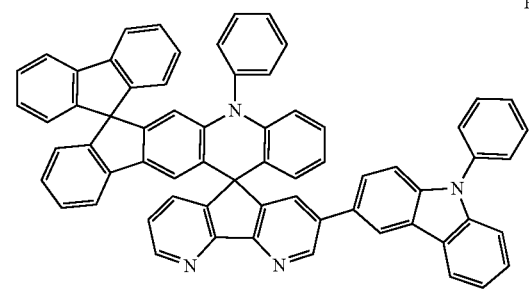
P125
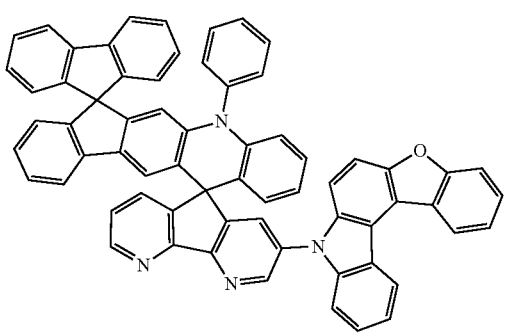
P126
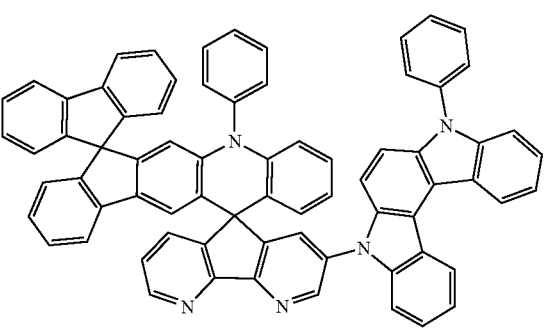
P127
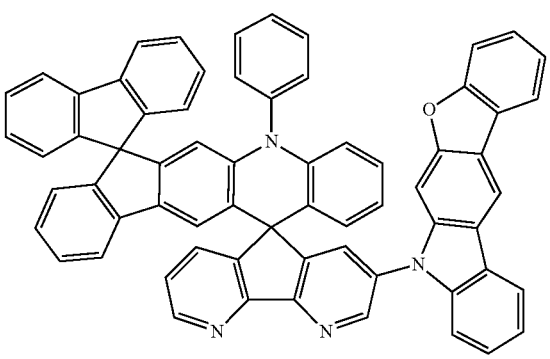
P128
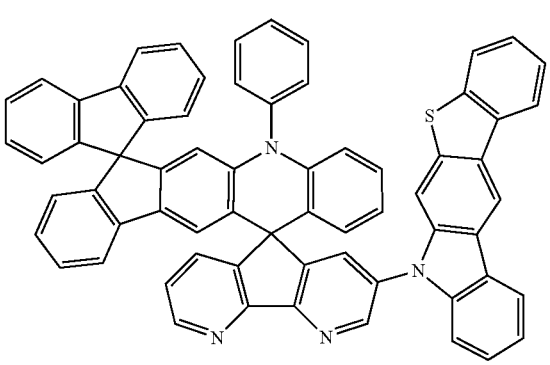
P129
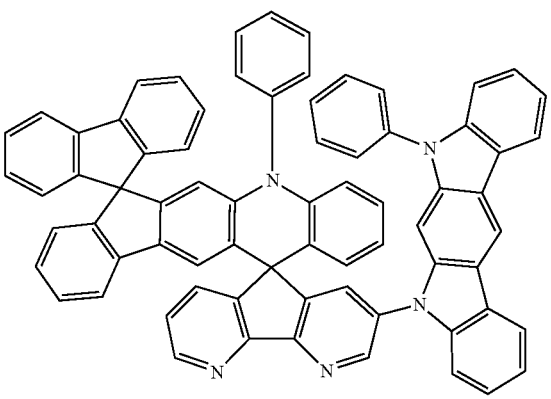
P130
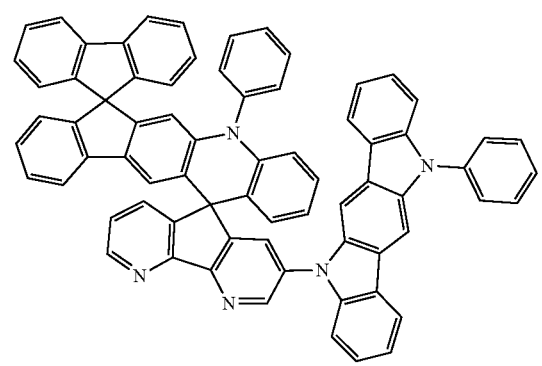

P131
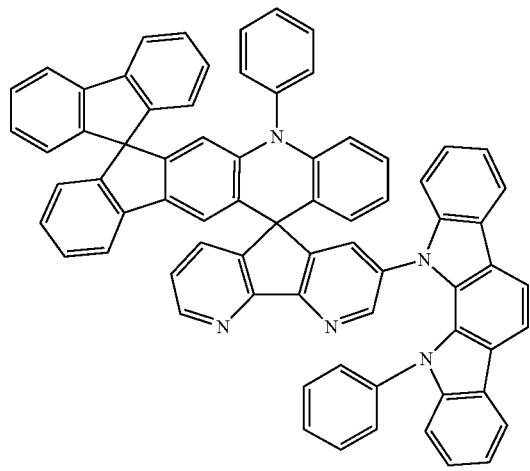
P132
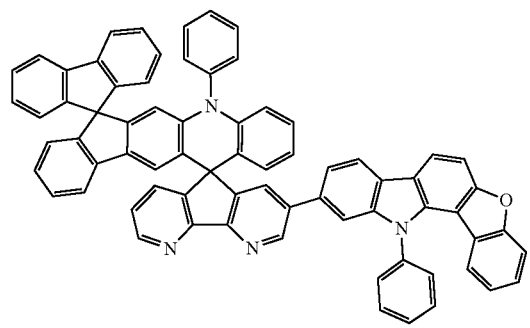
P133
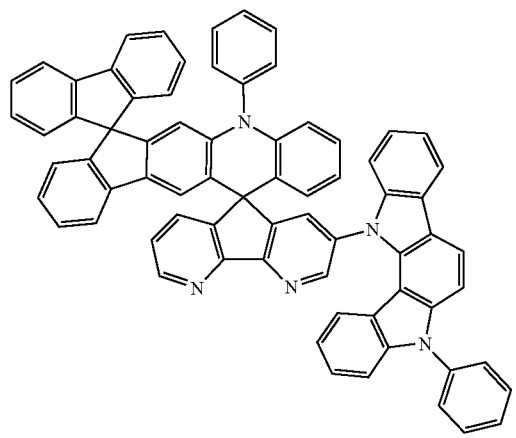
P134
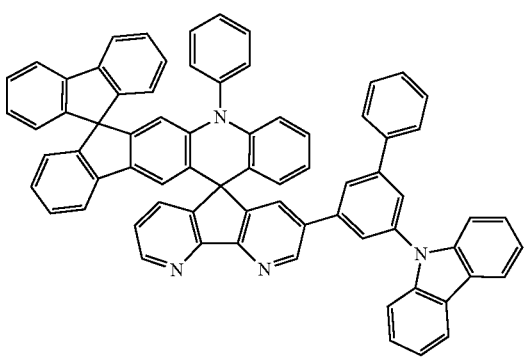
P135
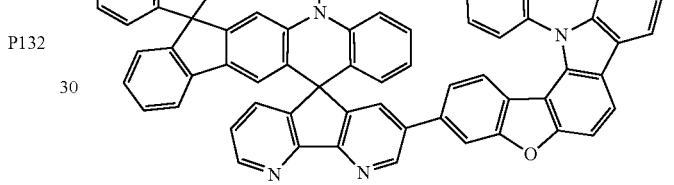
P136
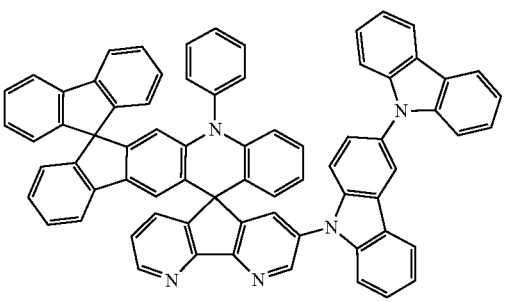
P137
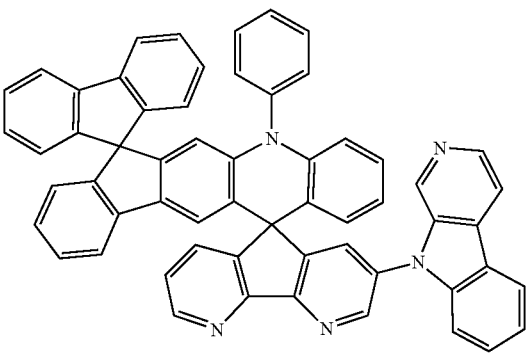

-continued
P138
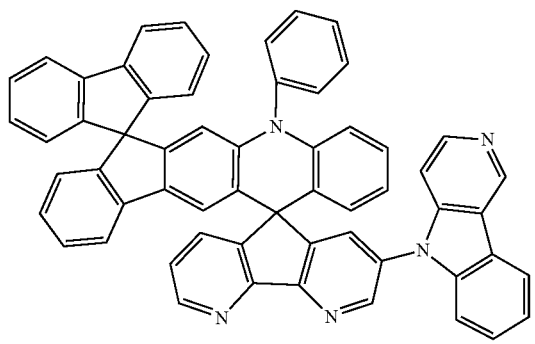
P139
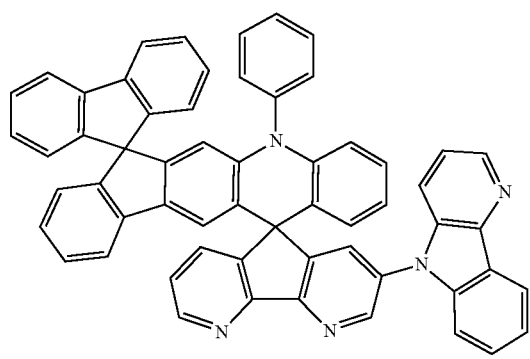
P140
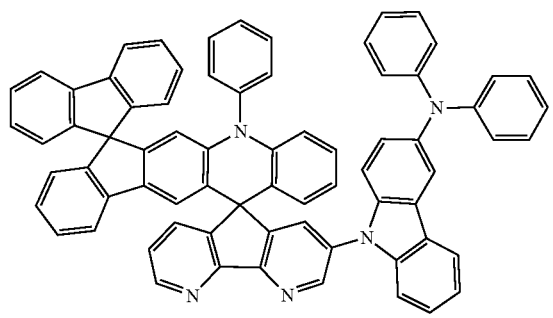
P141
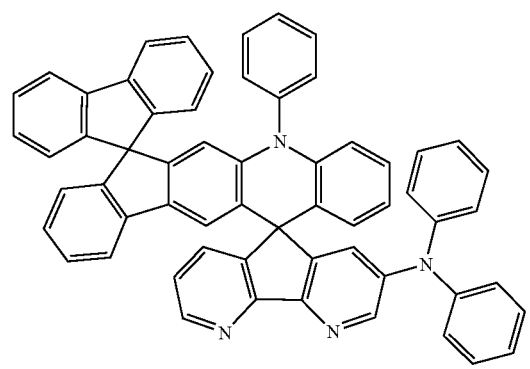
P142
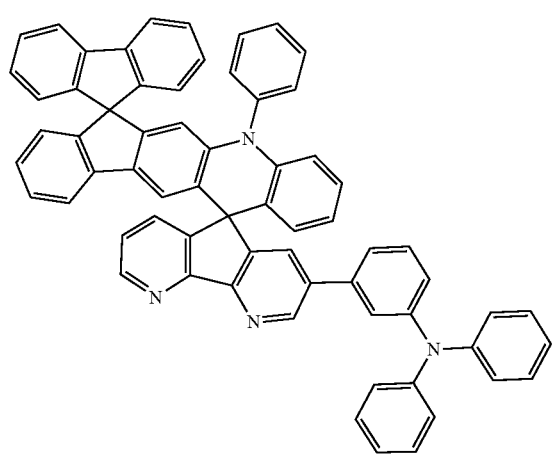
P143
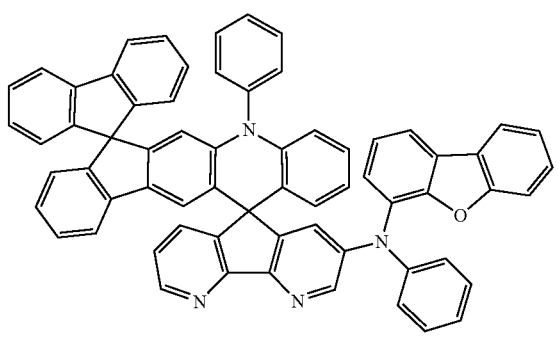
P144
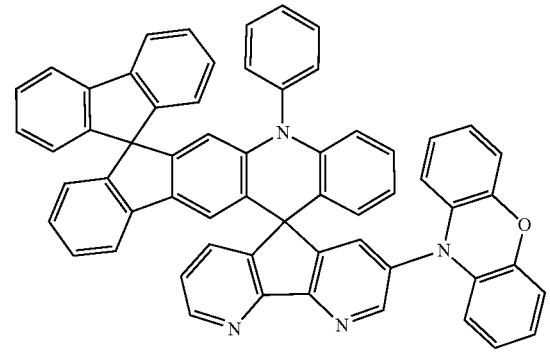
P145
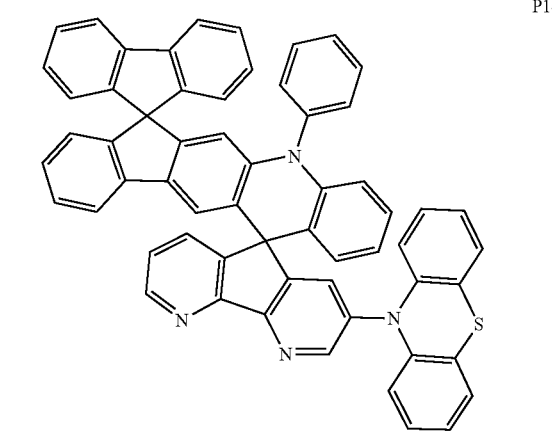

P146
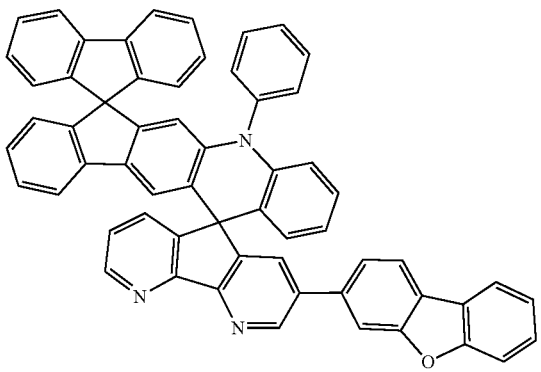
P147
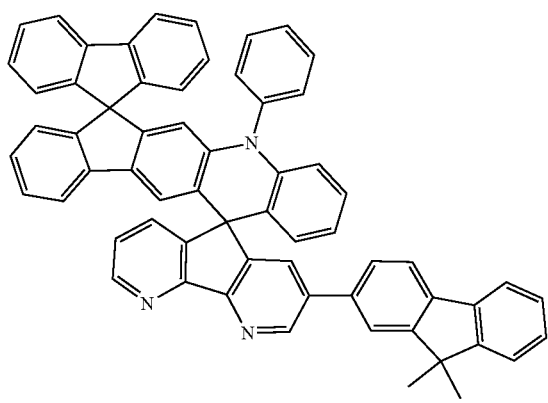
P148
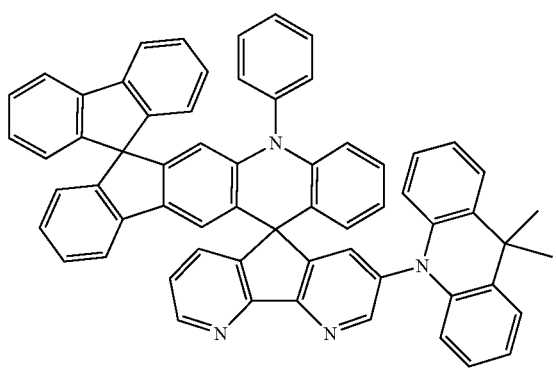
P149
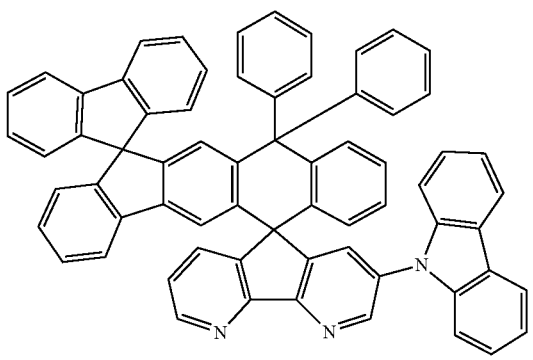
P150
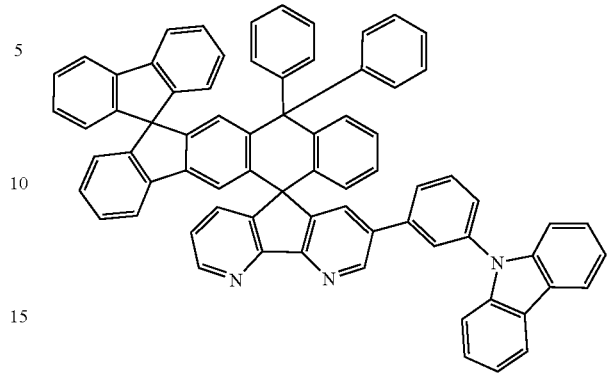
P151
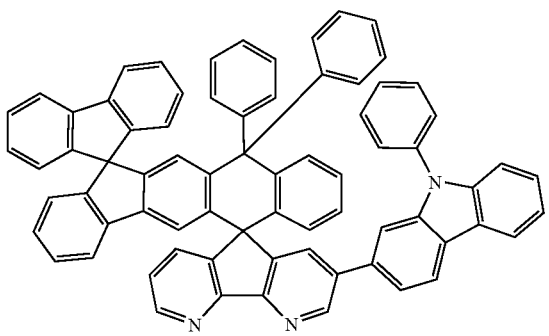
P152
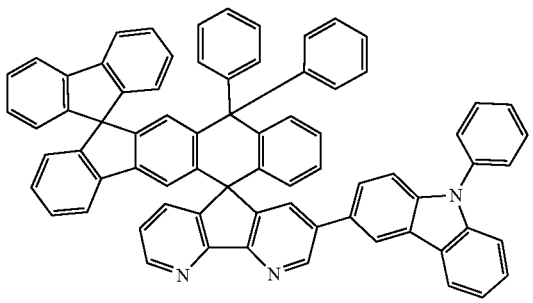
P153
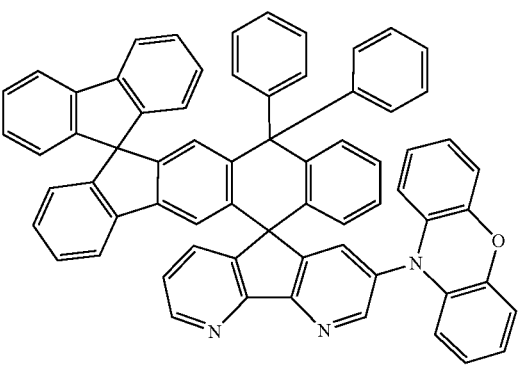

P154
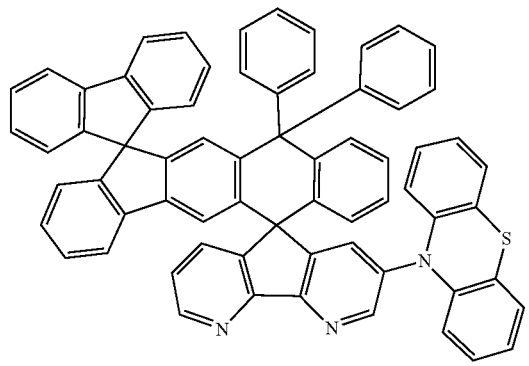
P155
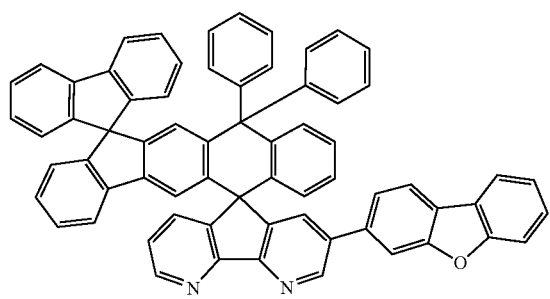
P156
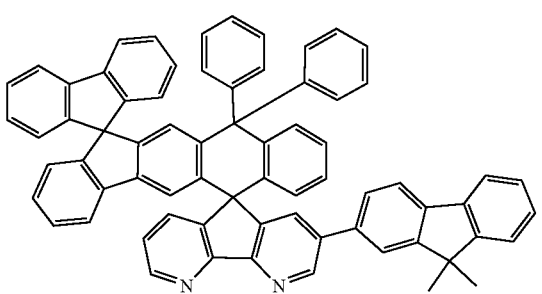
P157
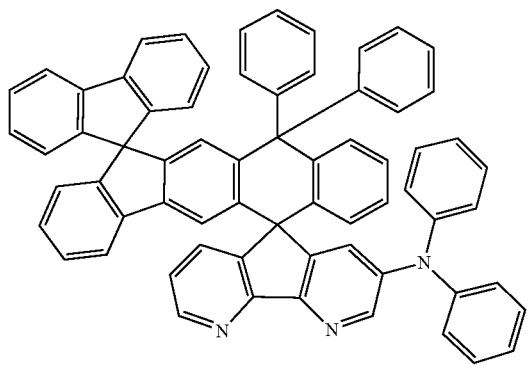
P158
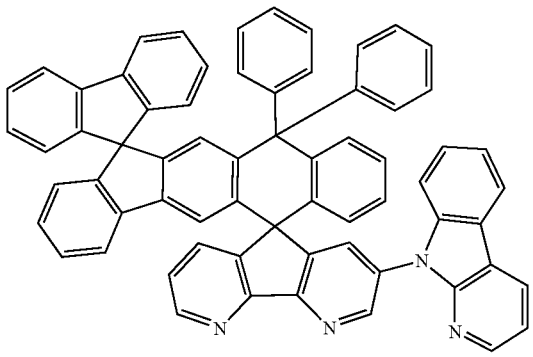
P159
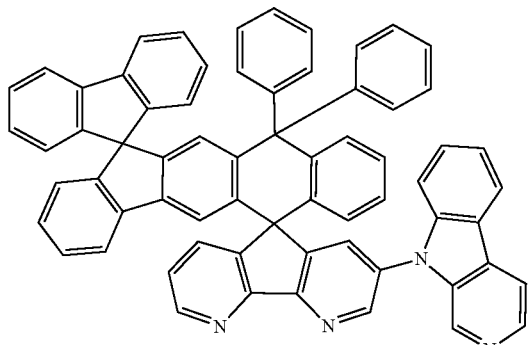
P160
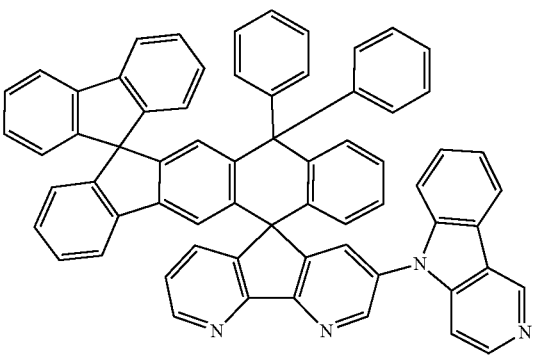
P161
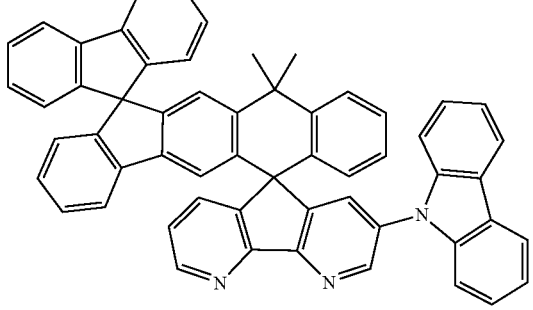

-continued
P162
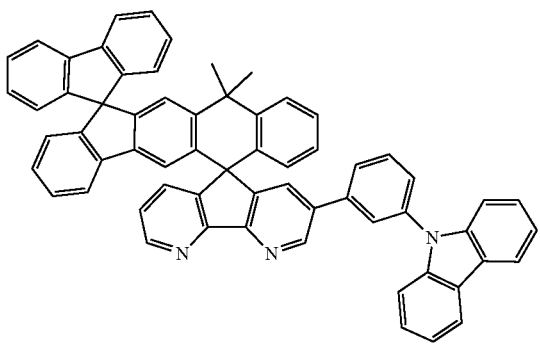
P163
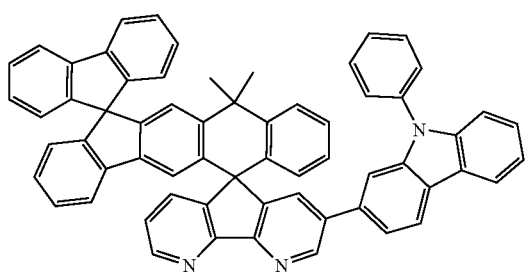
P164
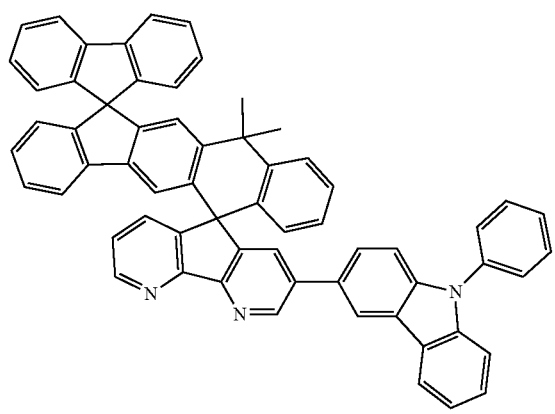
P165
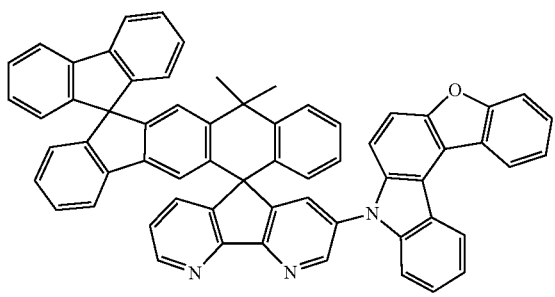
-continued
P166
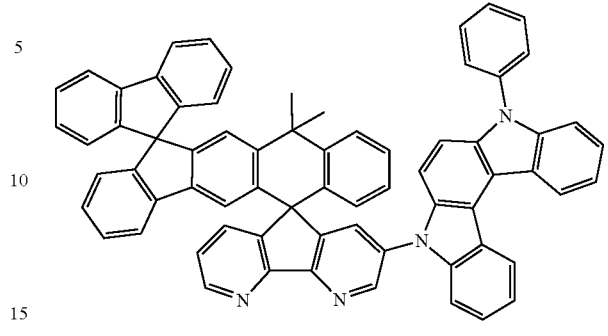
P167
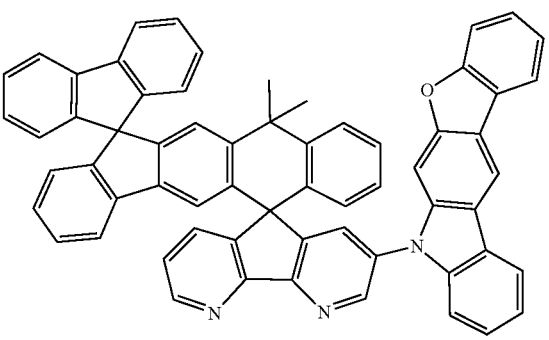
P168
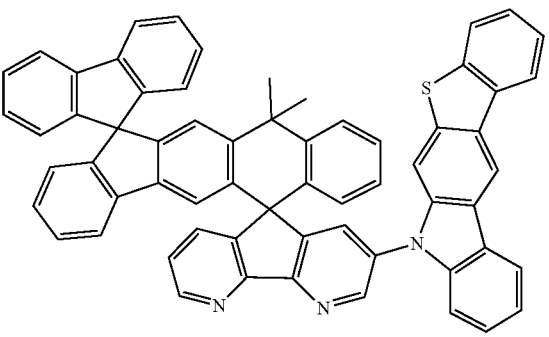
P169
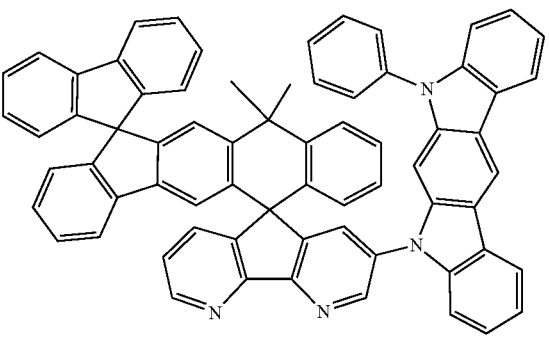

-continued
P170
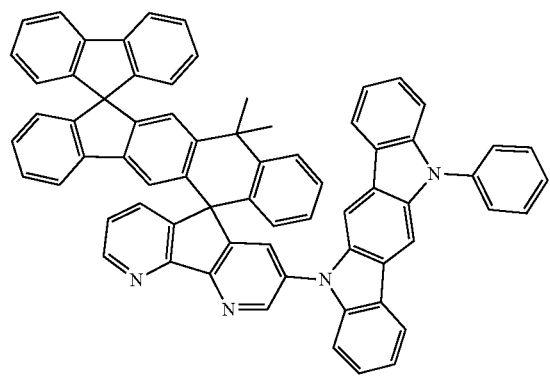
P171
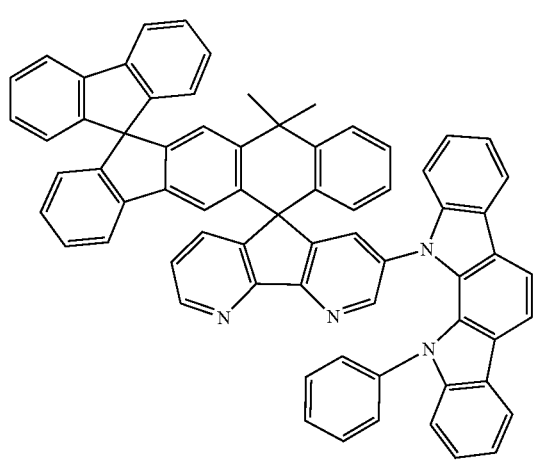
P172
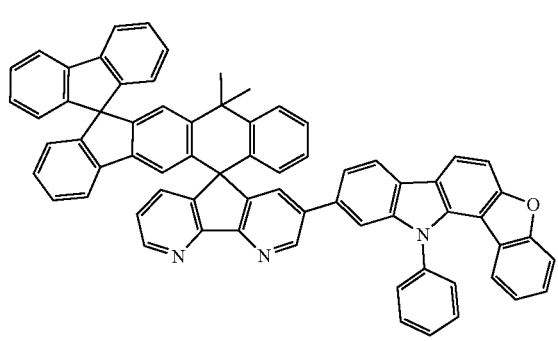
P173
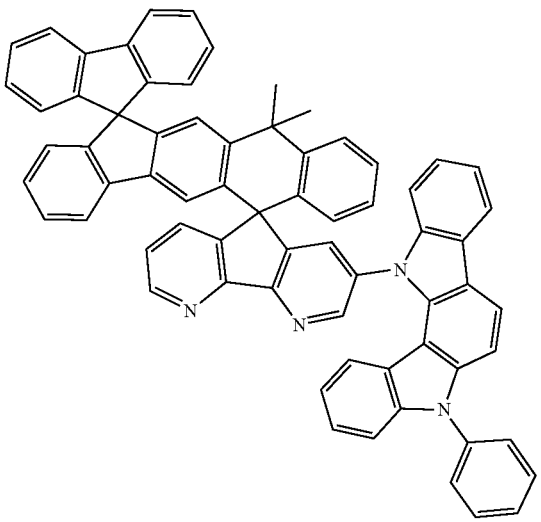
P174
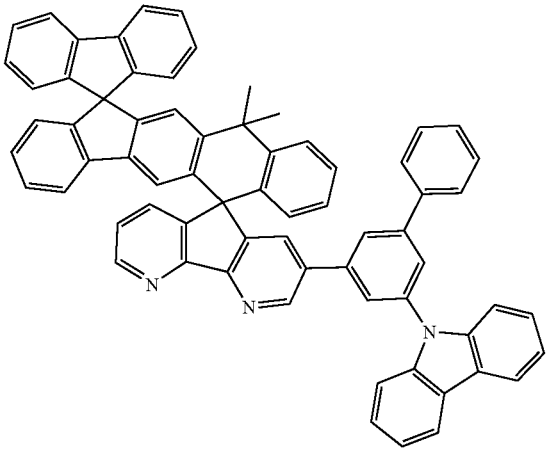
P175
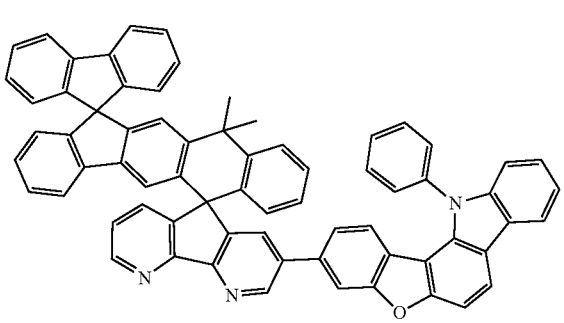

P176
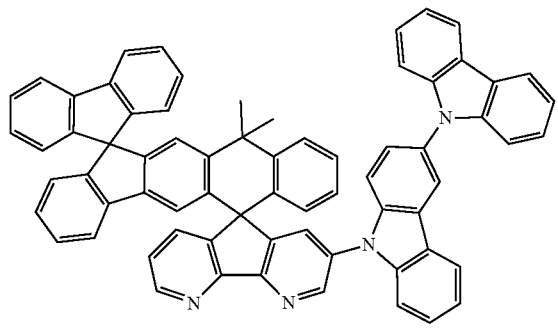
P180
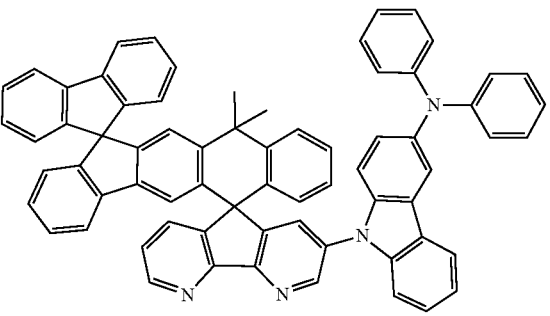
P177
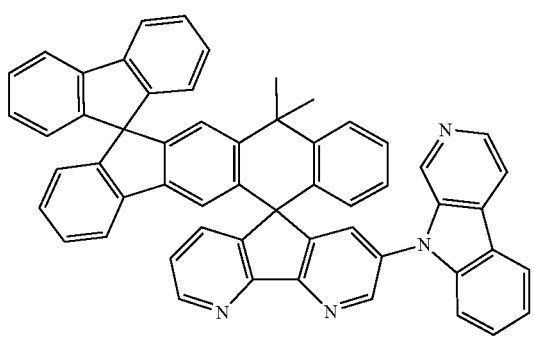
P181
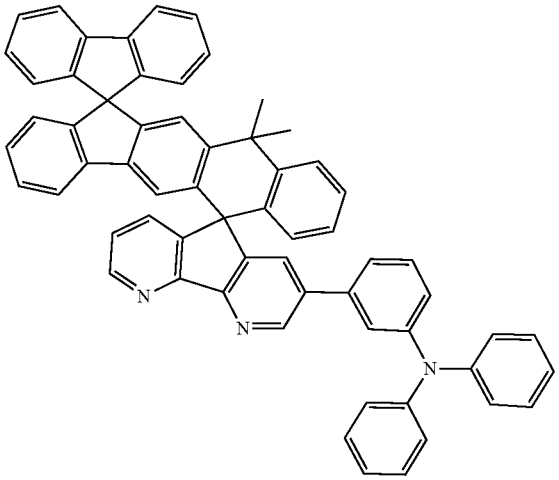
P178
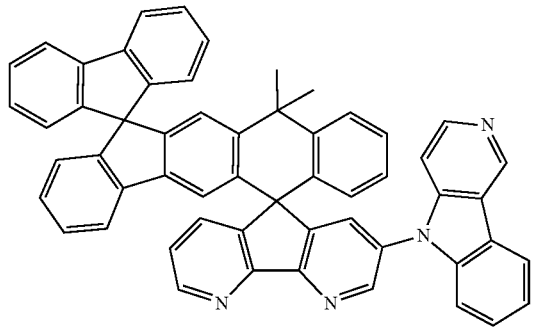
P182
P179
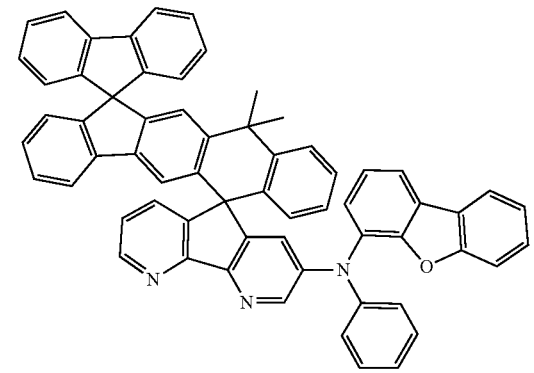
P183

P184
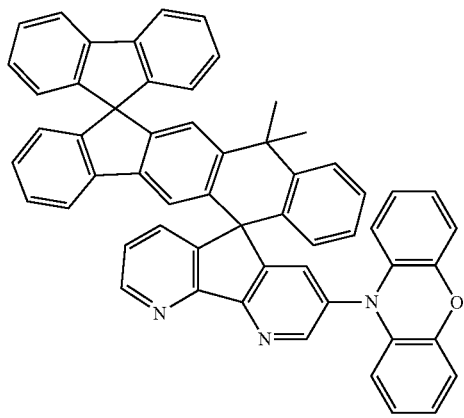
P185
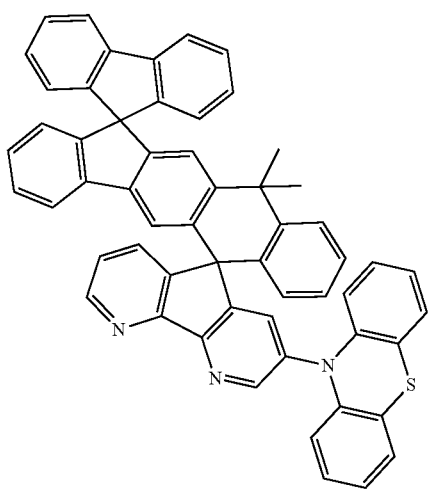
P186
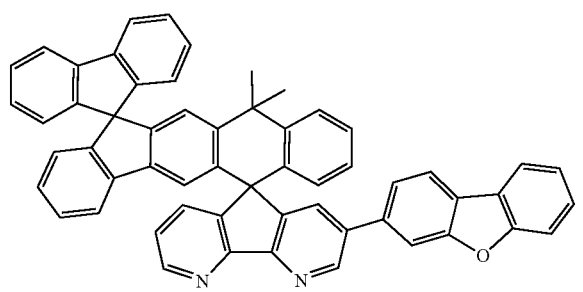
P187
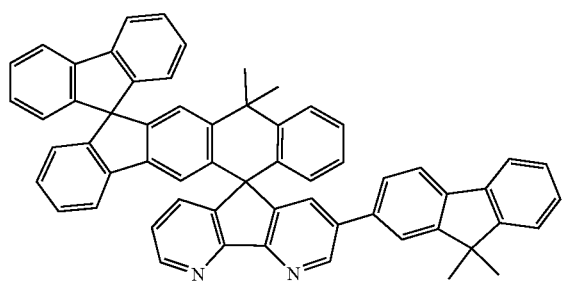
P188
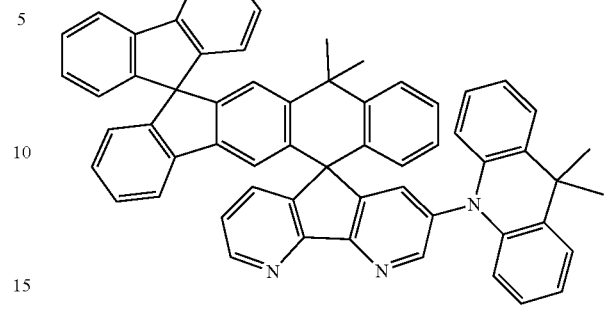
P189
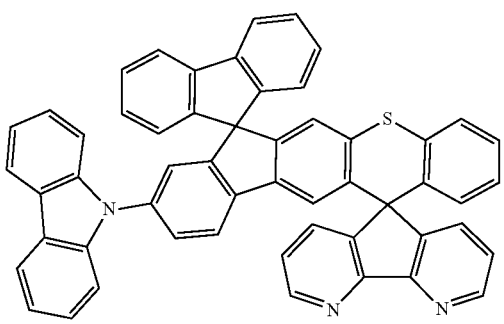
P190
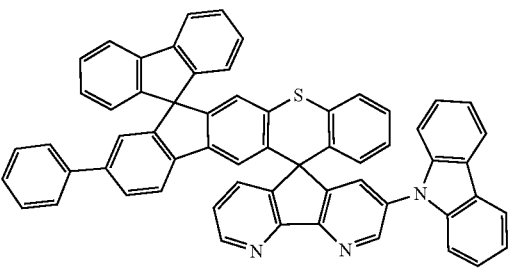
P191
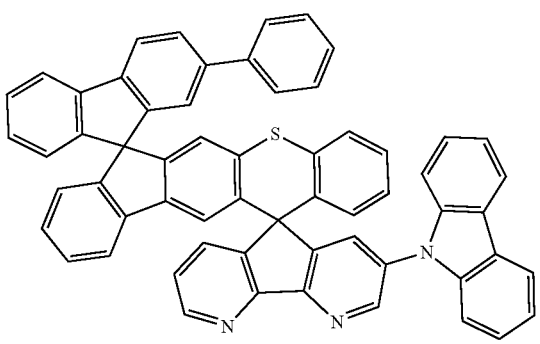

P192
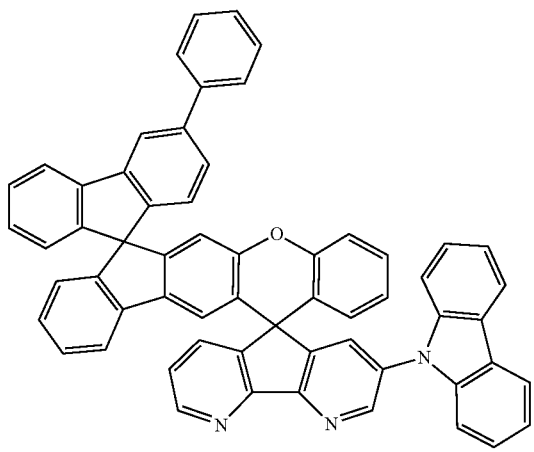
P193
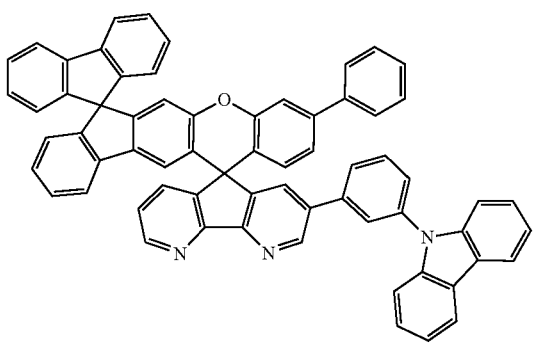
P194
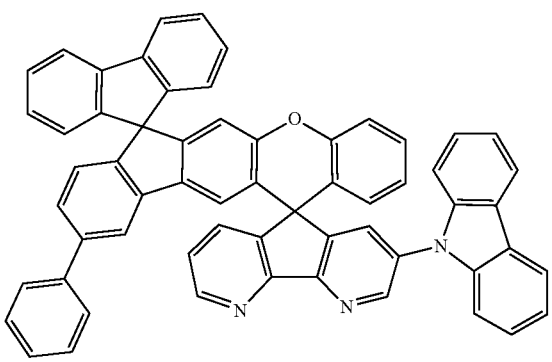
P195
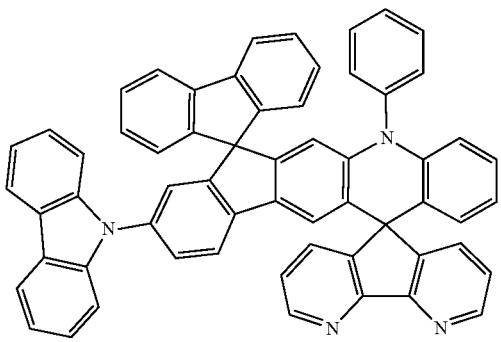
P194
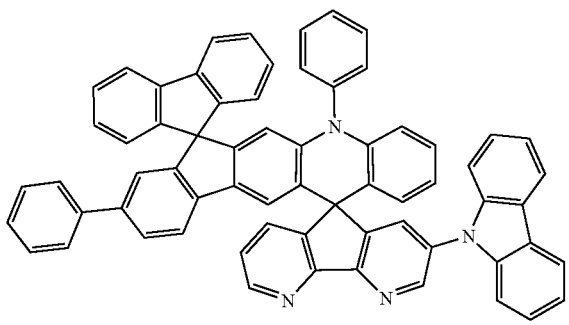
P197
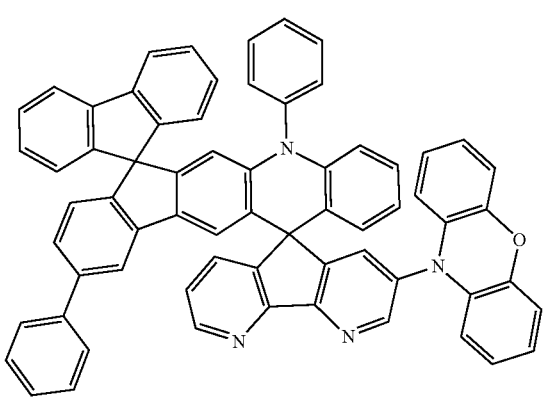
P198
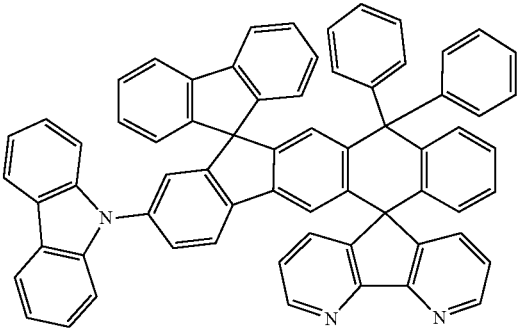
P199
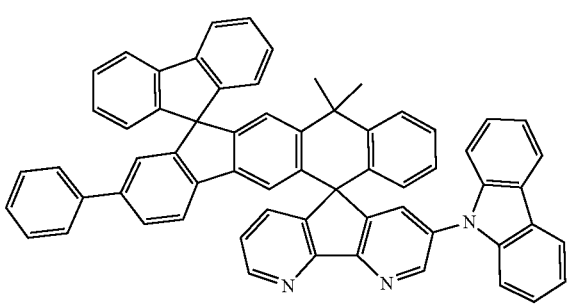

P200
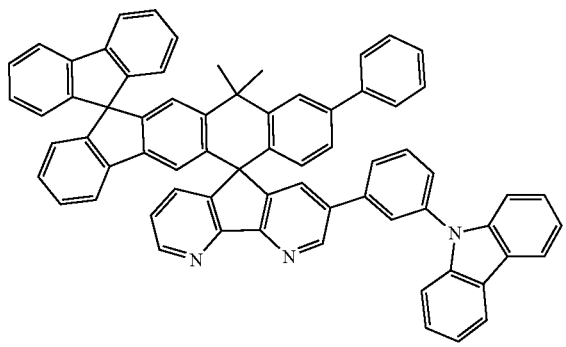
P201
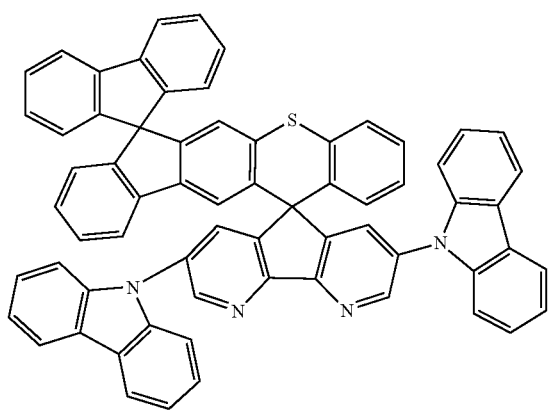
P202
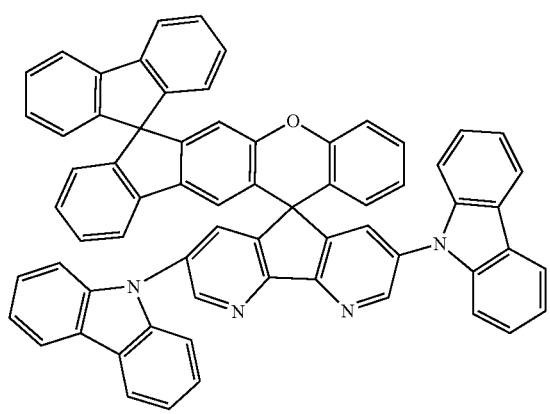
P203
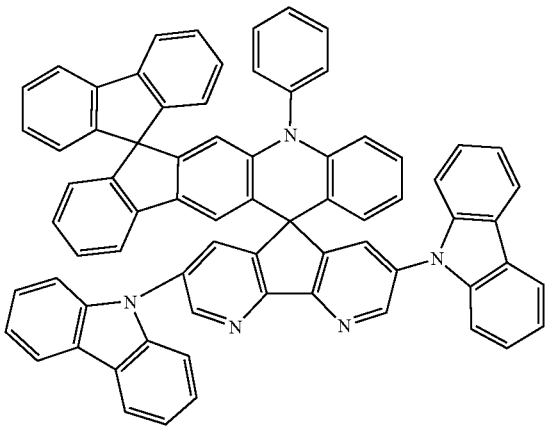
P204
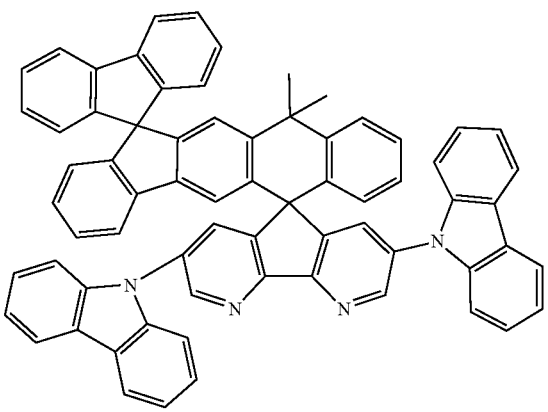
P205
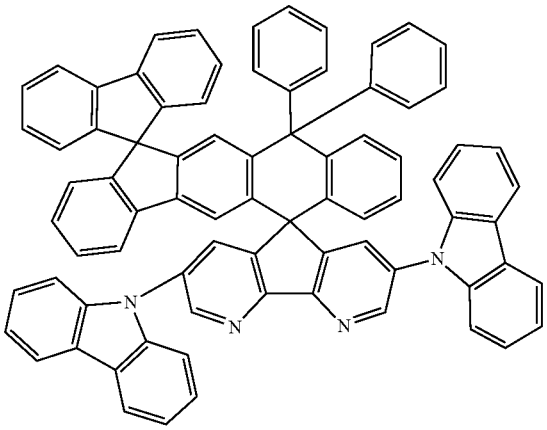

P206
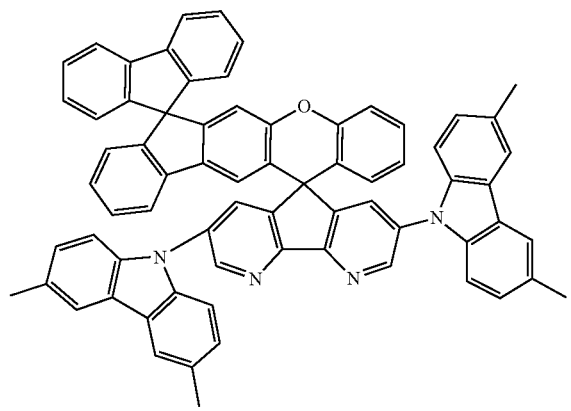
P207
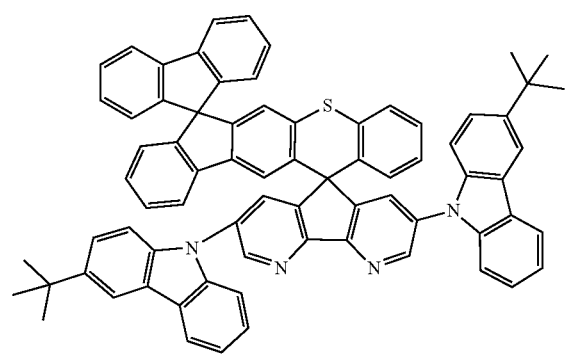
P208
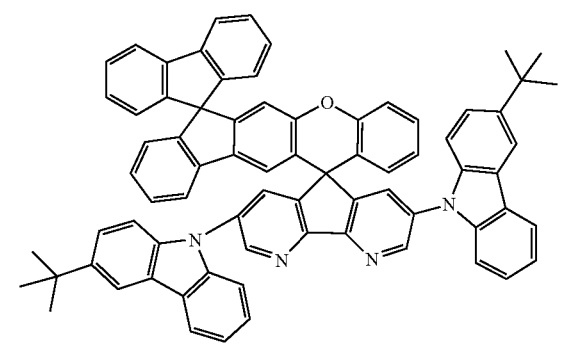
P209
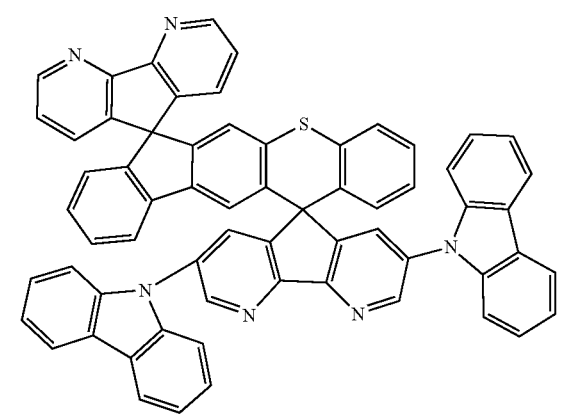
P210
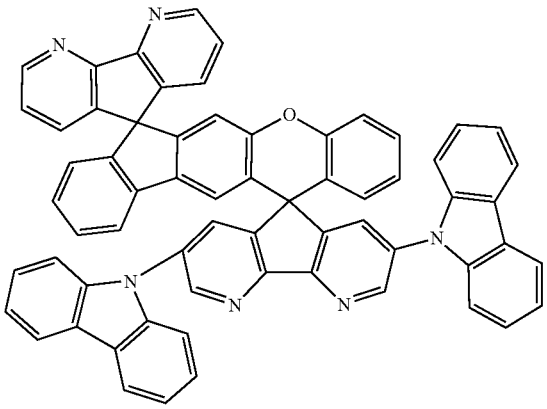
P211
P212

-continued
P213
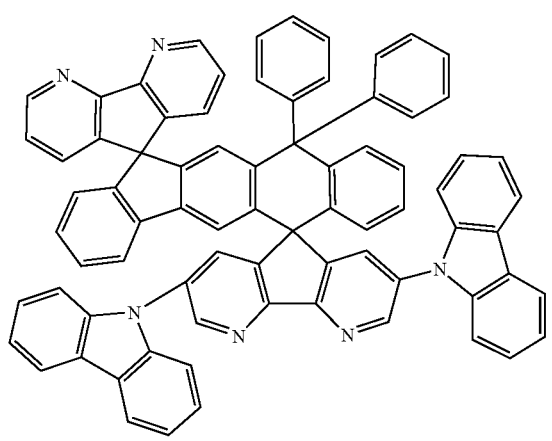
P214
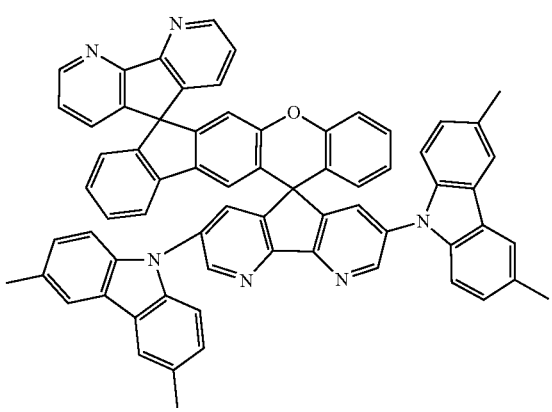
P215
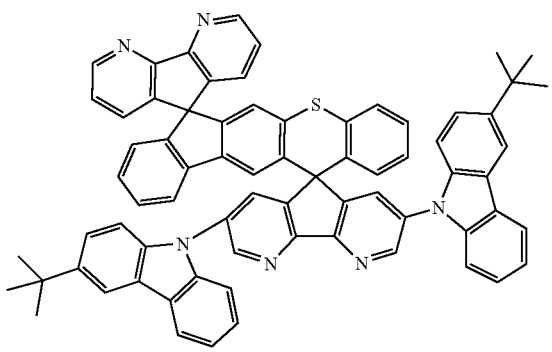
P216
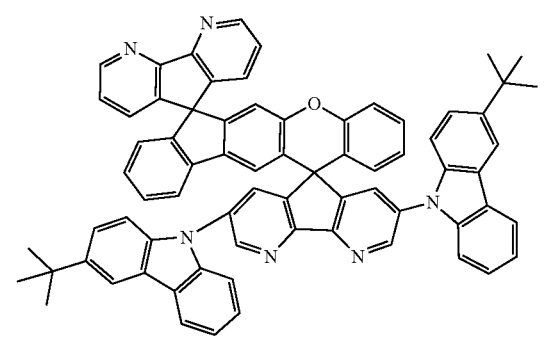
-continued
P217
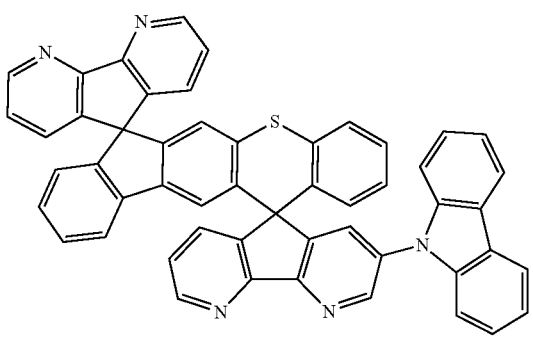
P218
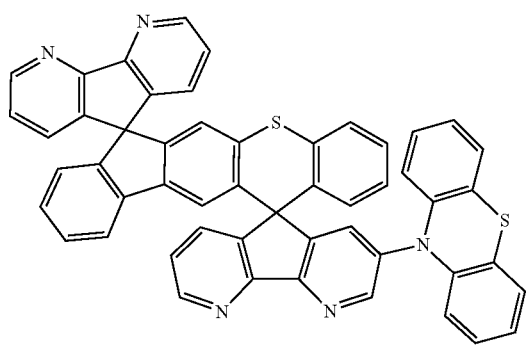
P219
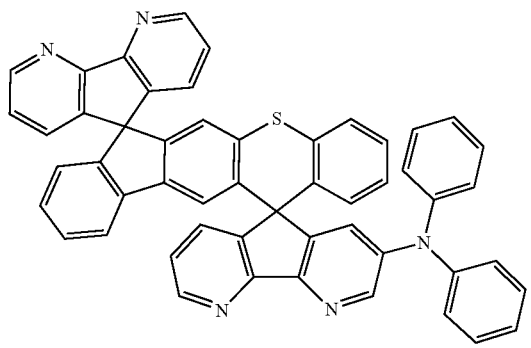
P220
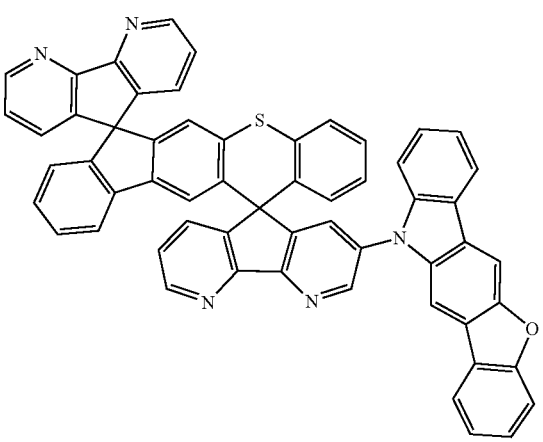

-continued
P221
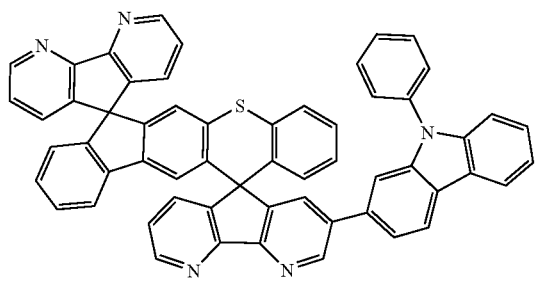
P222
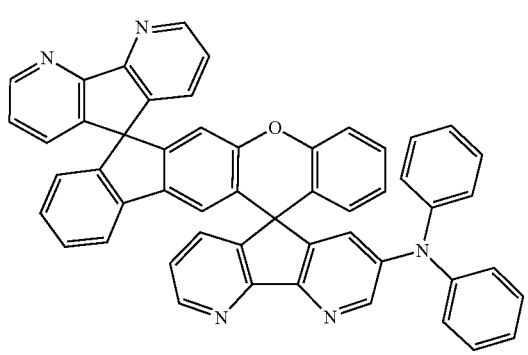
P223
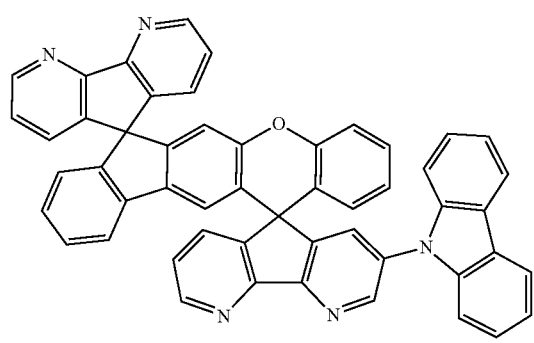
P224
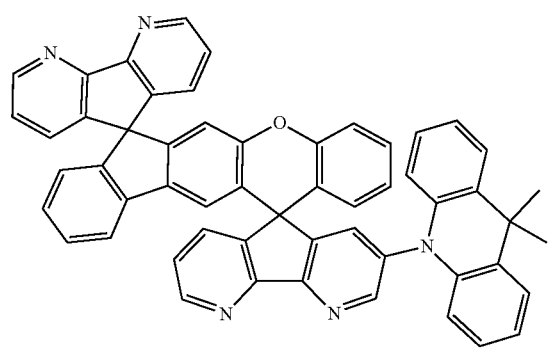
-continued
P225
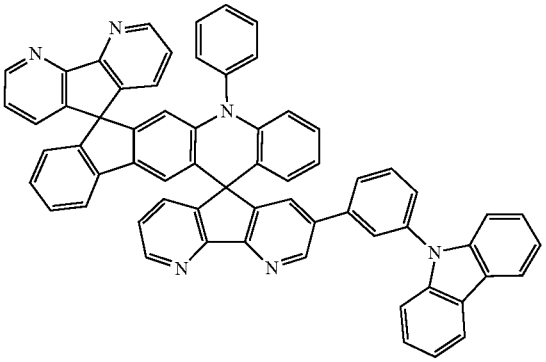
P226
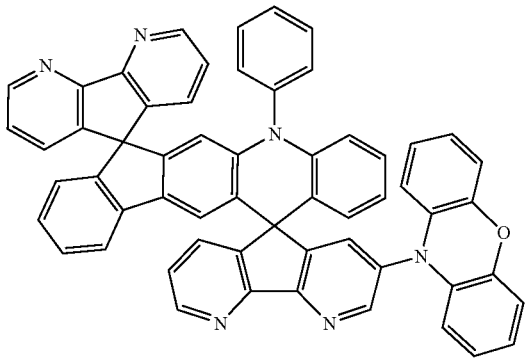
P227
P228
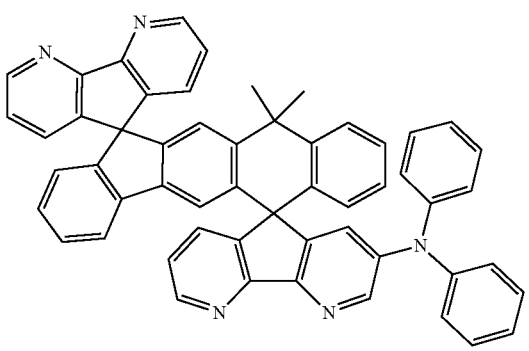

P229
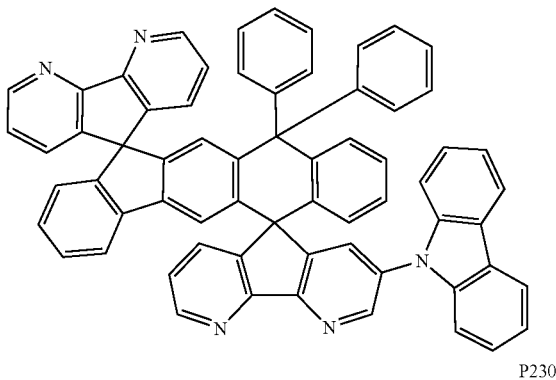
P230
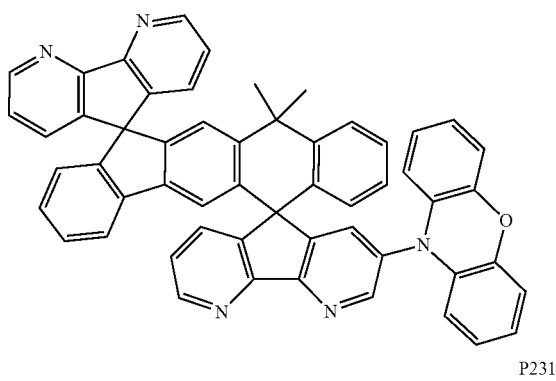
P231
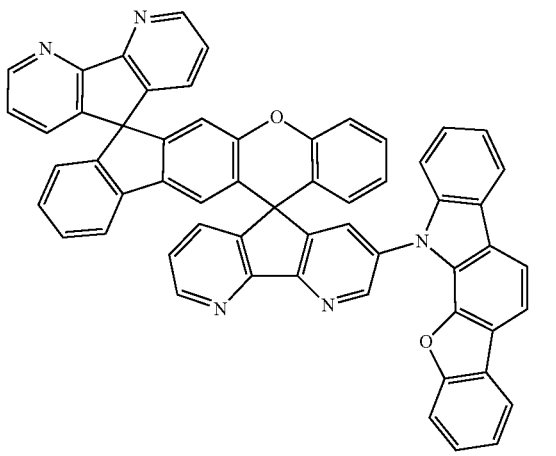
P232
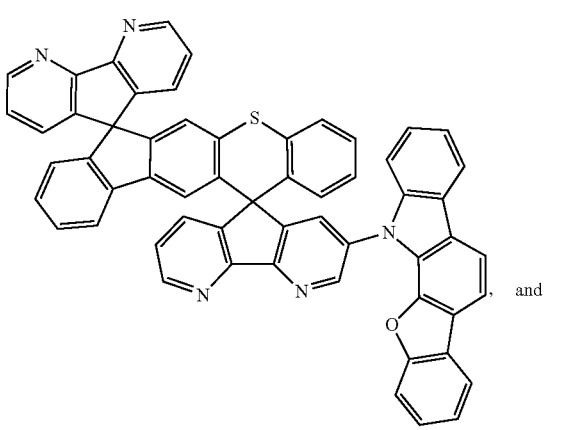
and
P233
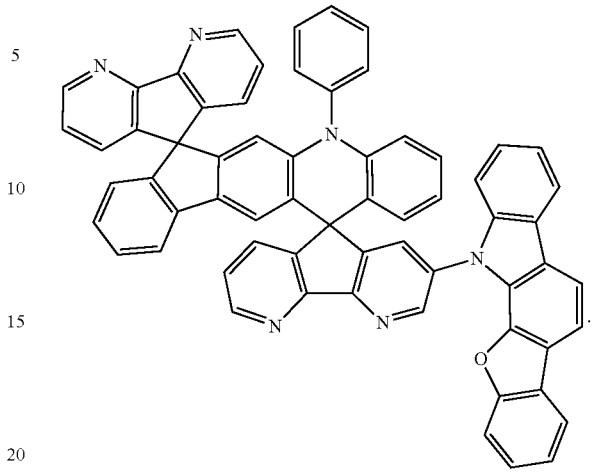
The organic compound having the structure represented by Formula I in the present disclosure is exemplarily prepared according to the following synthesis route:
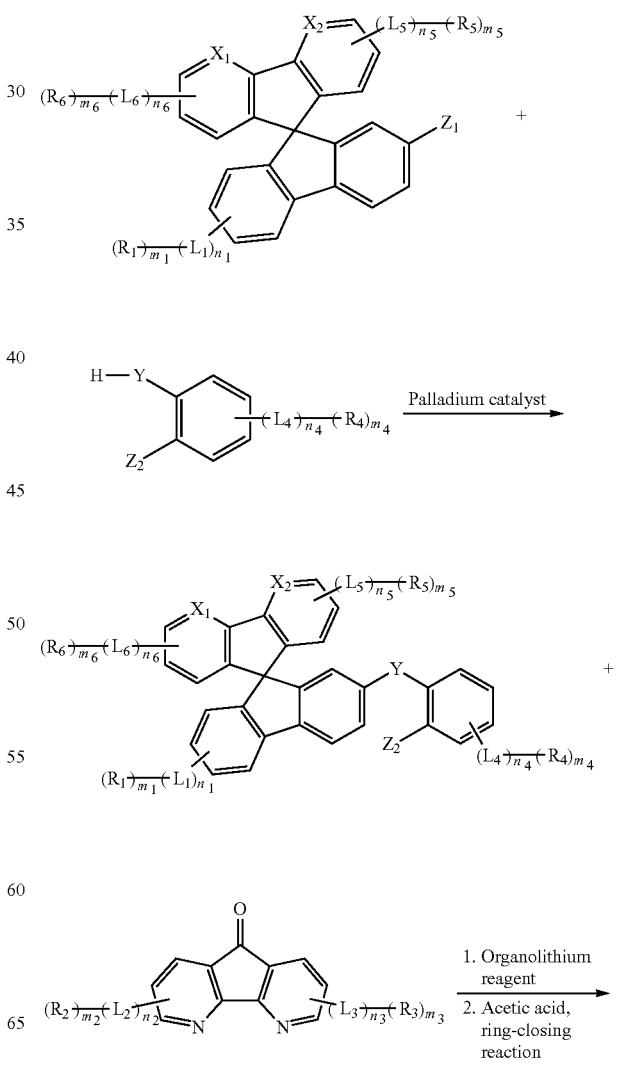

-continued

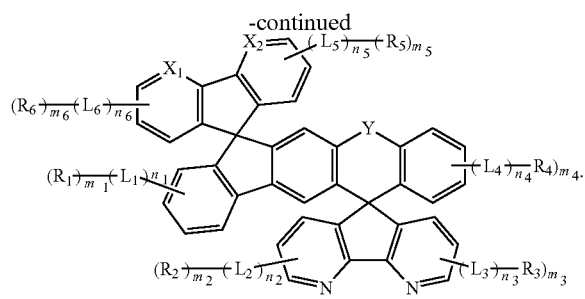

In the above synthesis route, $X_1$, $X_2$, Y, $L_1$ to $L_6$, $R_1$ to $R_6$, $n_1$ to $n_6$, and $m_1$ to $m_6$ are each independently have the same range as defined in Formula I, and $Z_1$ and $Z_2$ are each independently selected from halogen (e.g., fluorine, chlorine, bromine, or iodine).

A second object of the present disclosure is to provide an electroluminescent material including the organic compound as described in the first object.

A third object of the present disclosure is to provide a display panel including an OLED device. The OLED device includes an anode, a cathode, and an organic thin film layer between the anode and the cathode, and a material of the organic thin film layer includes the electroluminescent material as described in the second object.

In an embodiment, the organic thin film layer includes a light emitting layer, the material of which includes the electroluminescent material as described in the second object.

In an embodiment, the electroluminescent material is used as a phosphorescent host material of the light emitting layer.

In an embodiment, the organic thin film layer includes a hole blocking layer, the material of which includes the electroluminescent material as described in the second object.

In an embodiment, the organic thin film layer includes an electron blocking layer, the material of which includes the electroluminescent material as described in the second object.

In an embodiment, the organic thin film layer further includes any one selected from the group consisting of a hole transport layer, a hole injection layer, an electron transport layer, an electron injection layer, and a combination of at least two selected therefrom.

In the OLED device of the present disclosure, a material of the anode may be a metal, a metal oxide, or a conductive polymer, where the metal includes copper, gold, silver, iron, chromium, nickel, manganese, palladium, platinum, and the like as well as alloys thereof, the metal oxide includes indium tin oxide (ITO), indium zinc oxide (IZO), zinc oxide, indium gallium zinc oxide (IGZO), and the like, and the conductive polymer includes polyaniline, polypyrrole, poly(3-methylthiophene) and the like. In addition to the above materials that facilitate hole injection and combinations thereof, the material of the anode further includes known materials suitable to prepare the anode.

In the OLED device, a material of the cathode may be a metal or a multilayer metal material, where the metal includes aluminum, magnesium, silver, indium, tin, titanium and the like as well as alloys thereof, and the multilayer metal material includes LiF/Al, $LiO_2/Al$, $BaF_2/Al$ and the like. In addition to the above materials that facilitate electron injection and combinations thereof, the material of the cathode further includes known materials suitable to prepare the cathode.

In the OLED device, the organic thin film layer includes at least one light emitting layer (EML) and any one selected from the group consisting of a hole transport layer (HTL), a hole injection layer (HIL), an electron blocking layer (EBL), a hole blocking layer (HBL), an electron transport layer (ETL), an electron injection layer (EIL) which is(are) disposed on two sides of the at least one light emitting layer, and a combination of at least two selected therefrom. The hole/electron injection and transport layers may be carbazole compounds, arylamine compounds, benzimidazole compounds, metal compounds, etc. The OLED device may further be provided with a capping layer (CPL) disposed on the cathode (a side of the cathode facing away from the anode).

As shown in the FIGURE which is a schematic view of the OLED device, the OLED device includes an anode 101, a cathode 102, and a light emitting layer 103 between the anode 101 and the cathode 102. A first organic thin film layer 104 and a second organic thin film layer 105 are disposed on two sides of the light emitting layer 103. The first organic thin film layer 104 includes any one selected from the group consisting of a hole transport layer (HTL), a hole injection layer (HIL), an electron blocking layer (EBL), and a combination of at least two selected therefrom and the second organic thin film layer 105 includes any one selected from the group consisting of an electron transport layer (ETL), a hole blocking layer (HBL), an electron injection layer (EIL), and a combination of at least two selected therefrom. A capping layer (CPL) may further be disposed on the cathode 102 (a side of the cathode 102 facing away from 105).

The OLED device may be prepared by the following method: forming the anode on a transparent or opaque smooth substrate, forming the organic thin film layer on the anode, and forming the cathode on the organic thin film layer. The organic thin film layer may be formed by using known film forming methods such as evaporation, sputtering, spin coating, impregnation, and ion plating.

A fourth object of the present disclosure is to provide an electronic device including the display panel as described in the third object.

Preparation examples of the organic compound of the present disclosure are described below for purposes of example.

Preparation Example 1

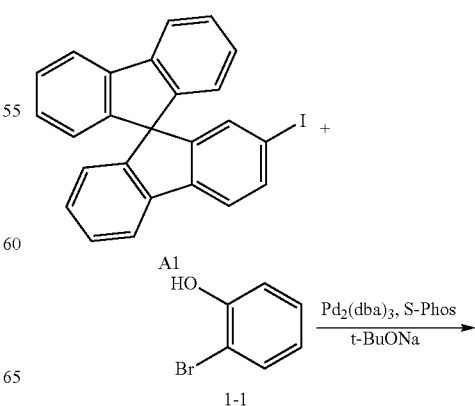

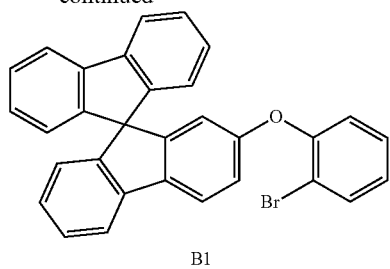

B1

Under nitrogen atmosphere, approximately 100 mL of anhydrous toluene was added to a 250 mL reaction flask, then reactant A1 (4 mmol), reactant 1-1 (4 mmol), sodium t-butoxide (t-BuONa, 10 mmol), palladium catalyst $Pd_2(dba)_3$ (0.2 mmol), and ligand 2-dicyclohexylphosphine-2',6'-dimethoxybiphenyl (S-Phos, 0.6 mmol) were sequentially added to the reaction flask, and the reaction was warmed to 110° C. and kept overnight. After completion of the reaction, the reaction mixture was cooled to room temperature. Dichloromethane (DCM)/$H_2O$ were added to extract the reaction mixture, and the collected organic phase was dried with anhydrous $Na_2SO_4$. The filtrate was collected by suction filtration, the solvent was removed through rotary evaporation, and the residue was purified by column chromatography to obtain an intermediate B1 (with a yield of 83%).

Characterization results of the intermediate B1 are as follows: the following was obtained through matrix-assisted laser desorption/ionization time-of-flight mass spectrometry (MALDI-TOF-MS) (m/z): $C_{31}H_{19}BrO$, whose calculated value was 486.06 and measured value was 486.27.

The intermediates B2 and B3 were prepared according to the above synthesis route, and the raw materials, products and test results are shown in Table 1.

TABLE 1

| Raw material 1 | Raw material 2 | Product | Yield % | MALDI-TOF MS (m/z) characterization |
|---|---|---|---|---|
| A1 | 1-2 | B2 | 80 | $C_{31}H_{19}BrS$ Calculated value: 502.04 Measured value: 502.26 |
| A1 | 1-3 | B3 | 78 | $C_{37}H_{24}BrN$ Calculated value: 561.11 Measured value: 561.24 |

Preparation Example 2

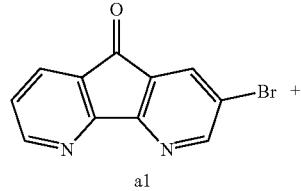

a1

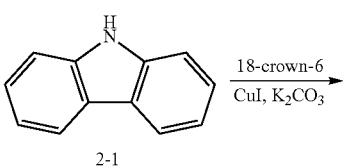

2-1

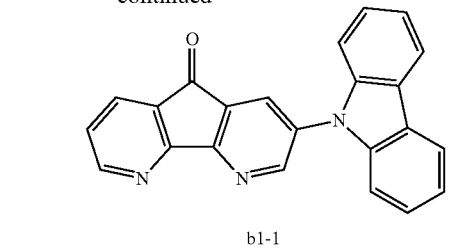

b1-1

Under nitrogen atmosphere, the solvent 1,2-dichlorobenzene was added to a reaction flask, then reactant a1 (6 mmol), reactant 2-1 (7 mmol), potassium carbonate (12 mmol), catalyst CuI (0.6 mmol), and ligand 18-crown-6 (0.6 mmol) were sequentially added to the reaction flask, and the reaction was warmed to 180° C. for 24 h. After completion of the reaction, the reaction mixture was cooled to room temperature. The organic phase was collected by suction filtration, then extracted with DCM/H$_2$O, and dried with anhydrous Na$_2$SO$_4$. The filtrate was collected by suction filtration, the solvent was removed through rotary evaporation, and the residue was purified by column chromatography to obtain an intermediate b1-1 (with a yield of 71%).

Characterization results of the intermediate b1-1 are as follows: the following was obtained through matrix-assisted laser desorption/ionization time-of-flight mass spectrometry (MALDI-TOF-MS) (m/z): C$_{23}$H$_{13}$N$_3$O, whose calculated value was 347.11 and measured value was 347.30.

The intermediates b1-2, b1-3, b1-4, and b1-5 were prepared according to the above synthesis route, and the raw materials, products and test results are shown in Table 2.

TABLE 2

| Raw material 1 | Raw material 2 | Product | Yield % | MALDI-TOF MS (m/z) characterization |
|---|---|---|---|---|
| a1 | 2-2 | b1-2 | 67 | C$_{35}$H$_{20}$N$_4$O<br>Calculated value: 512.16<br>Measured value: 512.35 |
| a1 | 2-3 | b1-3 | 71 | C$_{23}$H$_{15}$N$_3$O<br>Calculated value: 349.12<br>Measured value: 349.33 |

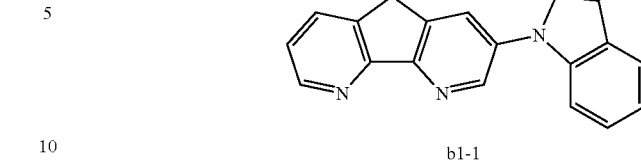

TABLE 2-continued

| Raw material 1 | Raw material 2 | Product | Yield % | MALDI-TOF MS (m/z) characterization |
|---|---|---|---|---|
| a1 | 2-4 | b1-4 | 69 | $C_{23}H_{13}N_3O_2$ Calculated value: 363.10 Measured value: 363.32 |
| a1 | 2-5 | b1-5 | 68 | $C_{29}H_{15}N_3O_2$ Calculated value: 437.12 Measured value: 437.30 |

Preparation Example 3

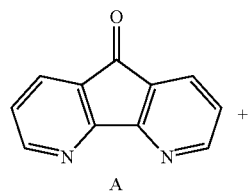

A

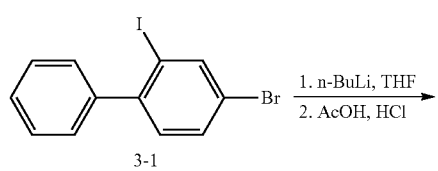

3-1

1. n-BuLi, THF
2. AcOH, HCl

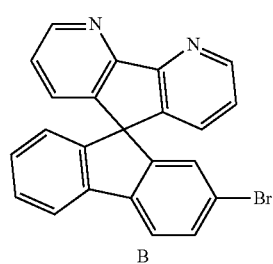

B (1)

Under nitrogen atmosphere, reactant 3-1 (3 mmol) was added to anhydrous tetrahydrofuran (THF) and stirred at −78° C. to cool the reaction solution. Then 1.6 M of n-butyl lithium (n-BuLi, 3 mmol) was added dropwise, and the reaction was kept at −78° C. for 2 h. Reactant A (3 mmol) was slowly added dropwise to the low-temperature reaction solution. After completion of the dropwise addition, the reaction was continued at low temperature for 2 h, and then warmed to room temperature and kept overnight. After completion of the reaction, a small amount of water was added to quench the reaction, and DCM/$H_2O$ were added for extraction. The organic phase was collected and dried with anhydrous $Na_2SO_4$. The filtrate was collected by suction filtration, and the solvent was removed through rotary evaporation to obtain the crude product.

Under nitrogen condition, the above crude product was added to 20 mL of acetic acid, stirred, heated and reacted at 120° C. for 2 h. Then 2 mL of hydrochloric acid was added, and the reaction was heated at this temperature for 12 h. After completion of the reaction, the reaction solution was cooled and extracted. The organic phase was collected, the solvent was removed through rotary evaporation, and the residue was purified by column chromatography to obtain an intermediate B (with a yield of 71%).

Characterization results of the intermediate B are as follows: the following was obtained through matrix-assisted laser desorption/ionization time-of-flight mass spectrometry (MALDI-TOF-MS) (m/z): $C_{23}H_{13}BrN_2$, whose calculated value was 396.03 and measured value was 396.24.

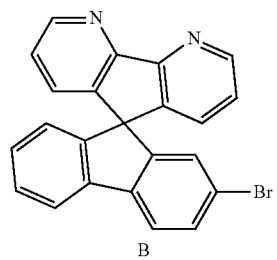

B

+

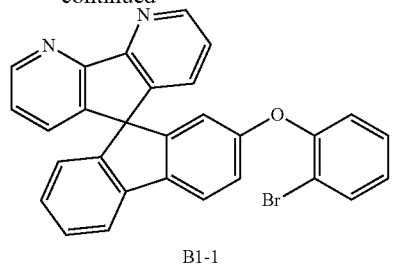

B1-1

The reactant A1 in Preparation example 1 was replaced by equimolar amounts of intermediate B while the raw materials and reaction steps were the same as in Preparation example 1 to obtain an intermediate B1-1 (with a yield of 72%).

Characterization results of the intermediate B1-1 are as follows: the following was obtained through matrix-assisted laser desorption/ionization time-of-flight mass spectrometry (MALDI-TOF-MS) (m/z): $C_{29}H_{17}BrN_2O$, whose calculated value was 488.05 and measured value was 488.26.

The intermediates B1-2 and B1-3 were prepared according to the above synthesis route, and the raw materials, products and test results are shown in Table 3.

TABLE 3

| Raw material 1 | Raw material 2 | Product | Yield % | MALDI-TOF MS (m/z) characterization |
|---|---|---|---|---|
| B | 1-2 (HS-phenyl-Br) | B1-2 | 70 | $C_{29}H_{17}BrN_2S$ Calculated value: 504.03 Measured value: 504.25 |
| B | 1-3 (HN(Ph)-phenyl-Br) | B1-3 | 68 | $C_{35}H_{22}BrN_3$ Calculated value: 563.10 Measured value: 563.31 |

Preparation Example 4

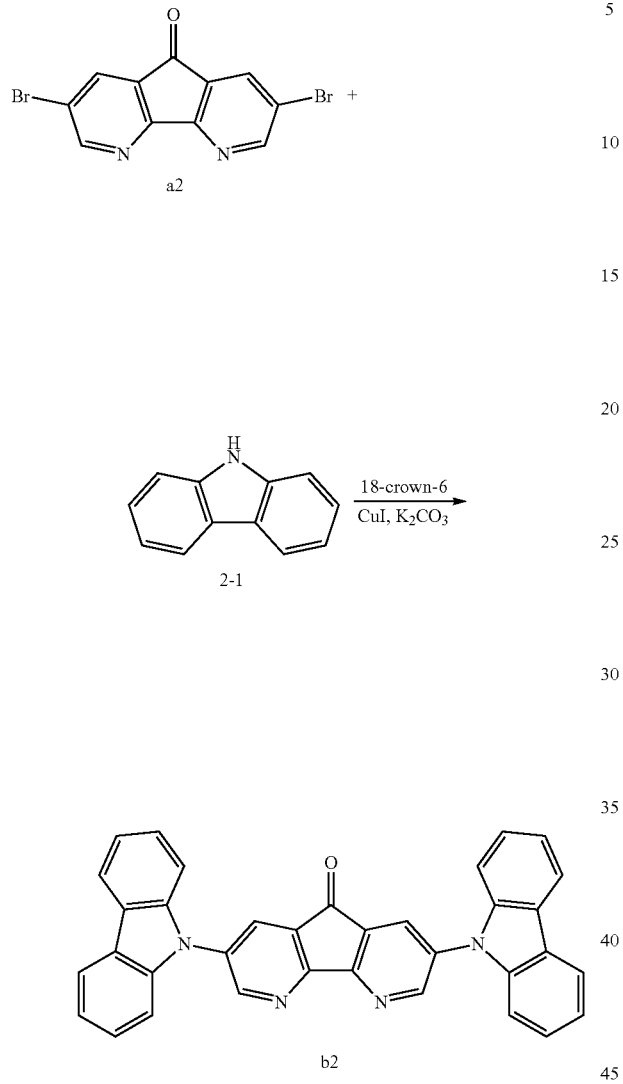

Under nitrogen atmosphere, the solvent 1,2-dichlorobenzene was added to a reaction flask, then reactant a2 (3 mmol), reactant 2-1 (7 mmol), potassium carbonate (6 mmol), catalyst CuI (0.6 mmol), and ligand 18-crown-6 (0.6 mmol) were sequentially added to the reaction flask, and the reaction was warmed to 180° C. for 24 h. After completion of the reaction, the reaction mixture was cooled to room temperature. The organic phase was collected by suction filtration, then extracted with DCM/H$_2$O, and dried with anhydrous Na$_2$SO$_4$. The filtrate was collected by suction filtration, the solvent was removed through rotary evaporation, and the residue was purified by column chromatography to obtain an intermediate b2 (with a yield of 70%).

Characterization results of the intermediate b2 are as follows: the following was obtained through matrix-assisted laser desorption/ionization time-of-flight mass spectrometry (MALDI-TOF-MS) (m/z): C$_{35}$H$_{20}$N$_4$O, whose calculated value was 512.16 and measured value was 512.35.

Example 1

An organic compound P614 was provided, and its structure was as follows:

The preparation method for the organic compound P61 includes steps described below.

Under nitrogen atmosphere, the intermediate B1 (1 mmol) was added to anhydrous THF and stirred at −78° C. to cool the reaction solution. Then 1.6 M of n-BuLi (1.1 mmol) was added dropwise, and the reaction was kept at −78° C. for 2 h. The intermediate b1-1 (1.2 mmol) was slowly added dropwise to the low-temperature reaction solution. After completion of the dropwise addition, the reaction was continued at low temperature for 2 h, and then warmed to room temperature and kept overnight. After completion of the reaction, a small amount of water was added to quench the reaction, and DCM/H$_2$O were added for extraction. The organic phase was collected and dried with anhydrous Na$_2$SO$_4$. The filtrate was collected by suction filtration, and the solvent was removed through rotary evaporation to obtain the crude product.

Under nitrogen condition, the above crude product was added to 20 mL of acetic acid, stirred, heated and reacted at 120° C. for 2 h. Then 2 mL of hydrochloric acid was added, and the reaction was heated at this temperature for 12 h. After completion of the reaction, the reaction solution was cooled and extracted. The organic phase was collected, the solvent was removed through rotary evaporation, and the residue was purified by column chromatography to obtain the target product P61 (with a yield of 67%).

Characterization results of the organic compound P61 are as follows: the following was obtained through matrix-assisted laser desorption/ionization time-of-flight mass spectrometry (MALDI-TOF-MS) (m/z): C$_{54}$H$_{31}$N$_3$O, whose calculated value was 737.25 and measured value was 737.43.

Results of the elemental analysis of the compound are as follows: calculated value (%) was C 87.90, H 4.23, N 5.69, and the measured value was C 87.91, H 4.22, N 5.70.

Examples 2 to 6

An organic compound was provided in each example, which is P80, P104, P109, P1, and P121, respectively. These organic compounds were prepared according to the synthesis route described in Example 1, and the raw materials, products and test results are shown in Table 4.

TABLE 4

| Raw material 1 | Raw material 2 | Product | Yield (%) | (1) MALDI-TOF MS (m/z) characterization; (2) Elemental analysis (%) |
|---|---|---|---|---|
| B1 | b1-2 | 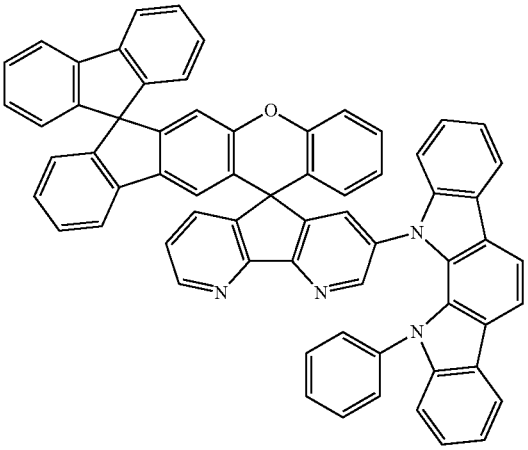<br>P80 | 65 | C$_{66}$H$_{38}$N$_4$O<br>(1) Calculated value: 902.30<br>Measured value: 902.51;<br>(2) Calculated value: C 87.78, H 4.24, N 6.20<br>Measured value: C 87.77, H 4.23, N 6.22 |
| B1 | b1-3 | 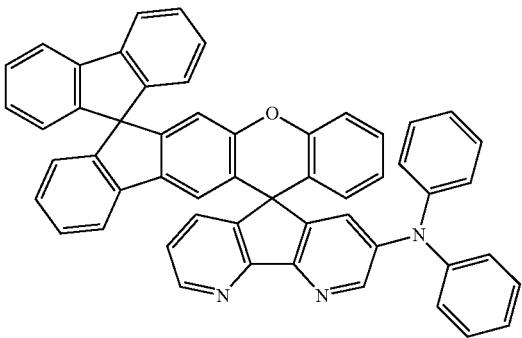<br>P104 | 68 | C$_{54}$H$_{33}$N$_3$O<br>(1) Calculated value: 739.26<br>Measured value: 739.47;<br>(2) Calculated value: C 87.66, H 4.50, N 5.68<br>Measured value: C 87.65, H 4.49, N 5.69 |

TABLE 4-continued

| Raw material 1 | Raw material 2 | Product | Yield (%) | (1) MALDI-TOF MS (m/z) characterization; (2) Elemental analysis (%) |
|---|---|---|---|---|
| B1 | b1-4 | P109 | 66 | C₅₄H₃₁N₃O₂ (1) Calculated value: 753.24 Measured value: 753.45 (2) Calculated value: C 86.04, H 4.14, N 5.57 Measured value: C 86.03, H 4.13, N 5.58 |
| B2 | b1-1 | P1 | 69 | C₅₄H₃₁N₃S (1) Calculated value: 753.22 Measured value: 753.42; (2) Calculated value: C 86.03, H 4.14, N 5.57 Measured value: C 86.02, H 4.13, N 5.58 |
| B3 | b1-1 | P121 | 65 | C₆₀H₃₆N₄ (1) Calculated value: 812.29 Measured value: 812.50; (2) Calculated value: C 88.64, H 4.46, N 6.89 Measured value: C 88.63, H 4.45, N 6.91 |

Example 7

An organic compound P223 was provided, and its structure was as follows:

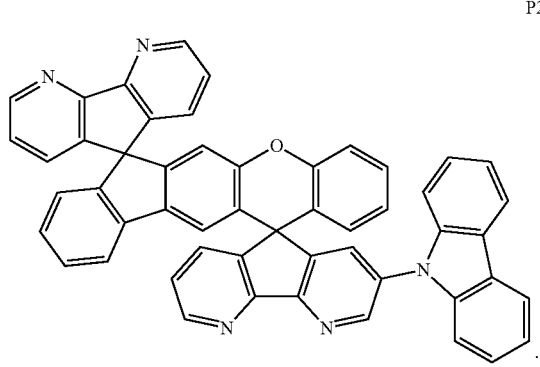

P223

The preparation method for the organic compound P223 includes steps described below.

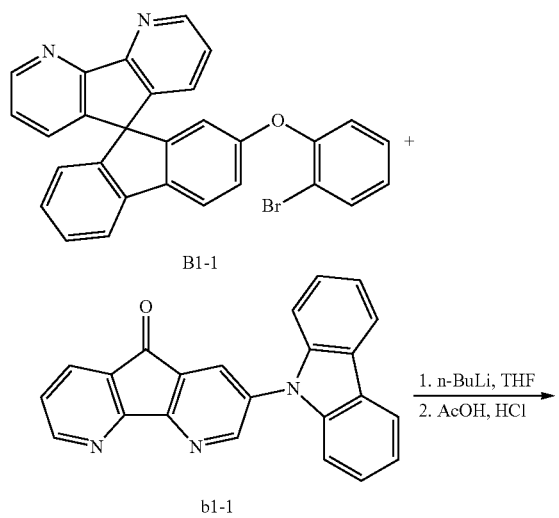

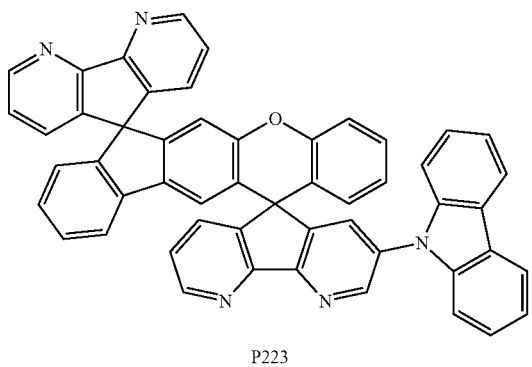 [SMILES: c1ccc2c(c1)Sc1cc3c(cc1C21c2cccnc2-c2ncc(-n4c5ccccc5c5ccccc54)cc21)-c1ccccc1C31c2ccccc2-c2ccccc21 ; "P1"]

P223

The intermediate B1 in Example 1 was replaced by equimolar amounts of intermediate B1-1 while the raw materials and reaction steps were the same as in Example 1 to obtain the target product P223 (with a yield of 69%).

Characterization results of the organic compound P223 are as follows: the following was obtained through matrix-assisted laser desorption/ionization time-of-flight mass spectrometry (MALDI-TOF-MS) (m/z): $C_{52}H_{29}N_5O$, whose calculated value was 739.24 and measured value was 739.45.

Results of the elemental analysis of the compound are as follows: calculated value (%) was C 84.42, H 3.95, N 9.47, and the measured value was C 84.41, H 3.94, N 9.49.

Examples 8 to 10

An organic compound was provided in each example, which is P231, P232, and P233, respectively. These organic compounds were prepared according to the synthesis route described in Example 7, and the raw materials, products and test results are shown in Table 5.

TABLE 5

| Raw material 1 | Raw material 2 | Product | Yield (%) | (1) MALDI-TOF MS (m/z) characterization; (2) Elemental analysis (%) |
|---|---|---|---|---|
| B1-1 | b1-5 | P231 | 67 | $C_{58}H_{31}N_5O_2$ (1) Calculated value: 829.25 Measured value: 829.45; (2) Calculated value: C 83.94, H 3.77, N 8.44 Measured value: C 83.93, H 3.76, N 8.46 |

TABLE 5-continued
| Raw material 1 | Raw material 2 | Product | Yield (%) | (1) MALDI-TOF MS (m/z) characterization; (2) Elemental analysis (%) |
|---|---|---|---|---|
| B1-2 | b1-5 | 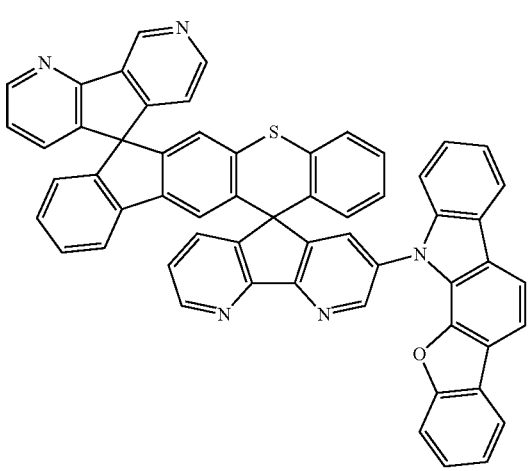<br>P232 | 66 | $C_{58}H_{31}N_5OS$<br>(1) Calculated value: 845.22<br>Measured value: 845.43;<br>(2) Calculated value: C 82.35, H 3.69, N 8.28<br>Measured value: C 82.34, H 3.68, N 8.30 |
| B1-3 | b1-5 | 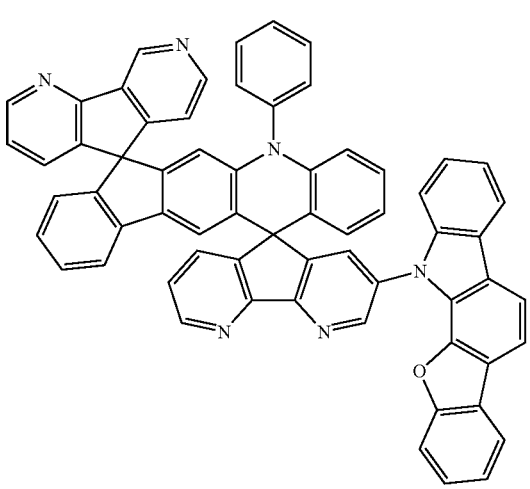<br>P233 | 65 | $C_{64}H_{36}N_6O$<br>(1) Calculated value: 904.30<br>Measured value: 904.52;<br>(2) Calculated value: C 84.94, H 4.01, N 9.29<br>Measured value: C 84.93, H 4.00, N 9.31 |

Example 11

An organic compound P202 was provided, and its structure was as follows:

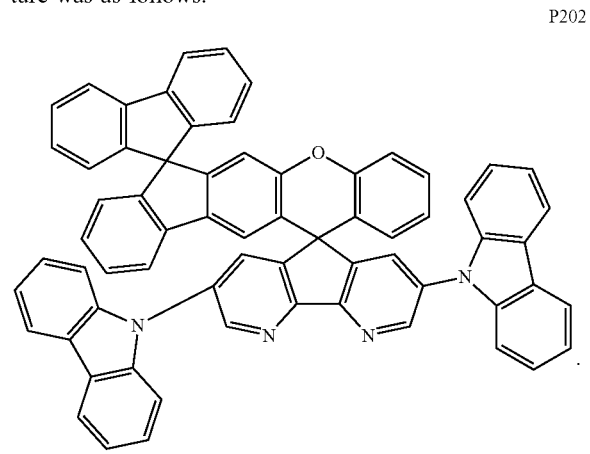

P202

The preparation method for the organic compound P202 includes steps described below.

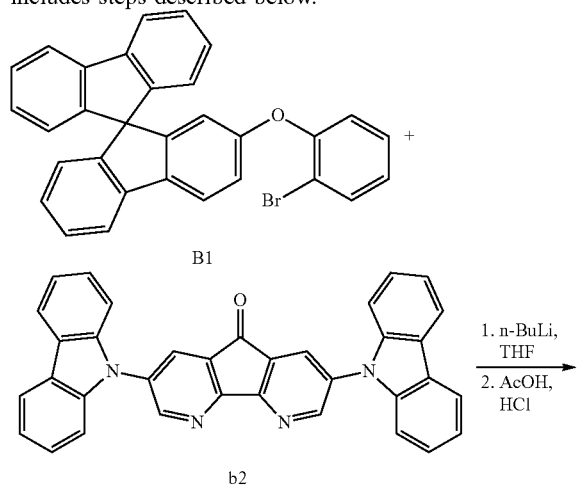

The intermediate b1-1 in Example 1 was replaced by equimolar amounts of intermediate b2 while the raw materials and reaction steps were the same as in Example 1 to obtain the target product P202 (with a yield of 61%).

Characterization results of the organic compound P202 are as follows: the following was obtained through matrix-assisted laser desorption/ionization time-of-flight mass spectrometry (MALDI-TOF-MS) (m/z): $C_{66}H_{38}N_4O$, whose calculated value was 902.30 and measured value was 902.51.

Results of the elemental analysis of the compound are as follows: calculated value (%) was C 87.78, H 4.24, N 6.20, and the measured value was C 87.77, H 4.23, N 6.22.

Examples 12 to 14

An organic compound was provided in each example, which is P201, P210, and P209, respectively. These organic compounds were prepared according to the synthesis route described in Example 11, and the raw materials, products and test results are shown in Table 6.

TABLE 6

| Raw material 1 | Raw material 2 | Product | Yield (%) | (1) MALDI-TOF MS (m/z) characterization; (2) Elemental analysis (%) |
|---|---|---|---|---|
| B2 | b2 | 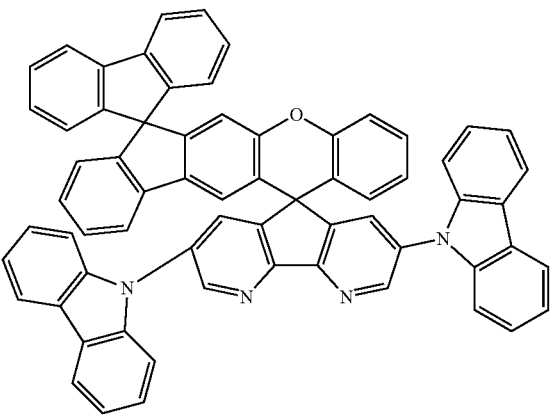 P201 | 62 | $C_{66}H_{38}N_4S$ (1) Calculated value: 918.28 Measured value: 918.50; (2) Calculated value: C 86.25, H 4.17, N 6.10 Measured value: C 86.24, H 4.16, N 6.12 |

TABLE 6-continued

| Raw material 1 | Raw material 2 | Product | Yield (%) | (1) MALDI-TOF MS (m/z) characterization; (2) Elemental analysis (%) |
|---|---|---|---|---|
| B1-1 | b2 | P210 | 65 | $C_{64}H_{36}N_6O$ (1) Calculated value: 904.30 Measured value: 904.51; (2) Calculated value: C 84.94, H 4.01, N 9.29 Measured value: C 84.93, H 4.00, N 9.31 |
| B1-2 | b2 | P209 | 66 | $C_{64}H_{36}N_6S$ (1) Calculated value: 920.27 Measured value: 920.46; (2) Calculated value: C 83.46, H 3.94, N 9.12 Measured value: C 83.45, H 3.93, N 9.14 |

Application examples in which the organic compounds described in the present disclosure are applied to the OLED device are described below for purposes of example.

Application Example 1

An OLED device was provided herein. The OLED device sequentially included a glass substrate having an ITO anode with a thickness of 100 nm, a hole injection layer with a thickness of 10 nm, a hole transport layer with a thickness of 40 nm, an electron blocking layer with a thickness of 10 nm, a light emitting layer with a thickness of 20 nm, a hole blocking layer with a thickness of 10 nm, an electron transport layer with a thickness of 30 nm, an electron injection layer with a thickness of 2 nm, and a cathode (aluminum electrode) with a thickness of 100 nm.

The steps for preparing the OLED device was as follows:
(1) a glass substrate having an ITO anode was sonicated in isopropanol and deionized water for 30 min separately, and exposed to ozone for about 10 min for cleaning, and then the cleaned glass substrate was installed onto a vacuum deposition apparatus;
(2) Compound a was deposited by vacuum evaporation on the ITO anode layer at a vacuum degree of $2 \times 10^{-6}$ Pa as the hole injection layer with a thickness of 10 nm;
(3) Compound b was deposited by vacuum evaporation on the hole injection layer as the hole transport layer with a thickness of 40 nm;
(4) Compound c was deposited by vacuum evaporation on the hole transport layer as the electron blocking layer with a thickness of 10 nm;
(5) Organic compound P61 provided in Example 1 of the present disclosure and a doping material, i.e., Compound d, were co-deposited by vacuum evaporation on the electron blocking layer as the light emitting layer with a thickness of 20 nm;
(6) Compound e was deposited by vacuum evaporation on the light emitting layer as the hole blocking layer with a thickness of 10 nm;
(7) Compound f was deposited by vacuum evaporation on the hole blocking layer as the electron transport layer with a thickness of 30 nm;
(8) LiF was deposited by vacuum evaporation on the electron transport layer as the electron injection layer with a thickness of 2 nm; and
(9) an aluminum electrode was deposited by vacuum evaporation on the electron injection layer as the cathode with a thickness of 100 nm.

The structures of compounds used in the OLED device are as follows:

Compound a

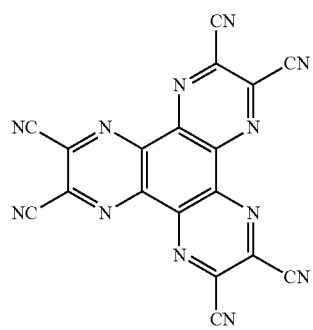

Compound b

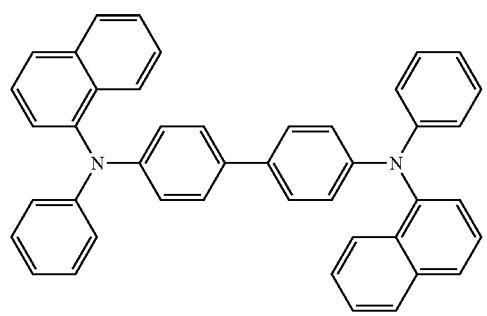

Compound c

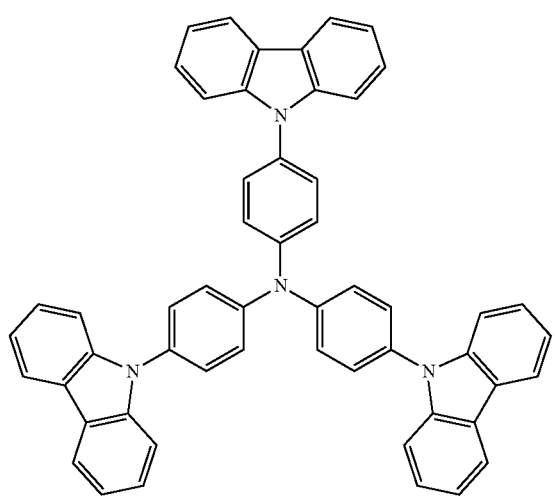

Compound d

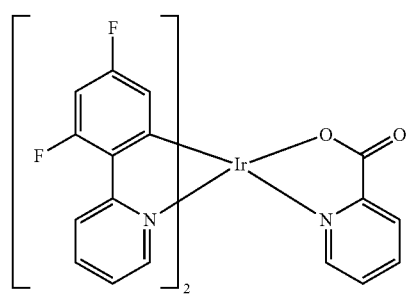

Compound e

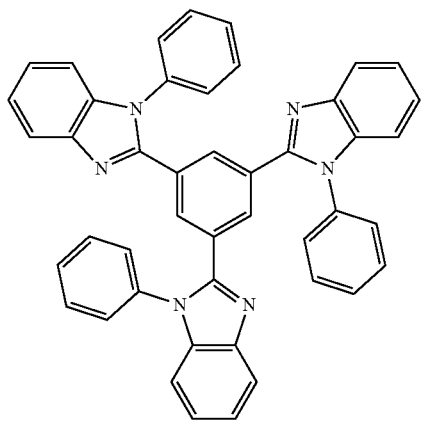

Compound f

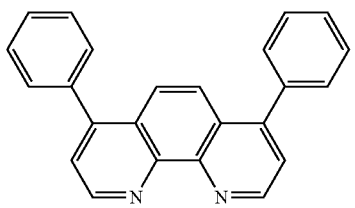

Application Example 2 to 14

An OLED device was provided in each application example. Each of these application examples differs from Application example 1 in that the organic compound P61 in step (5) was replaced with an equal amount of the organic compounds P80, P104, P109, P1, P121, P223, P231, P232, P233, P202, P201, P210, and P209, respectively, while raw materials and preparation steps were the same.

Comparative Example 1

An OLED device was provided herein. This comparative example differs from Application example 1 in that the organic compound P61 in step (5) was replaced with an equal amount of comparative compound 1

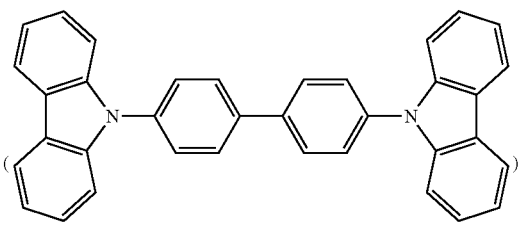 [SMILES: c1ccc2c(c1)c1ccccc1n2-c1ccc(-c2ccc(-n3c4ccccc4c4ccccc43)cc2)cc1]

while raw materials and preparation steps were the same.

Comparative Example 2

An OLED device was provided herein. This comparative example differs from Application example 1 in that the organic compound P61 in step (5) was replaced with an equal amount of comparative compound 2

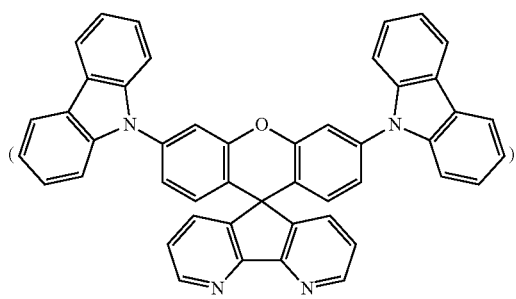 [SMILES: c1cnc2c(c1)C1(c3ccc(-n4c5ccccc5c5ccccc54)cc3Oc3cc(-n4c5ccccc5c5ccccc54)ccc31)c1cccnc1-2]

while raw materials and preparation steps were the same.

Performance Test:

(1) Simulated Calculations of Compounds

By means of a density functional theory (DFT), the distribution and energy levels of molecular frontier orbital HOMO and LUMO were optimized and calculated for the organic compounds provided by the present disclosure using a Guassian 09 package (Guassian Inc.) at a calculation level of B3LYP/6-31G(d). Meanwhile, based on a time-dependent density functional theory (TDDFT), the lowest singlet energy level $E_{S1}$ and the lowest triplet energy level En of molecules of each compound were simulated and calculated. Results are shown in Table 7.

TABLE 7

| Organic compound | HOMO (eV) | LUMO (eV) | $E_g$ (eV) | $E_{S1}$ (eV) | $E_{T1}$ (eV) |
|---|---|---|---|---|---|
| P61 | −5.48 | −1.66 | 3.82 | 3.27 | 2.81 |
| P80 | −5.29 | −1.56 | 3.72 | 3.18 | 2.86 |
| P104 | −5.35 | −1.64 | 3.71 | 3.25 | 2.79 |
| P109 | −5.33 | −1.63 | 3.70 | 3.23 | 2.78 |
| P1 | −5.46 | −1.65 | 3.81 | 3.26 | 2.81 |
| P121 | −5.43 | −1.64 | 3.79 | 3.25 | 2.80 |
| P223 | −5.54 | −1.75 | 3.79 | 3.25 | 2.80 |
| P231 | −5.53 | −1.71 | 3.82 | 3.29 | 2.84 |
| P232 | −5.52 | −1.71 | 3.81 | 3.28 | 2.84 |
| P233 | −5.50 | −1.70 | 3.80 | 3.27 | 2.83 |
| P202 | −5.38 | −1.79 | 3.59 | 3.07 | 2.63 |
| P201 | −5.37 | −1.80 | 3.57 | 3.06 | 2.62 |
| P210 | −5.45 | −1.87 | 3.58 | 3.06 | 2.62 |
| P209 | −5.44 | −1.88 | 3.56 | 3.05 | 2.61 |

It could be seen from data in Table 7 that with the special design of the molecular structure, the organic compound provided by the present disclosure had suitable HOMO/LUMO energy levels (−5.54 to −5.29 eV/−1.88 to −1.56 eV), facilitating the coordination with adjacent layers in terms of energy level, and the organic compound could also cover the energy level of the guest. Meanwhile, the organic compound provided by the present disclosure also had a higher triplet energy level ($E_T \geq 2.61$ eV), and when it was used as the host material of the light emitting layer, it could effectively transfer energy to the guest and prevent the energy backflow from the guest to the host, implementing high light emitting efficiency. The organic compound provided by the present disclosure also has a bis-spiro structure which endows the molecule with a twisted structure, reducing the stacking of molecules, avoiding the crystallinity of the molecule and making the organic compound more stable when applied to the device.

(2) Performance Evaluation of OLED Device

Currents of the OLED device at different voltages were tested by the Keithley 2365A digital nanovoltmeter, and then current densities of the OLED device at different voltages were obtained by dividing each current by the light emitting area. The brightness and radiant energy flux densities of the OLED device at different voltages were tested by the Konicaminolta CS-2000 spectroradiometer. According to the current densities and brightness of the OLED device at different voltages, the working voltage V and current efficiency CE (cd/A) of the OLED device at the same current density (10 mA/cm$^2$) were obtained. A lifetime LT95 (under a testing condition of 50 mA/cm$^2$) was obtained by measuring time when the brightness of the OLED device reached 95% of its initial brightness. Test data is shown in Table 8.

TABLE 8

| OLED device | Light emitting layer host material | V (V) | CE (cd/A) | LT95 (h) |
|---|---|---|---|---|
| Application example 1 | P61 | 4.07 | 15.4 | 68 |
| Application example 2 | P80 | 3.98 | 16.1 | 71 |
| Application example 3 | P104 | 4.06 | 15.0 | 60 |
| Application example 4 | P109 | 4.04 | 15.1 | 62 |
| Application example 5 | P1 | 4.09 | 15.3 | 65 |
| Application example 6 | P121 | 4.08 | 15.2 | 63 |
| Application example 7 | P223 | 4.05 | 15.5 | 69 |
| Application example 8 | P231 | 4.02 | 15.9 | 70 |
| Application example 9 | P232 | 4.04 | 15.6 | 68 |
| Application example 10 | P233 | 4.03 | 15.7 | 67 |
| Application example 11 | P202 | 3.99 | 14.5 | 66 |
| Application example 12 | P201 | 4.01 | 14.4 | 64 |
| Application example 13 | P210 | 3.96 | 14.8 | 68 |
| Application example 14 | P209 | 3.97 | 14.6 | 67 |
| Comparative example 1 | Comparative compound 1 | 4.25 | 13.5 | 52 |
| Comparative example 2 | Comparative compound 2 | 4.19 | 14.0 | 58 |

It could be seen from test data in Table 8, the use of the organic compound provided by the present disclosure as the host material of the light emitting layer of the OLED device could enable the OLED device to have a lower driving voltage, higher light emitting efficiency and longer device lifetime, where the working voltage was less than or equal to 4.09 V, the current efficiency CE was greater than or equal to 14.4 cd/A, and CE of the OLED device corresponding to some of the organic compounds even reached 15 to 16 cd/A, and the lifetime LT95 was greater than or equal to 62 h. Compared with Comparative example 1 (the common phosphorescent host material) and Comparative example 2, the OLED device using the organic compound provided by the present disclosure had reduced working voltage and improved efficiency and lifetime, probably thanks to the fact that the organic compound provided by the present disclosure has suitable energy level, which makes it better matched with the adjacent layers, and has a higher triplet energy level, which can effectively transfer energy to the guest and prevent energy backflow from the guest to the host, effectively improving the light emitting efficiency of the OLED device. In particular, for Application examples 11 to 14, the current efficiencies CE of the OLED devices were less than 15 cd/A, which may be due to the fact that the organic compounds in these examples have lower triplet energy levels than other organic compounds involved in the present disclosure, which makes it fail to efficiently prevent the backflow energy from the guest to the host. Meanwhile, the organic compound provided by the present disclosure fuses two spiro rings to form a bis-spiro structure which makes the molecule twisted, which effectively reduces the stacking of molecules and thus reduces the crystallinity of the molecule, ensuring that the organic compound has excellent thermal stability and thin film stability. Therefore, the OLED device works more stably, facilitating the lifetime improvement of the OLED device.

The applicant has stated that although the organic compound, the electroluminescent material and the application thereof in the present disclosure are described through the examples described above, the present disclosure is not limited to the processes and steps described above, which means that the implementation of the present disclosure does not necessarily depend on the processes and steps described above. Any improvements made to the present disclosure, equivalent replacements of raw materials selected in the present disclosure and addition of adjuvant ingredients thereof, selections of specific methods, etc., all fall within the protection scope and the disclosed scope of the present disclosure.

What is claimed is:

1. An organic compound having a structure represented by Formula I:

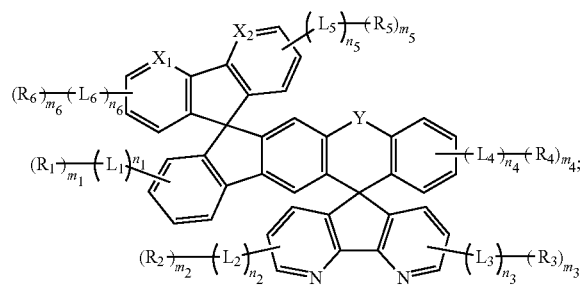

Formula I wherein $X_1$ and $X_2$ are each independently selected from C or N;

Y is any one selected from the group consisting of O, S, N—$R_{N1}$, $CR_{C1}R_{C2}$, O=S=O, $SiR_{S1}R_{S2}$, O=P—$Ar_1$, and S=P—$Ar_2$;

$R_{N1}$, $R_{C1}$, $R_{C2}$, $R_{S1}$, and $R_{S2}$ are each independently any one selected from the group consisting of substituted or unsubstituted C1 to C20 straight or branched chain alkyl, substituted or unsubstituted C6 to C40 aryl, and substituted or unsubstituted C3 to C40 heteroaryl;

$Ar_1$ and $Ar_2$ are each independently any one selected from the group consisting of substituted or unsubstituted C6 to C40 aryl and substituted or unsubstituted C3 to C40 heteroaryl;

$L_1$, $L_2$, $L_3$, $L_4$, $L_5$, and $L_6$ are each independently any one selected from the group consisting of a single bond, substituted or unsubstituted C6 to C40 arylene and substituted or unsubstituted C3 to C40 heteroarylene;

$R_1$, $R_2$, $R_3$, $R_4$, $R_5$, and $R_6$ are each independently any one selected from the group consisting of deuterium, halogen, cyano, substituted or unsubstituted C1 to C20 straight or branched chain alkyl, substituted or unsubstituted C1 to C20 alkoxy, substituted or unsubstituted C1 to C20 alkylthio, substituted or unsubstituted C3 to C20 cycloalkyl, substituted or unsubstituted C6 to C40 aryl, substituted or unsubstituted C6 to C40 arylamine, substituted or unsubstituted C3 to C40 heteroaryl, and substituted or unsubstituted C2 to C40 nonaromatic heterocyclyl;

$n_1$, $n_4$, $n_5$, $n_6$, $m_1$, $m_4$, $m_5$, and $m_6$ are each independently an integer of 0-4; and $n_2$, $n_3$, $m_2$, and $m_3$ are each independently an integer of 0-3.

2. The organic compound according to claim 1, wherein the substituents in the substituted straight or branched chain alkyl, substituted aryl, substituted heteroaryl, substituted arylene, substituted heteroarylene, substituted alkoxy, substituted alkylthio, substituted cycloalkyl, substituted arylamine, and substituted nonaromatic heterocyclyl are each independently at least one selected from the group consisting of deuterium, halogen, cyano, C1 to C10 straight or branched chain alkyl, C1 to C10 alkoxy, C1 to C10 alkylthio, C6 to C20 aryl, C2 to C20 heteroaryl, and C6 to C18 arylamine.

3. The organic compound according to claim 1, wherein Y is any one selected from the group consisting of O, S, N—$R_{N1}$, and $CR_{C1}R_{C2}$.

4. The organic compound according to claim 1, wherein $R_{N1}$, $R_{C1}$, and $R_{C2}$ are each independently any one selected from the group consisting of unsubstituted or $R_{y1}$-substituted C1 to C6 straight or branched chain alkyl, unsubstituted or $R_{y1}$-substituted C6 to C18 aryl, and unsubstituted or $R_{y1}$-substituted C3 to C12 heteroaryl;

wherein $R_{y1}$ is each independently any one selected from the group consisting of deuterium, halogen, cyano, C1 to C6 straight or branched chain alkyl, C1 to C6 alkoxy, C1 to C6 alkylthio, C6 to C12 aryl, C2 to C12 heteroaryl, and C6 to C18 arylamine.

5. The organic compound according to claim 1, wherein $L_1$, $L_2$, $L_3$, $L_4$, $L_5$, and $L_6$ are each independently any one selected from the group consisting of a single bond, phenylene, biphenylene, terphenylene, naphthylene, and C3 to C12 nitrogen-containing heteroarylene.

6. The organic compound according to claim 1, wherein $R_1$, $R_4$, $R_5$, and $R_6$ are each independently any one selected from the group consisting of deuterium, unsubstituted or $R_{y2}$-substituted C1 to C6 straight or branched chain alkyl, unsubstituted or $R_{y2}$-substituted C6 to C18 aryl, unsubstituted or $R_{y2}$-substituted C3 to C18 heteroaryl, unsubstituted or $R_{y2}$-substituted diphenylamino, C1 to C6 alkoxy, and C1 to C6 alkylthio;

wherein $R_{y2}$ is each independently any one selected from the group consisting of deuterium, halogen, cyano, C1 to C6 straight or branched chain alkyl, C1 to C6 alkoxy, C1 to C6 alkylthio, C6 to C12 aryl, C2 to C12 heteroaryl, and C6 to C18 arylamine.

7. The organic compound according to claim 1, wherein $R_2$ and $R_3$ are each independently any one selected from the group consisting of the following groups:

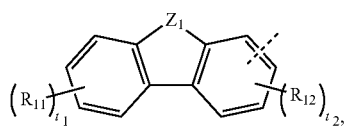

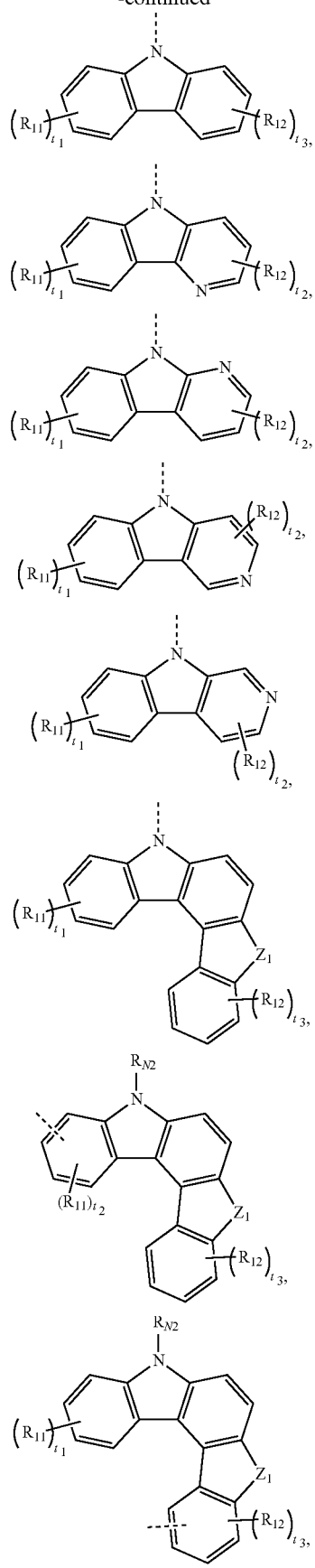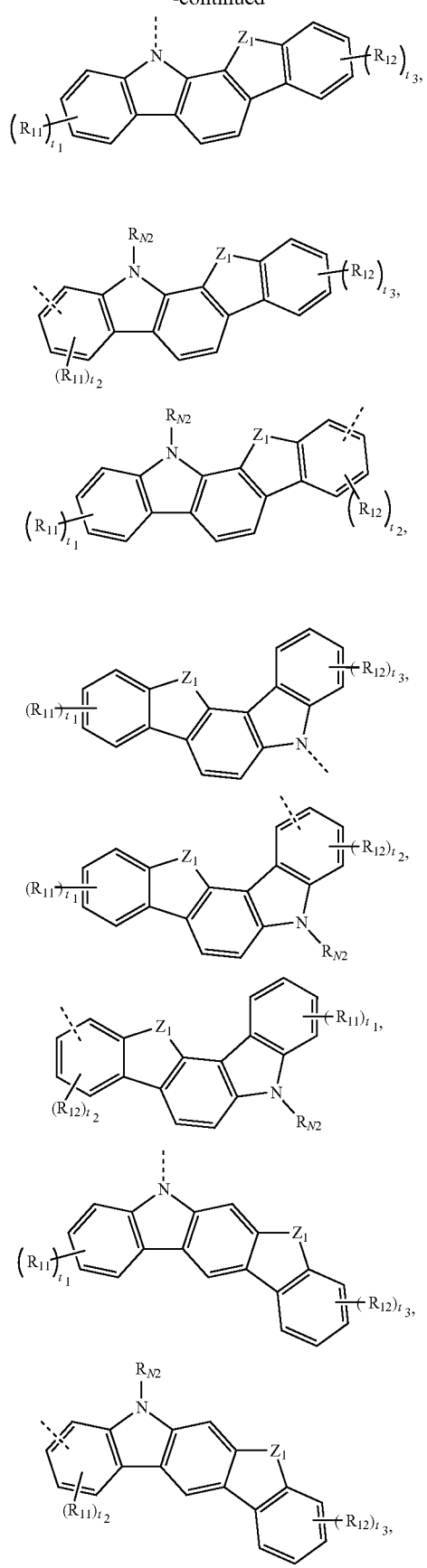

-continued

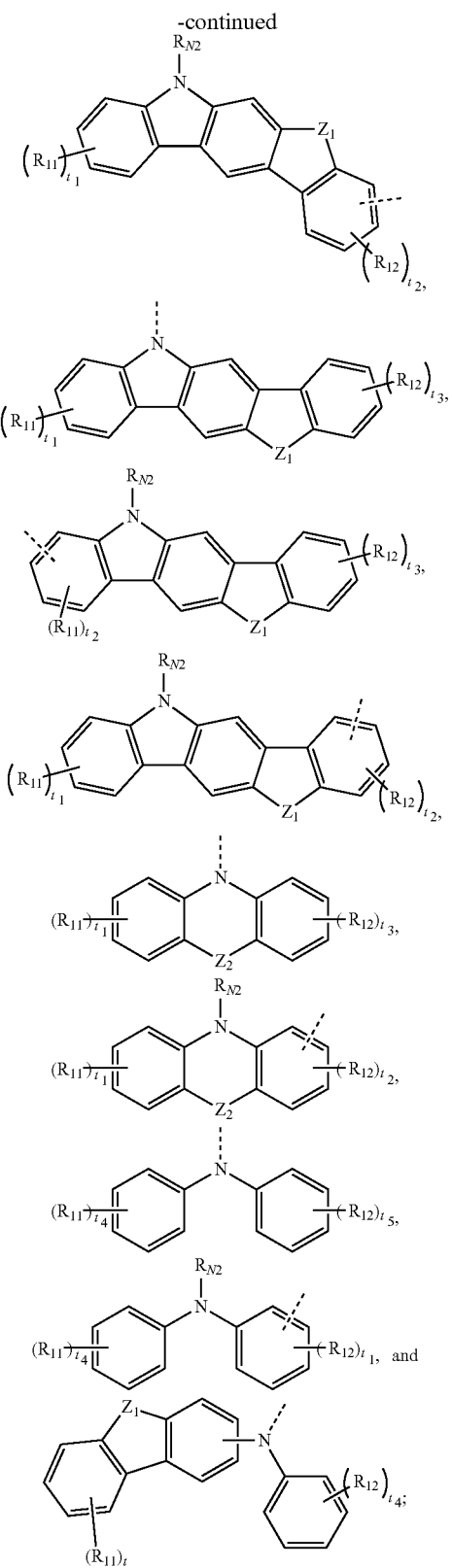

wherein the dashed line represents a linkage site of the group;

$Z_1$ and $Z_2$ are each independently any one selected from the group consisting of O, S, N—$R_{N3}$, $CR_{C3}R_{C4}$, and $SiR_{S3}R_{S4}$;

$R_{N2}$, $R_{N3}$, $R_{C3}$, $R_{C4}$, $R_{S3}$, and $R_{S4}$ are each independently any one selected from the group consisting of hydrogen, deuterium, unsubstituted or $R_{y3}$-substituted C1 to C20 straight or branched chain alkyl, unsubstituted or $R_{y3}$-substituted C6 to C20 aryl, and unsubstituted or $R_{y3}$-substituted C3 to C20 heteroaryl; and $R_{C3}$ and $R_{C4}$ are not joined or joined to form a ring through chemical bond(s);

$R_{11}$, $R_{12}$, and $R_{y3}$ are each independently any one selected from the group consisting of deuterium, halogen, cyano, C1 to C10 straight or branched chain alkyl, C1 to C10 alkoxy, C1 to C10 alkylthio, C6 to C12 aryl, C2 to C20 heteroaryl, and C6 to C18 arylamine;

$t_1$ and $t_3$ are each independently an integer of 0-4;

$t_2$ is an integer of 0-3; and $t_4$ and $t_5$ are each independently an integer of 0-5.

8. The organic compound according to claim 7, wherein $R_2$ and $R_3$ are each independently any one selected from the group consisting of the following groups and the following groups substituted with substituent(s):

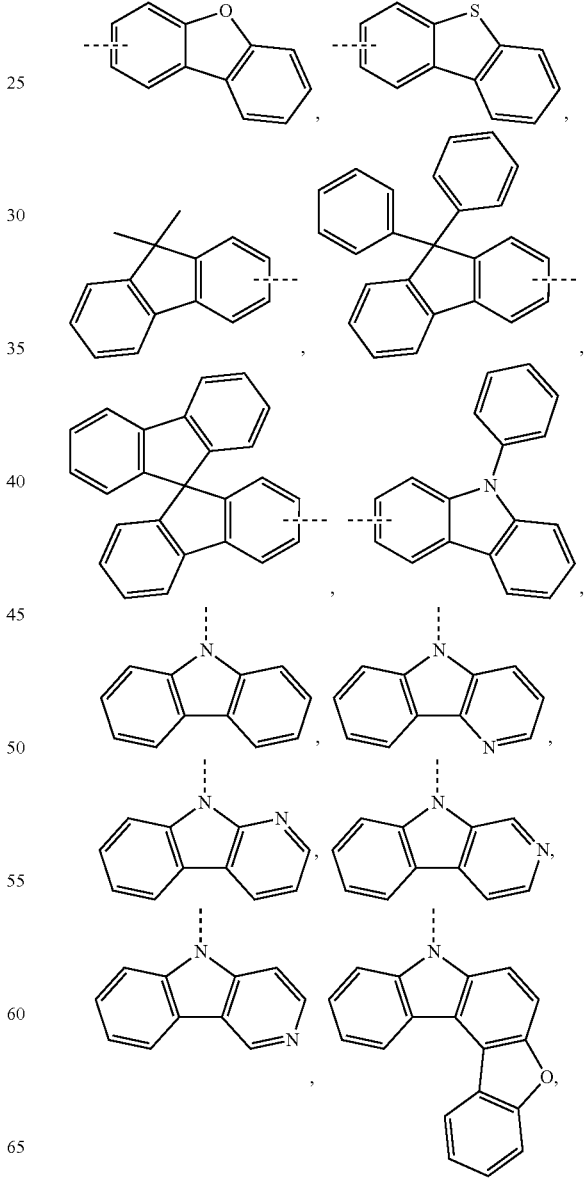

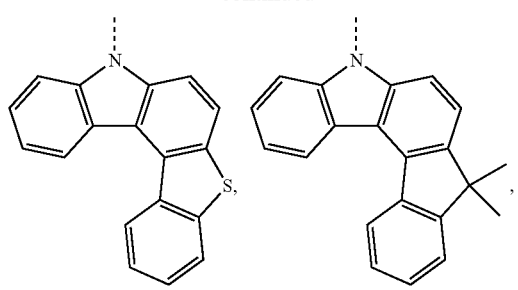
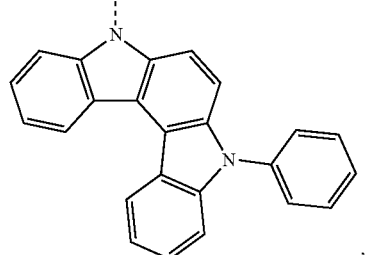
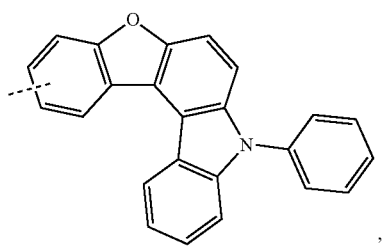
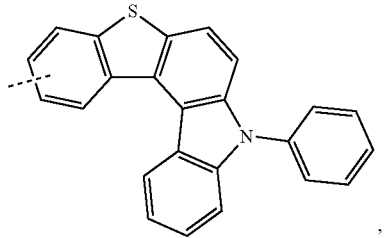
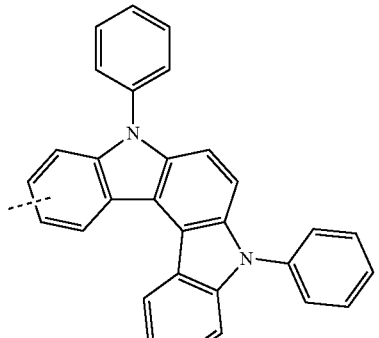
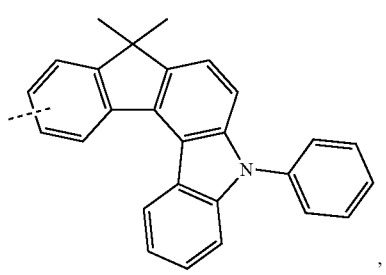
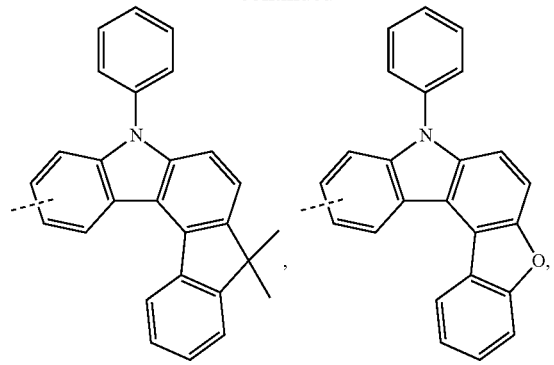
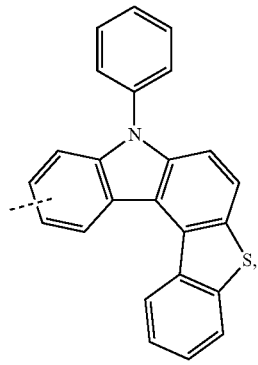
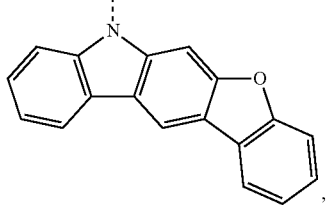
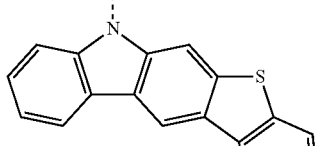
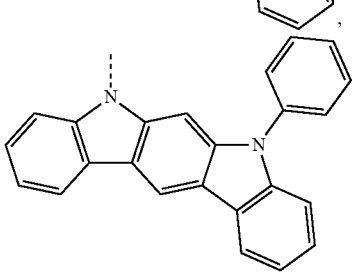
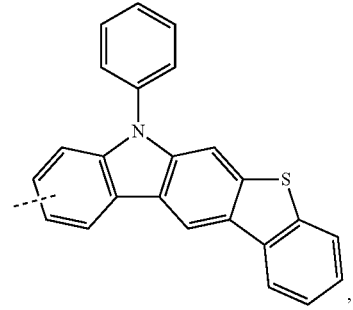

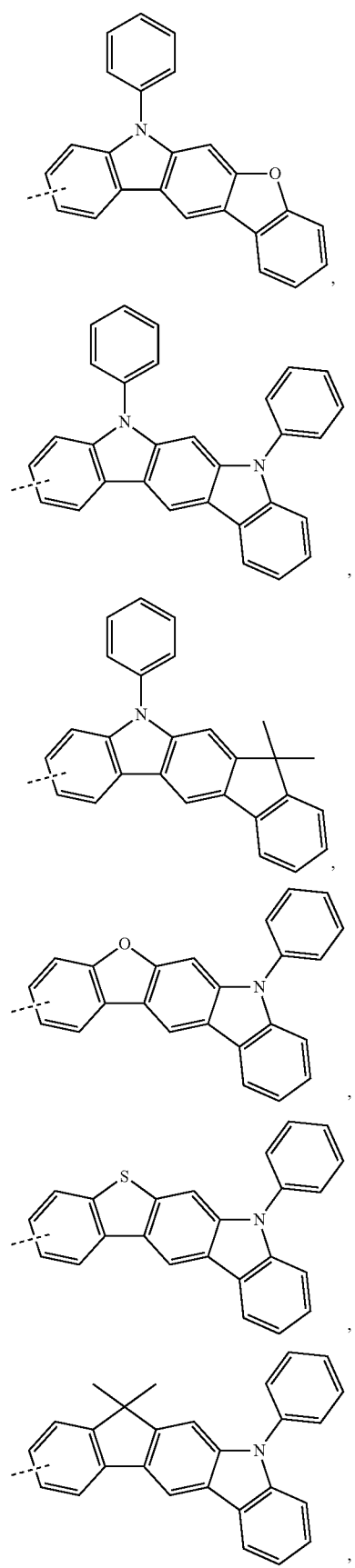
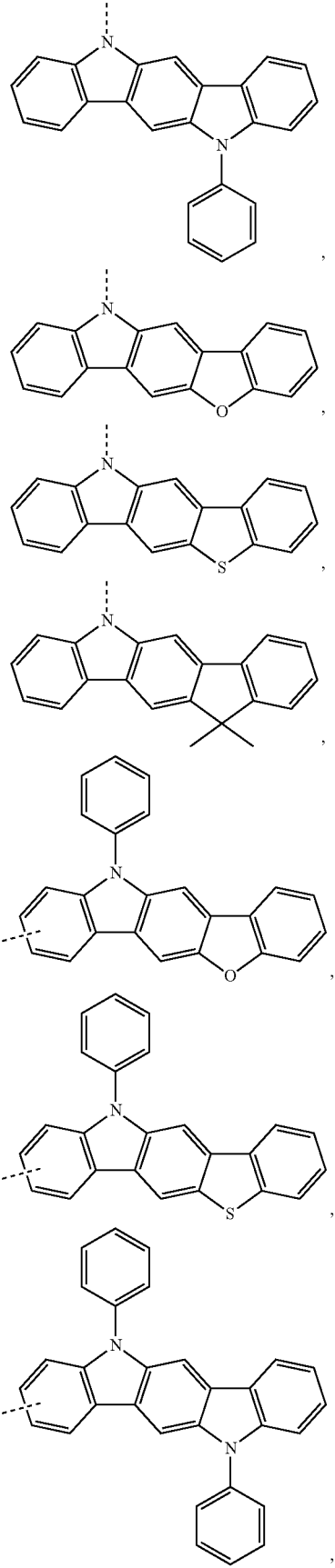

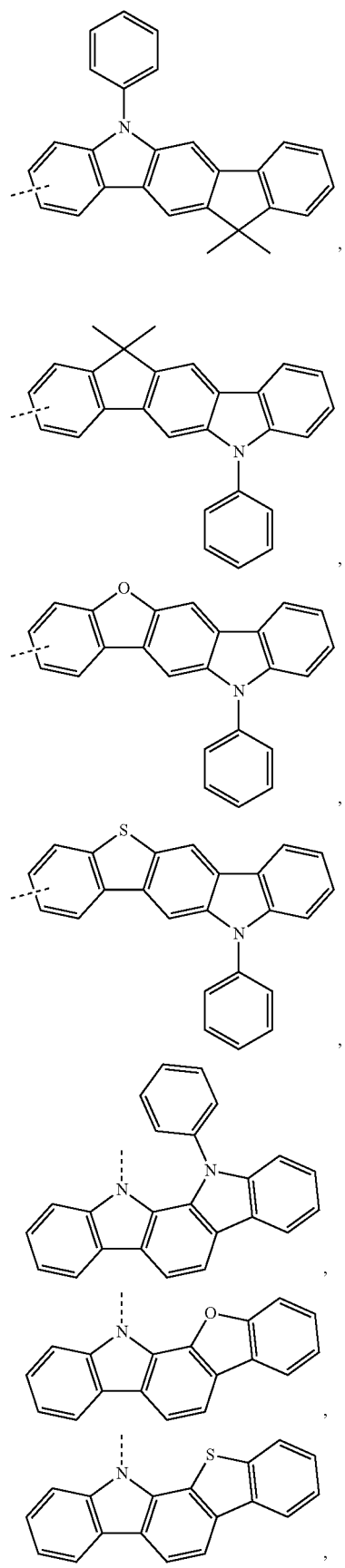
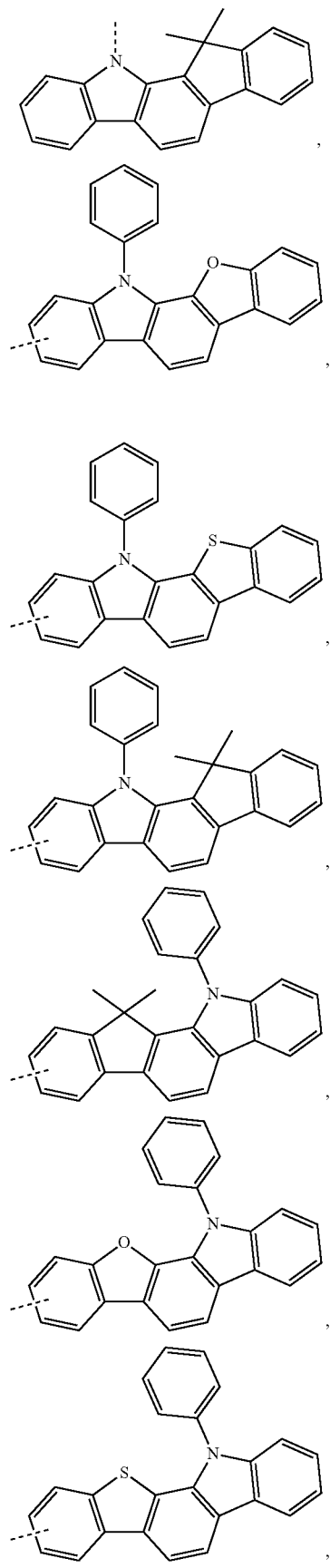

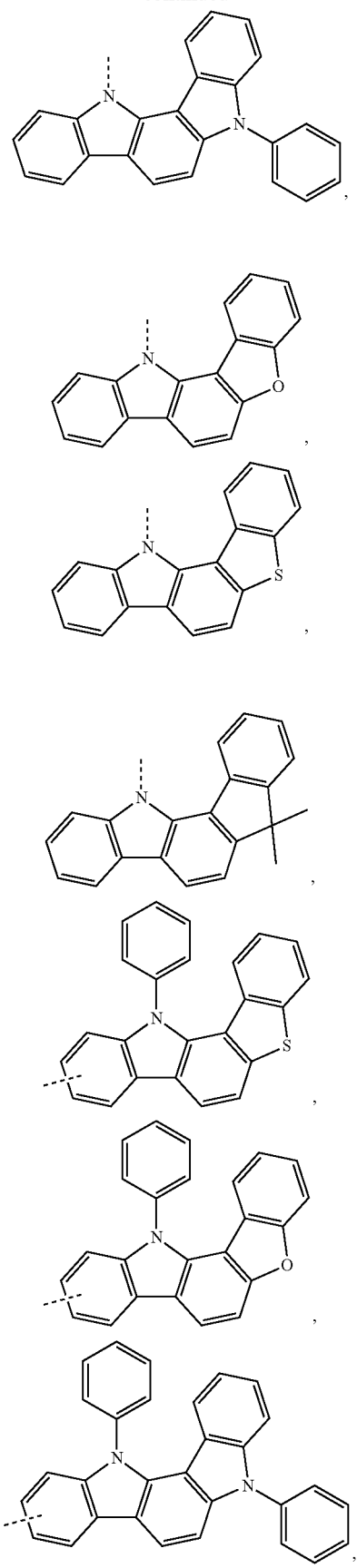
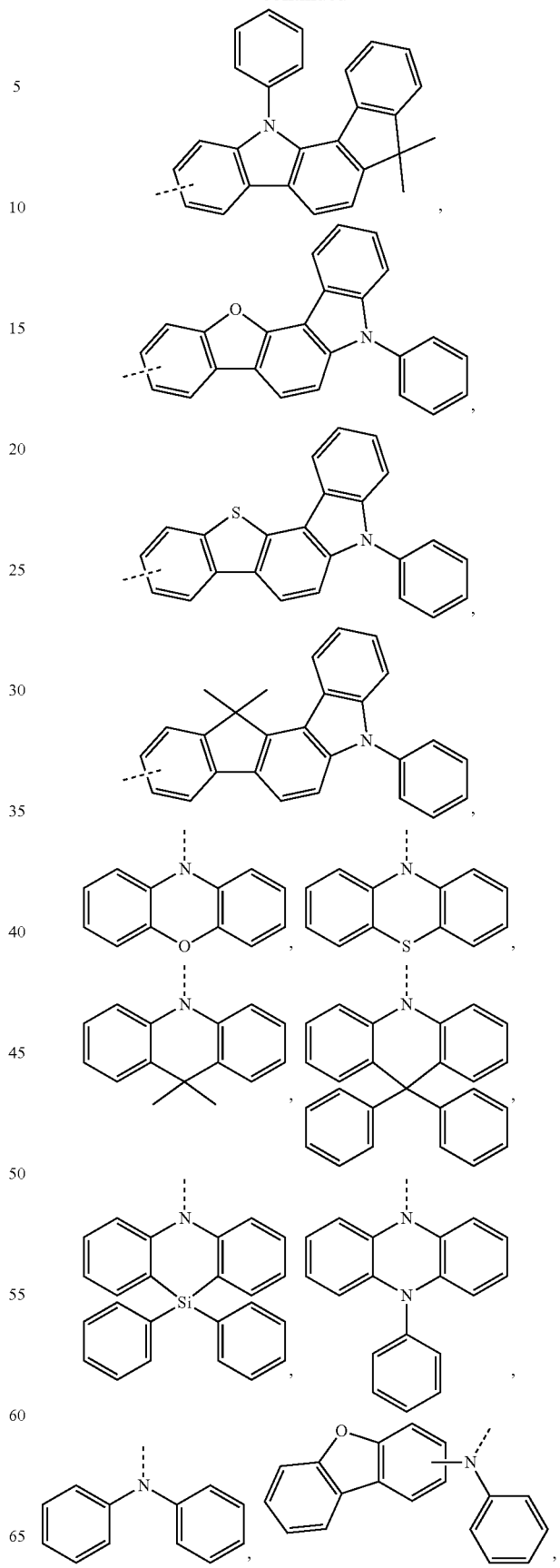

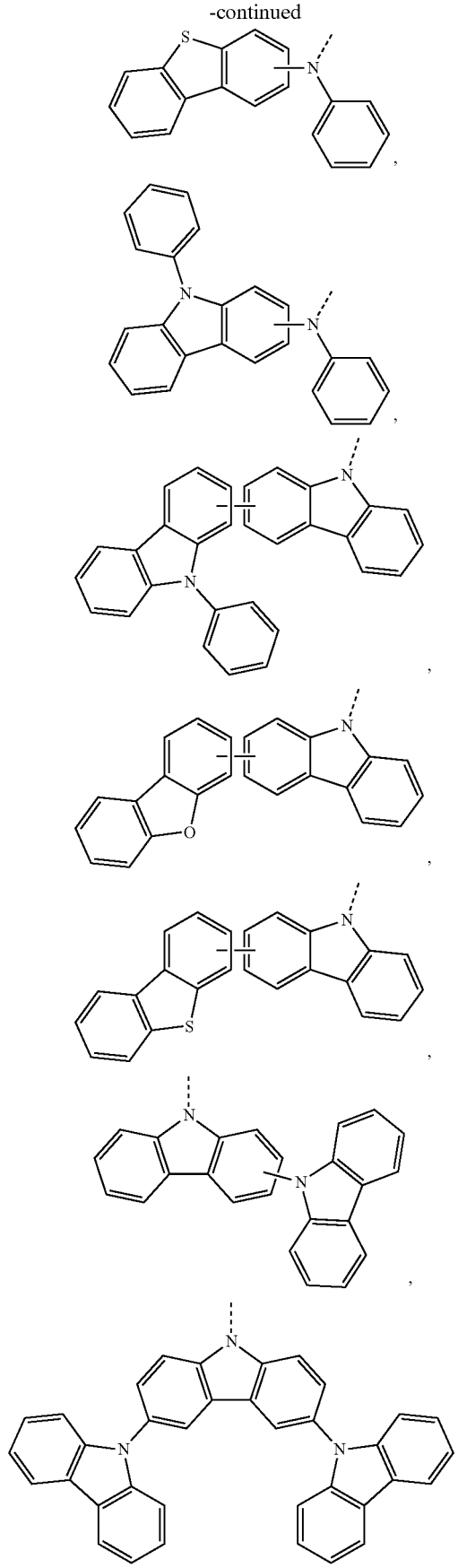

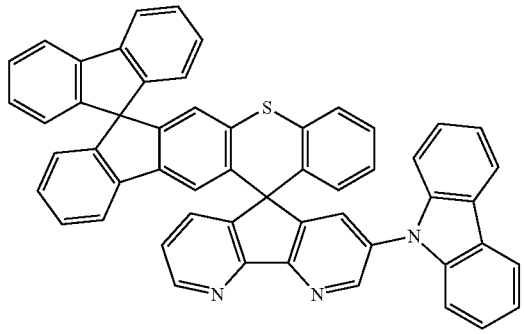

wherein the dashed line represents a linkage site of the group; and the substituent(s) is(are) each independently any one selected from the group consisting of deuterium, C1 to C10 straight or branched chain alkyl, C1 to C10 alkoxy, C1 to C10 alkylthio, C6 to C20 aryl, C2 to C20 heteroaryl, and C6 to C18 arylamine.

9. The organic compound according to claim 1, wherein $n_1$, $n_2$, $n_3$, $n_4$, $n_5$, $n_6$, $m_1$, $m_2$, $m_3$, $m_4$, $m_5$, and $m_6$ are each independently an integer of 0-2, and $m_1$, $m_2$, $m_3$, $m_4$, $m_5$, and $m_6$ are not simultaneously 0.

10. The organic compound according to claim 1, wherein the organic compound is any one selected from the group consisting of the following compounds P1 to P233:

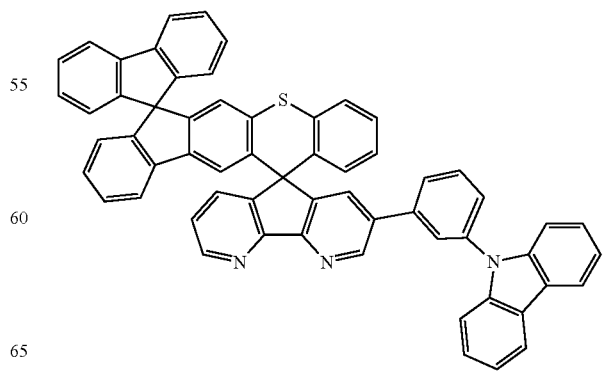

P3
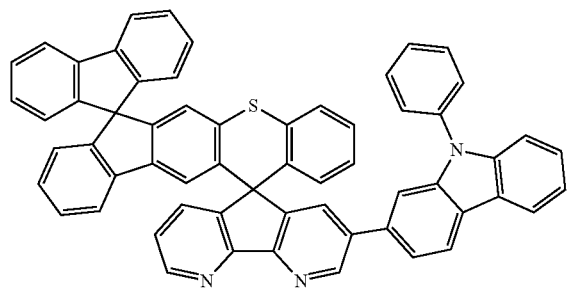
P4
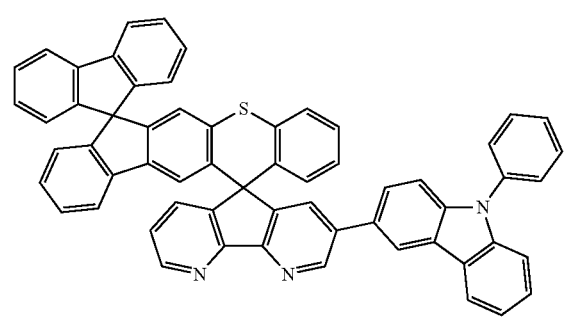
P5
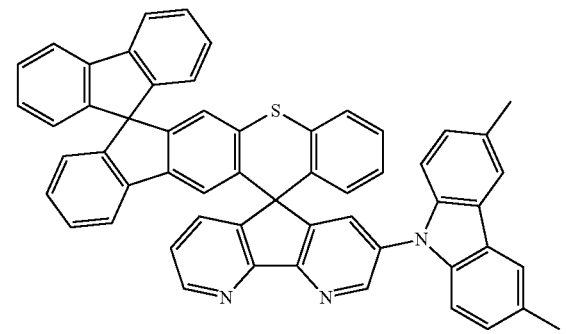
P6
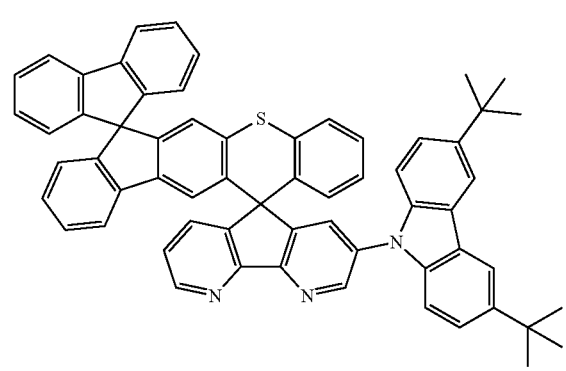
P7
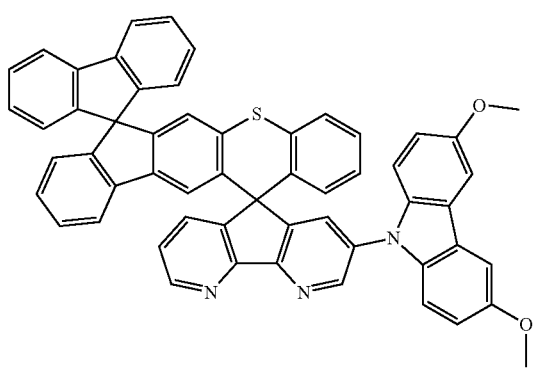
P8
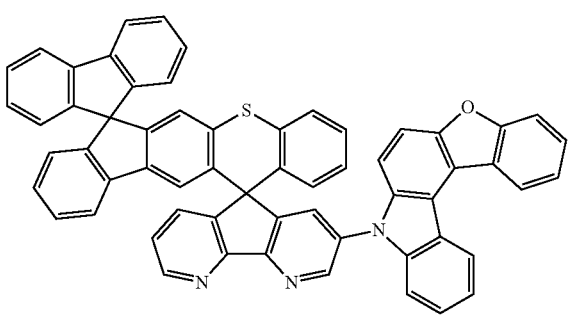
P9
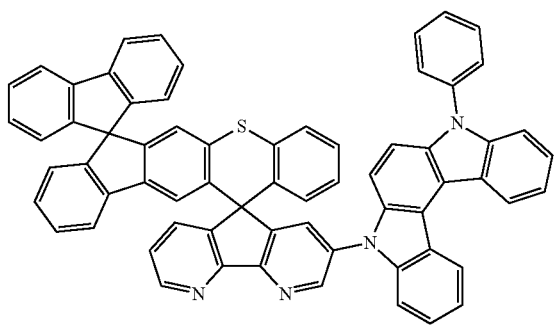
P10
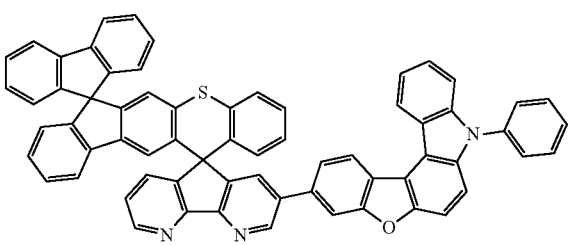
P11

-continued
P12
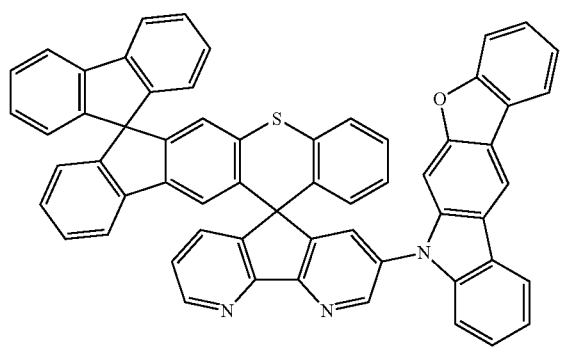
P13
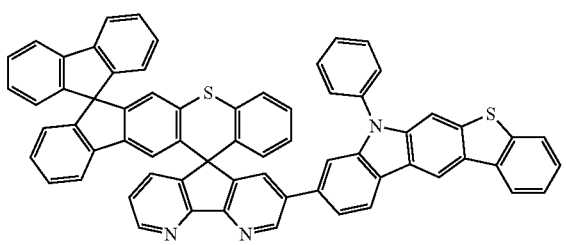
P14
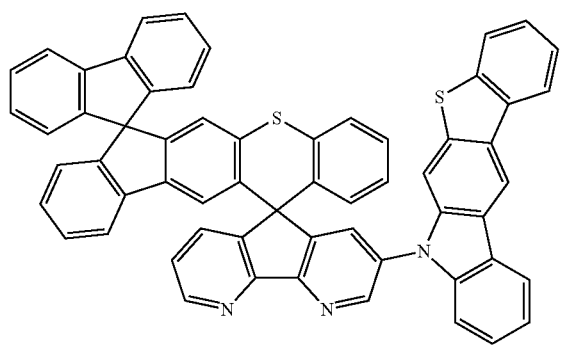
P15
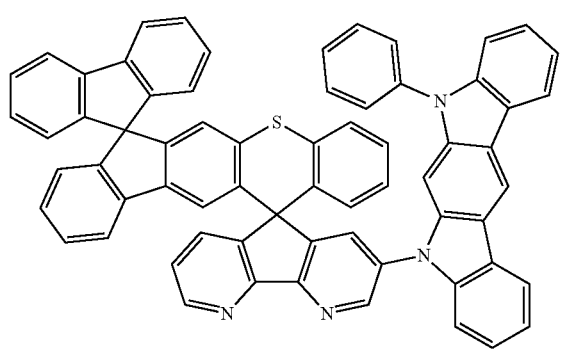
-continued
P16
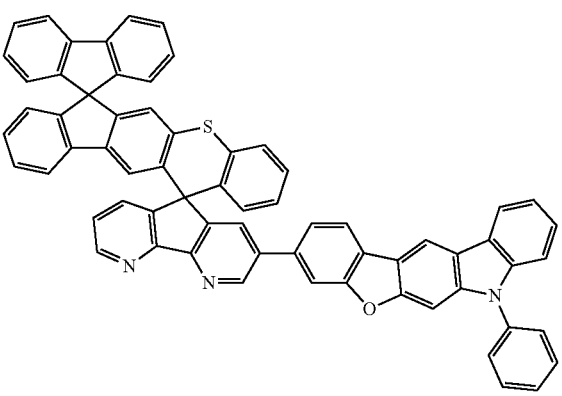
P17
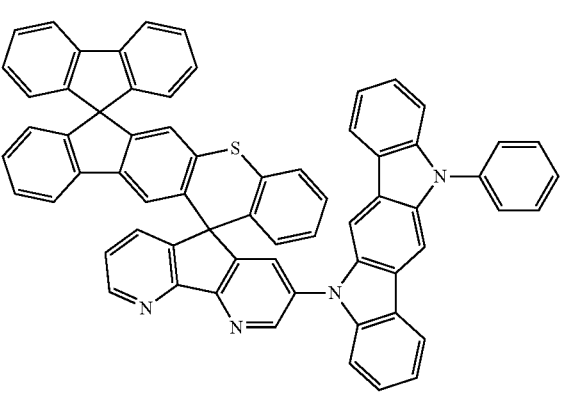
P18
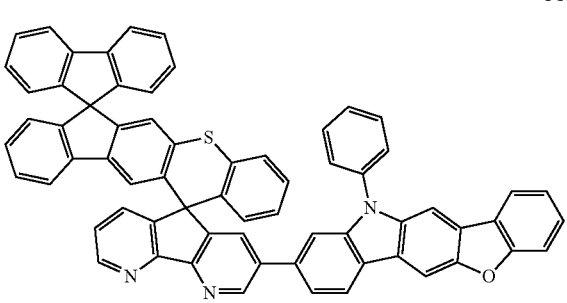
P19
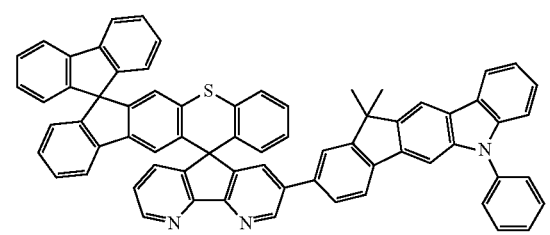

P20
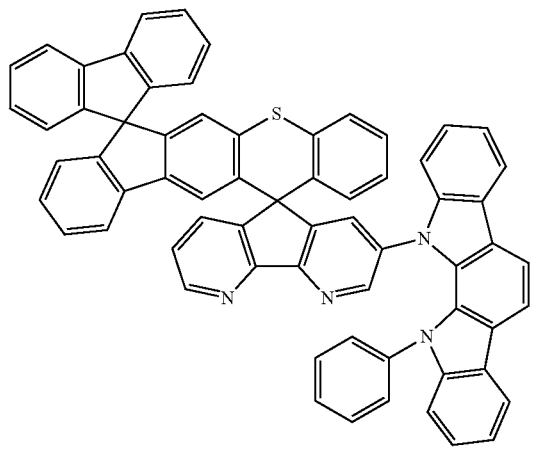
P21
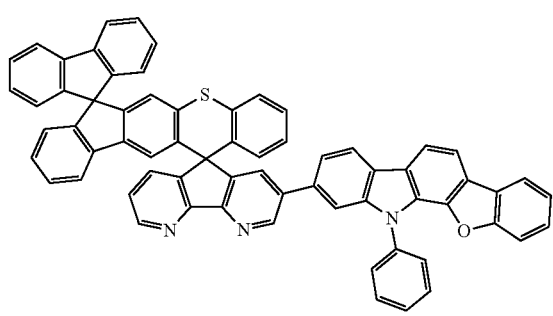
P22
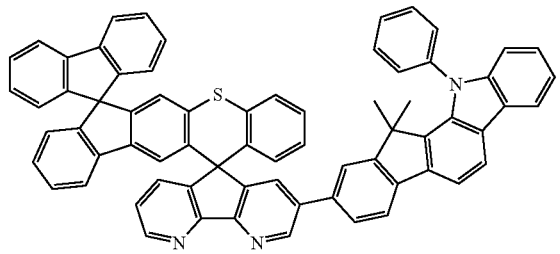
P23
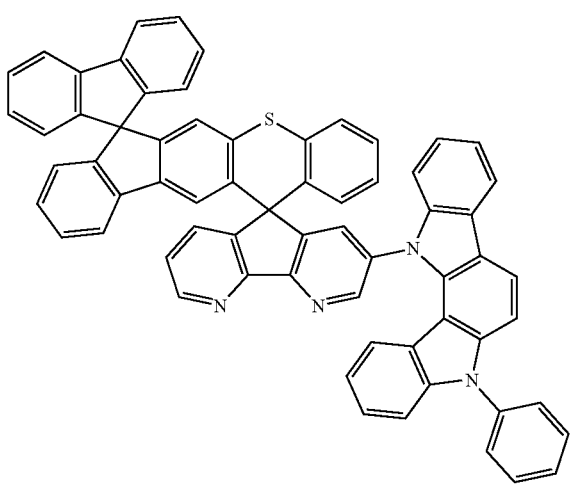
P24
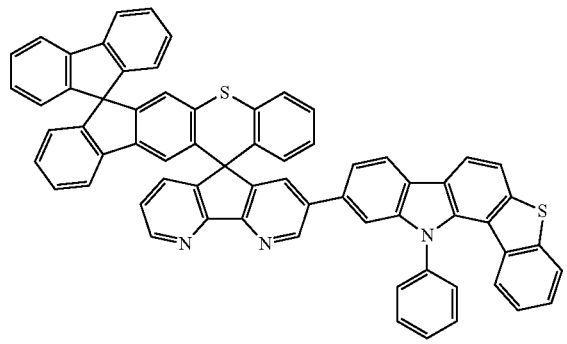
P25
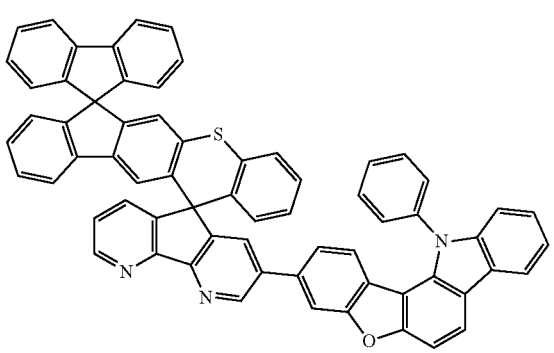
P26
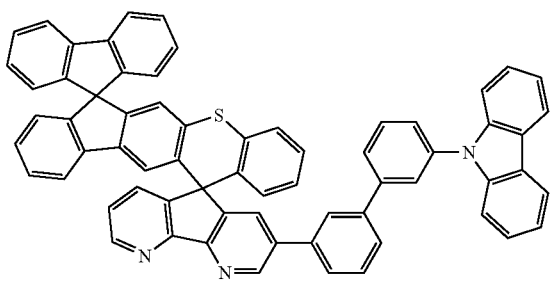
P27
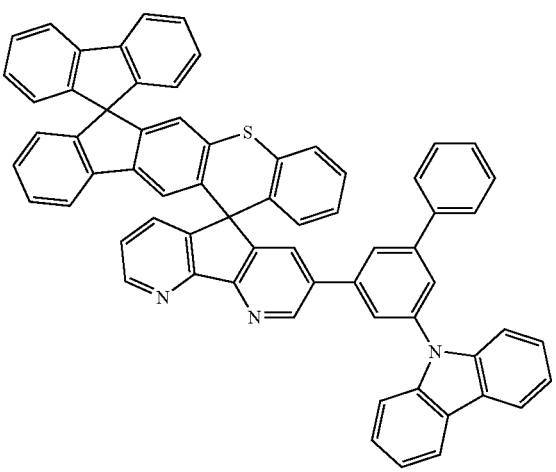

P28
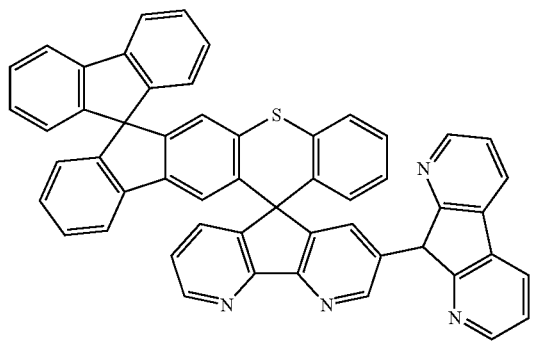
P29
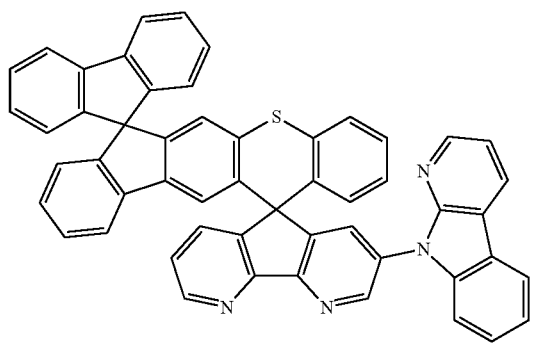
P30
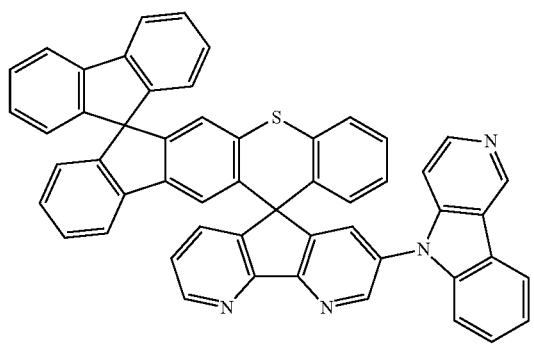
P31
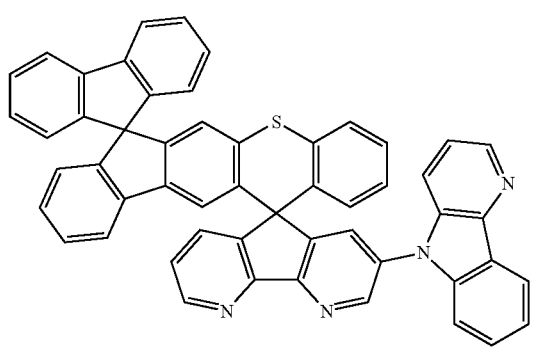
P32
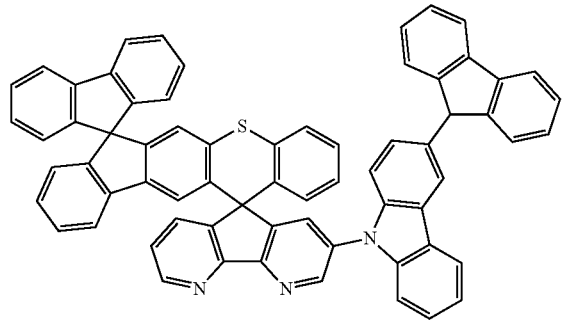
P33
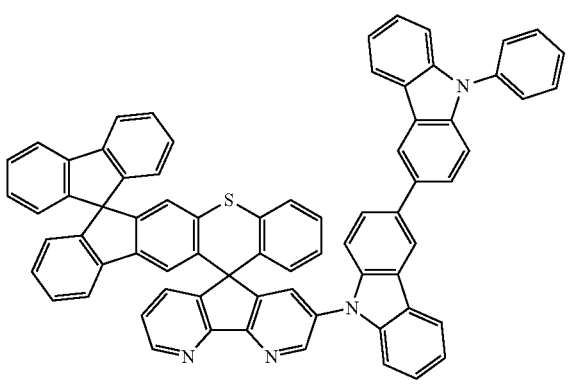
P34
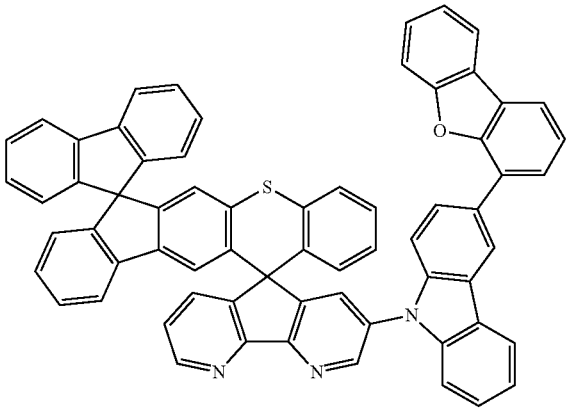
P35
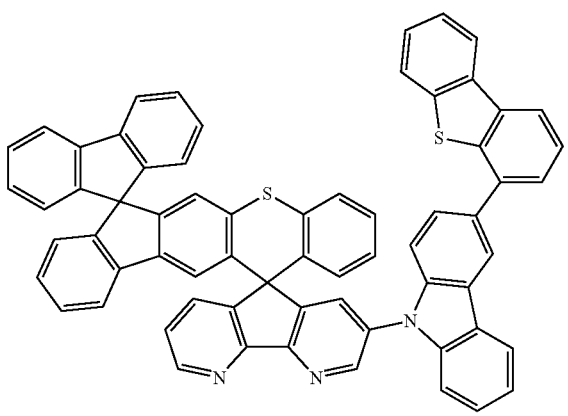

P36
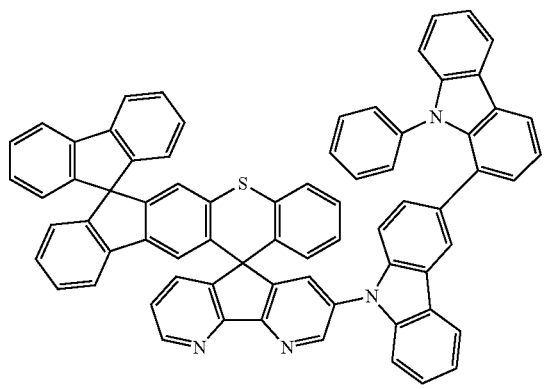
P37
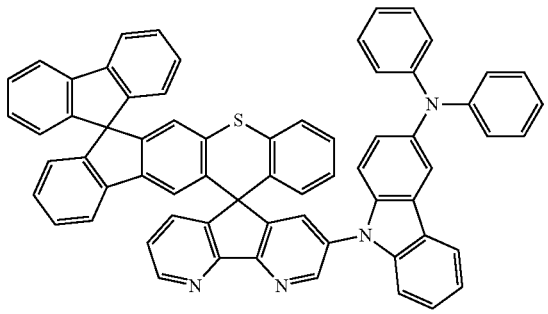
P38
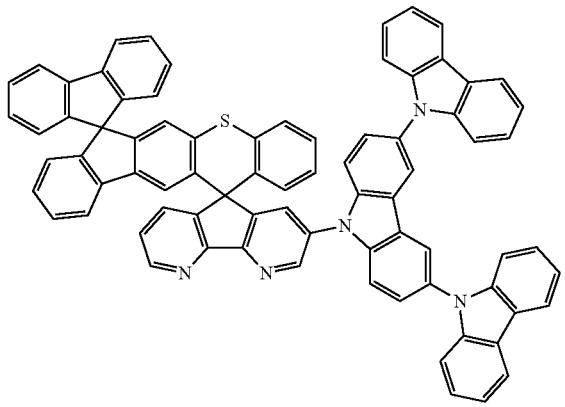
P39
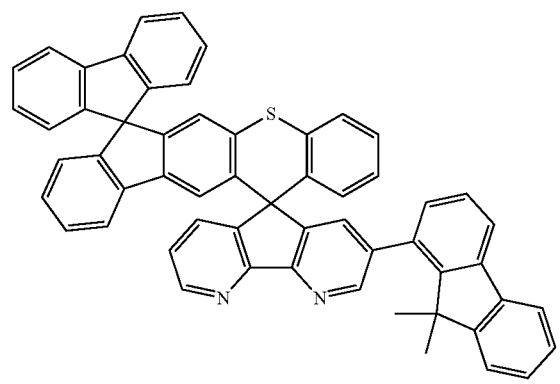
P40
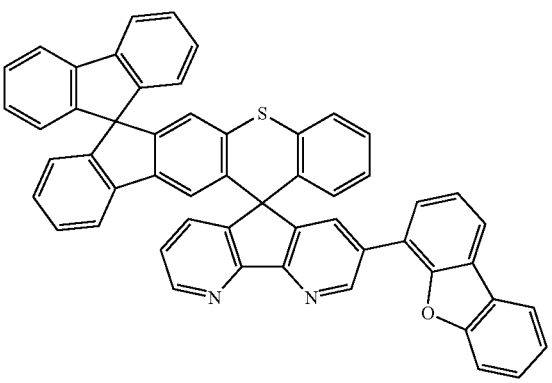
P41
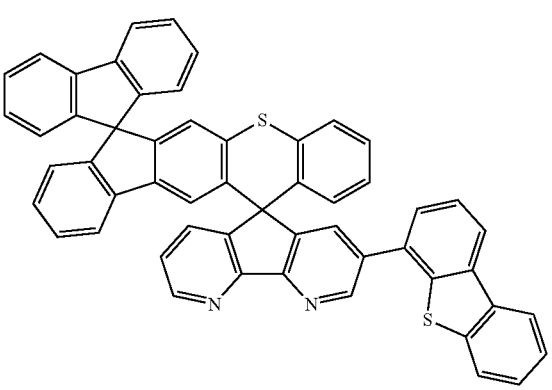
P42
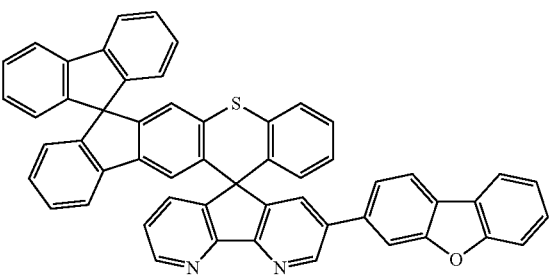
P43
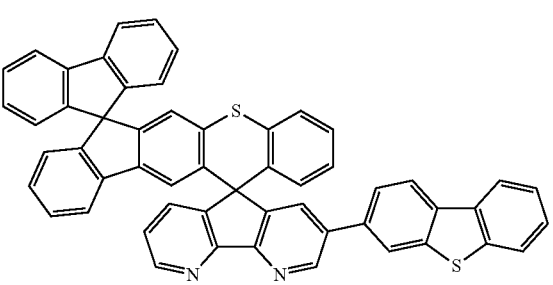

P44
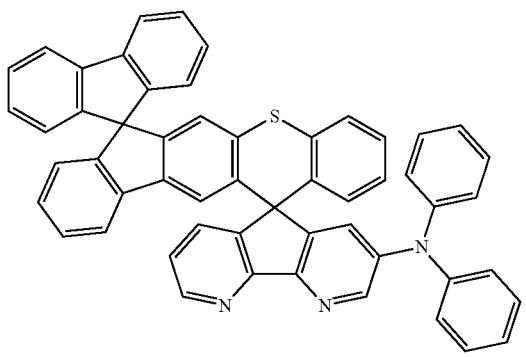
P45
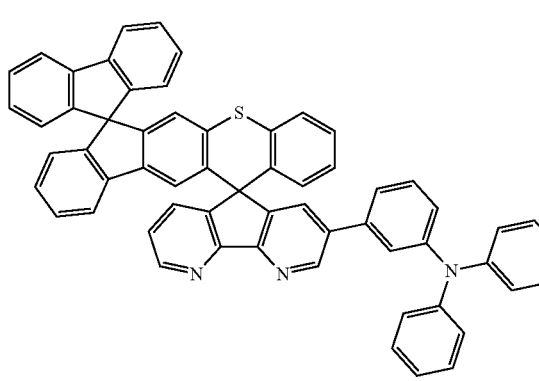
P46
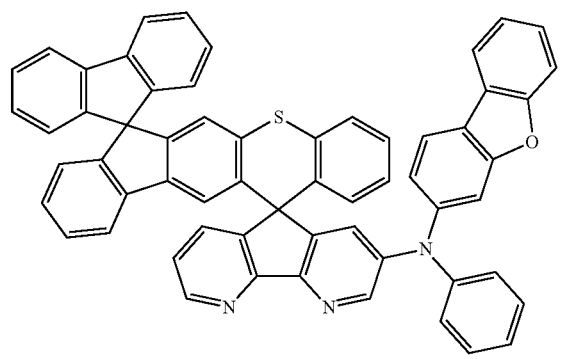
P47
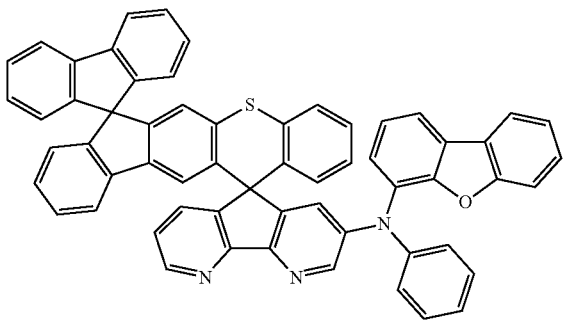
P48
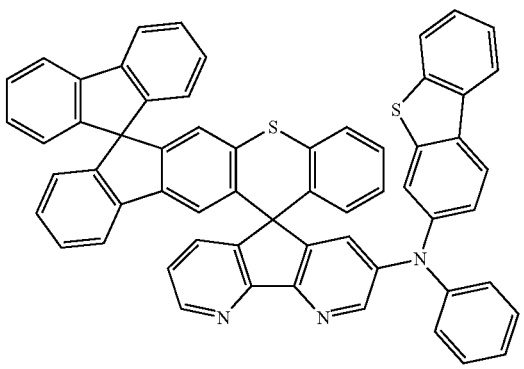
P49
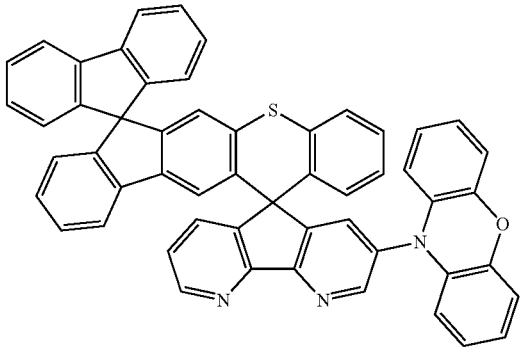
P50
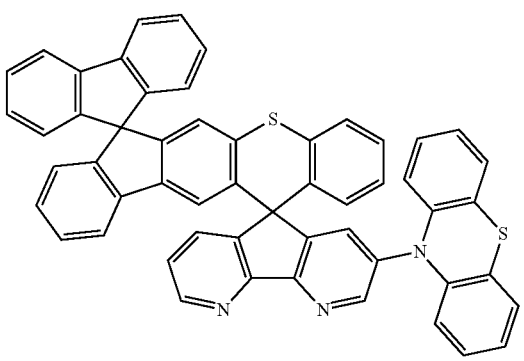
P51
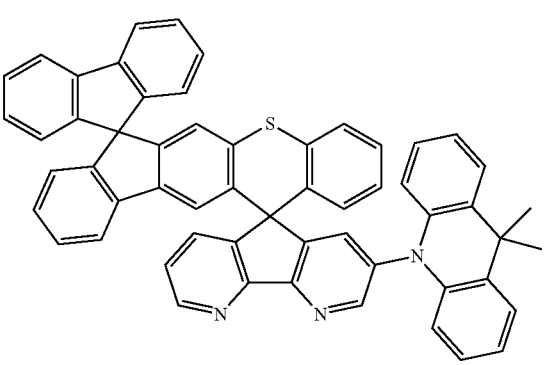

P52
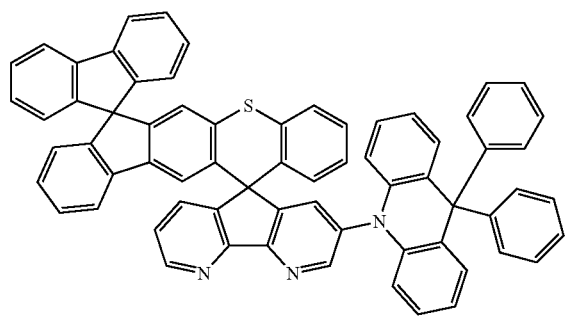
P53
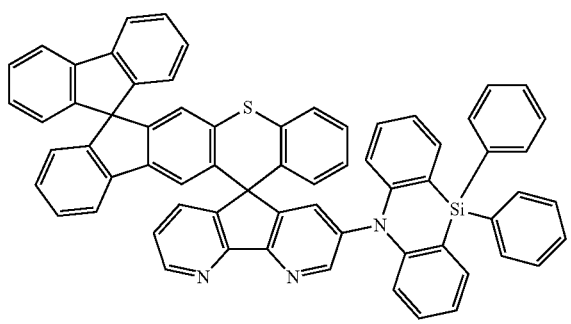
P54
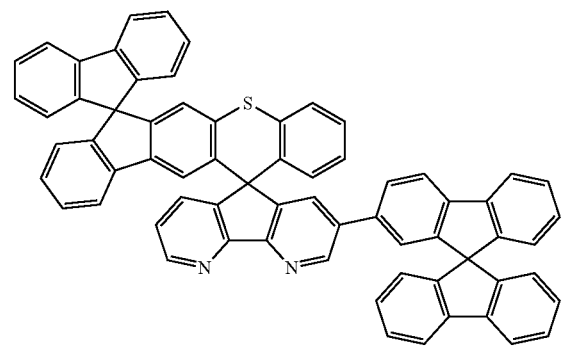
P55
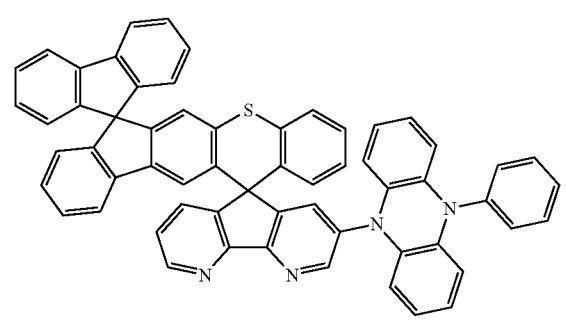
P56
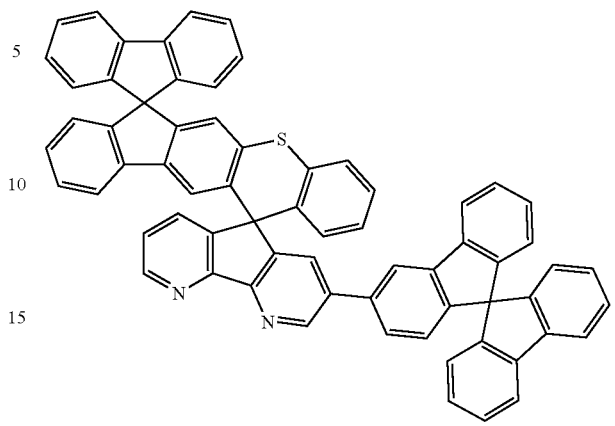
P57
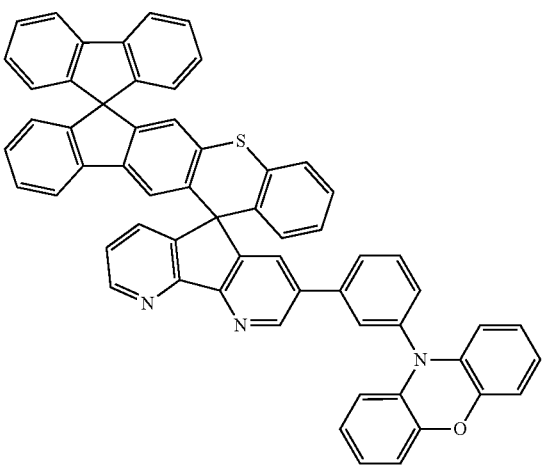
P58
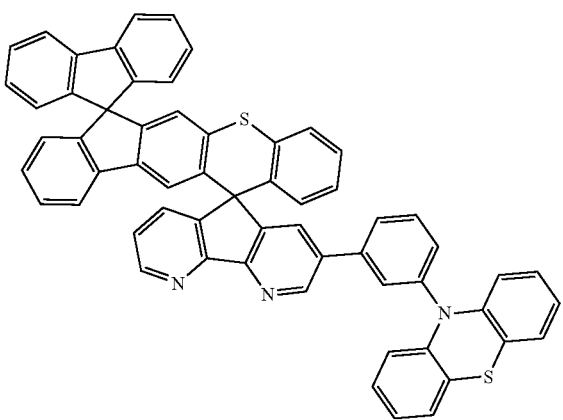

P59
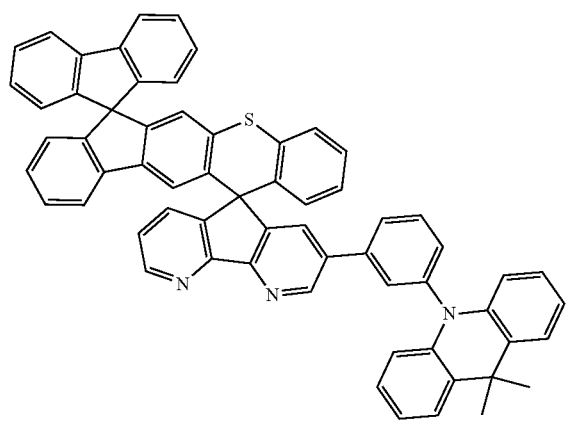
P60
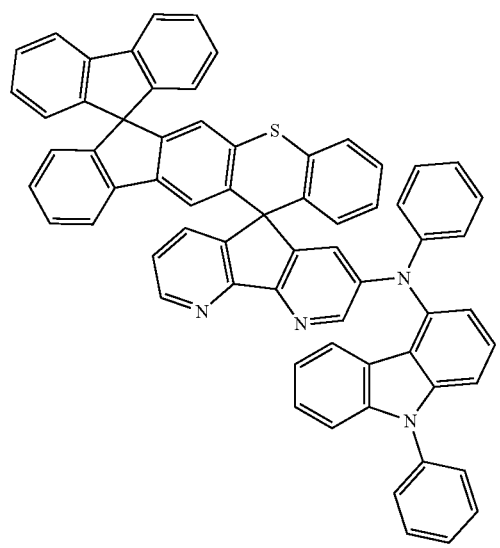
P61
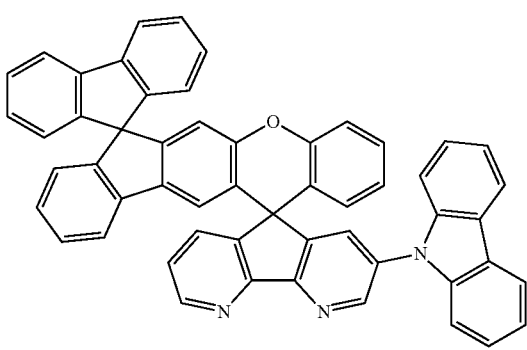
P62
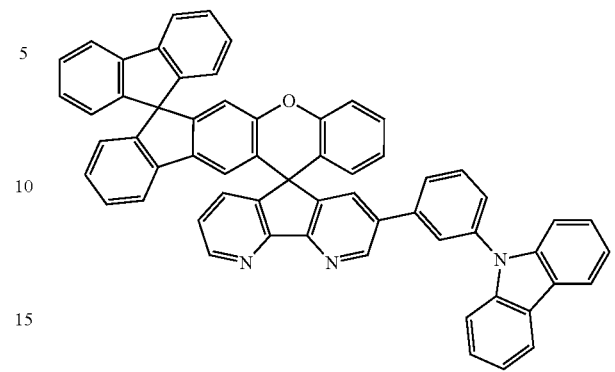
P63
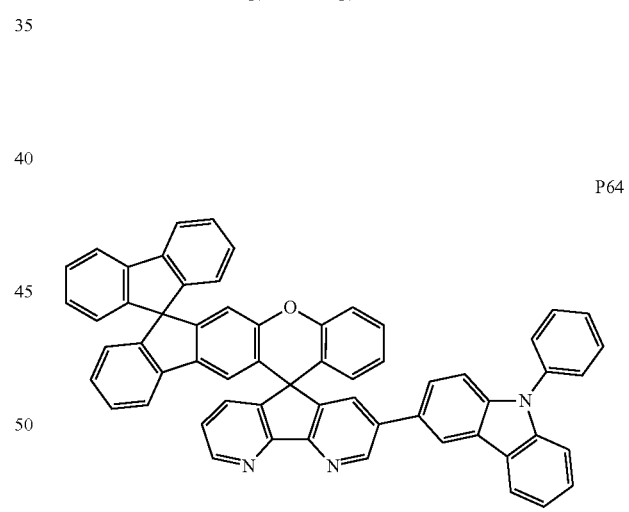
P64
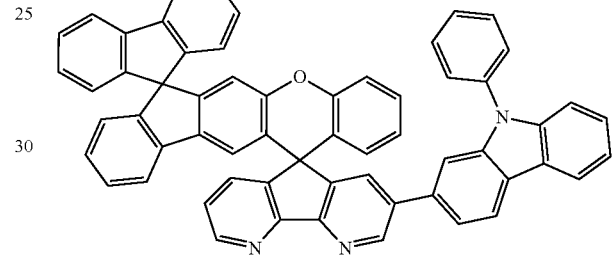
P65
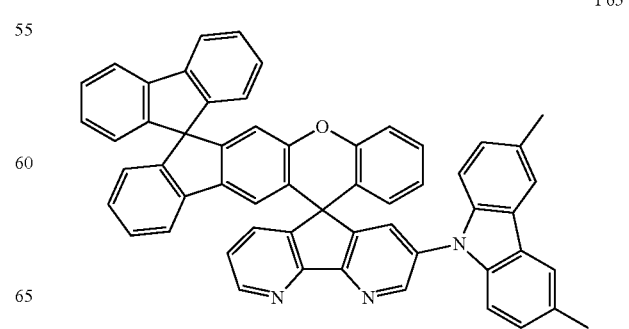

P66
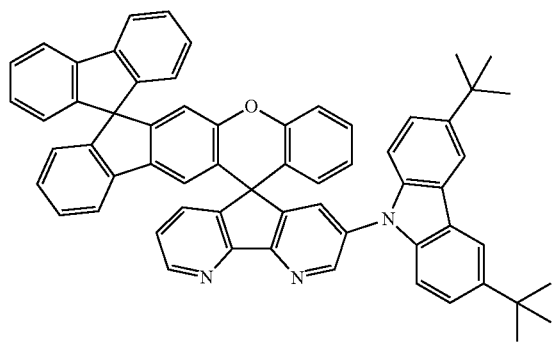
P67
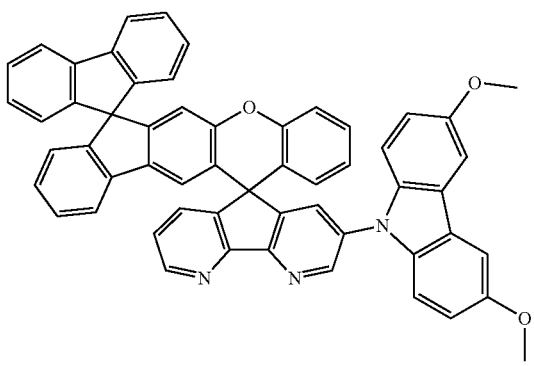
P68
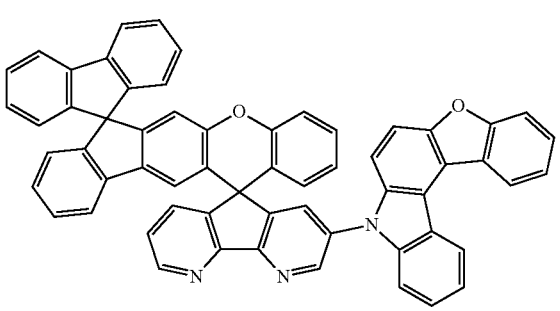
P69
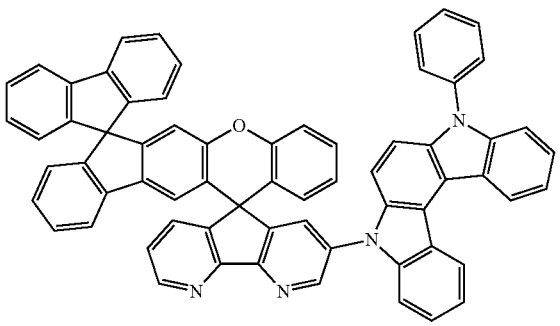
P70
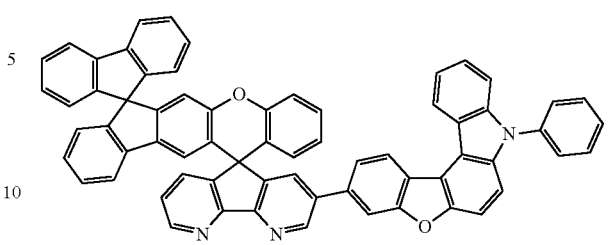
P71
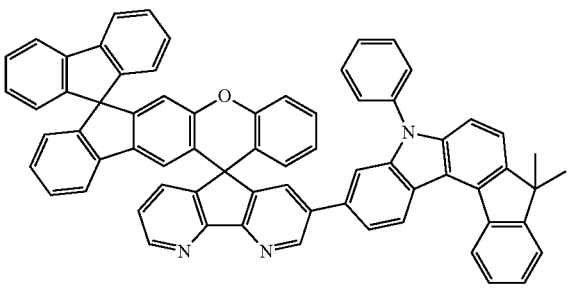
P72
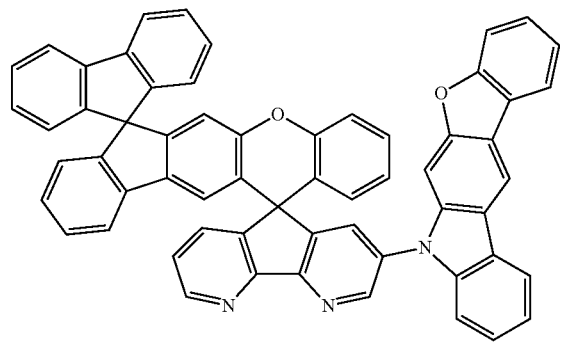
P73
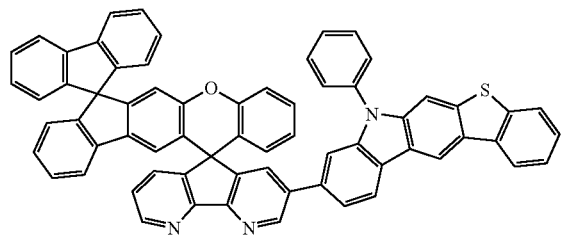
P74
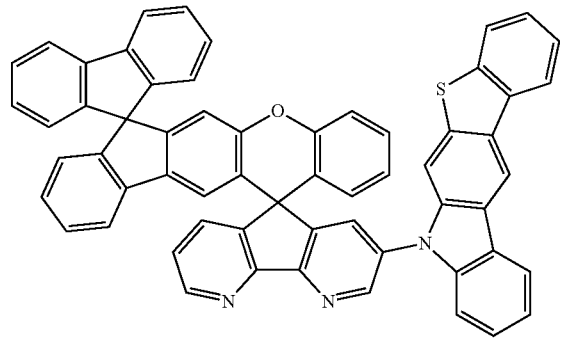

P75
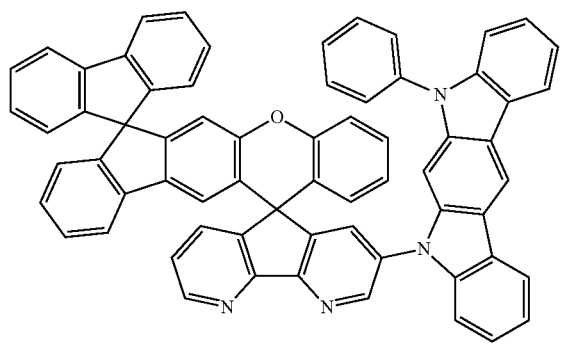
P76
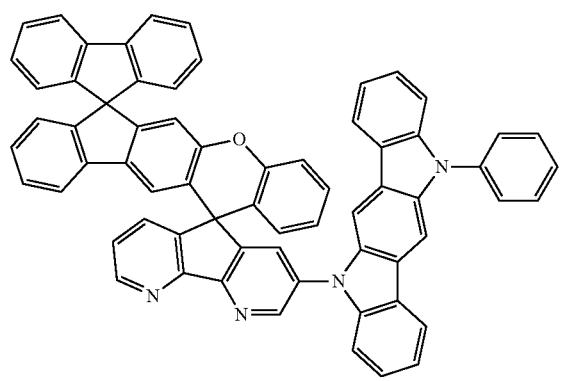
P77
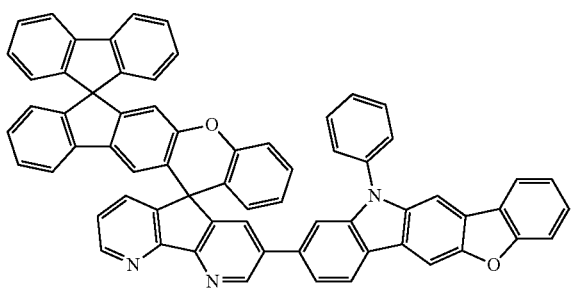
P78
P79
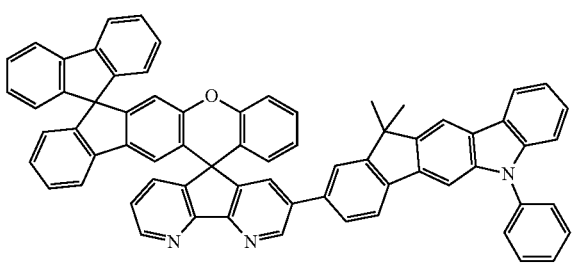
P80
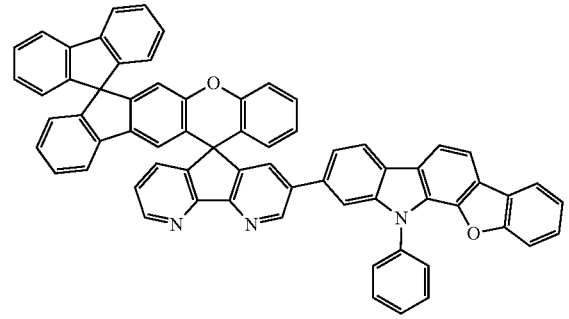
P81
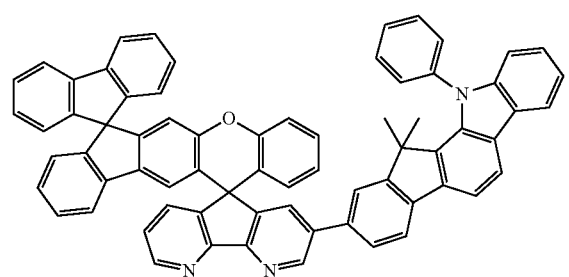
P82

P83
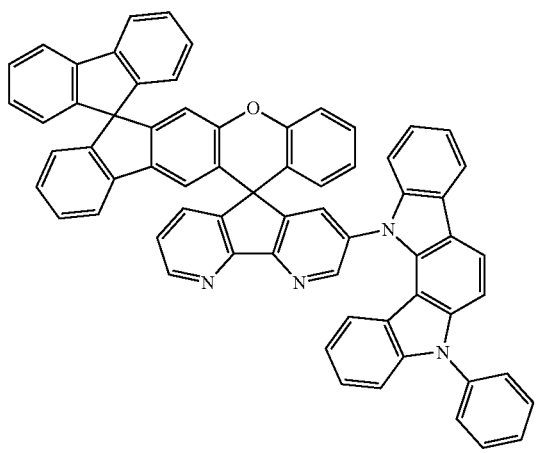
P84
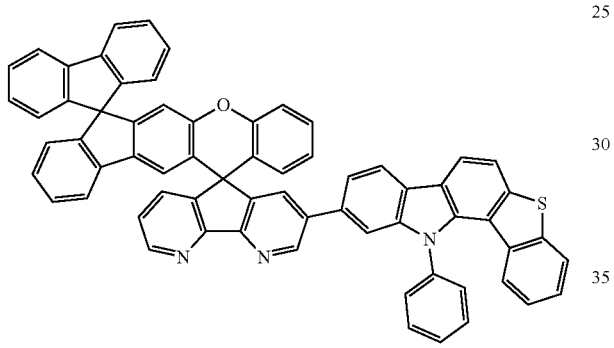
P85
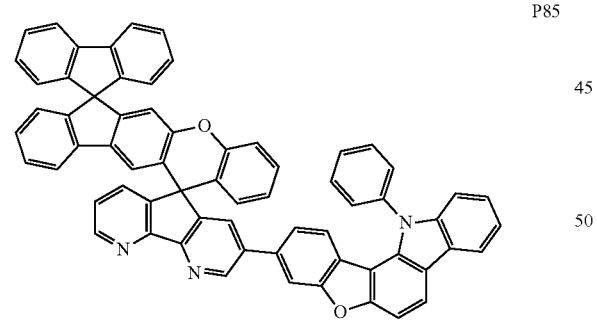
P86
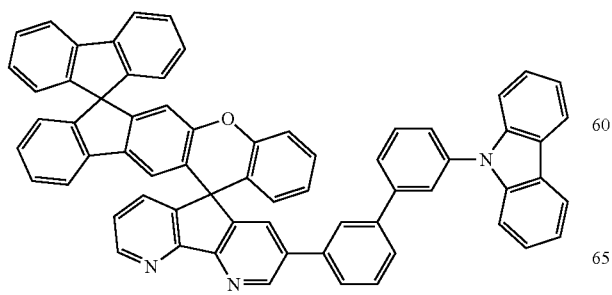
P87
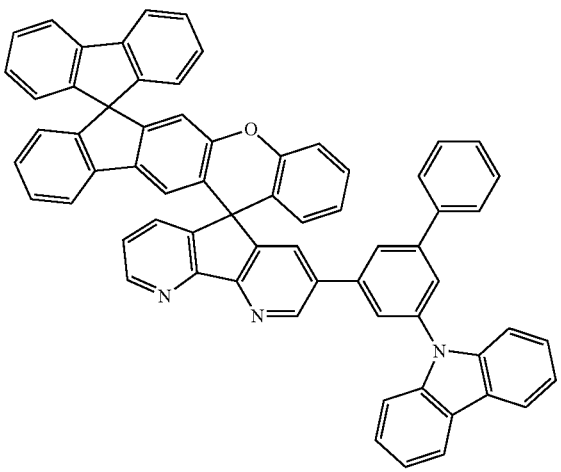
P88
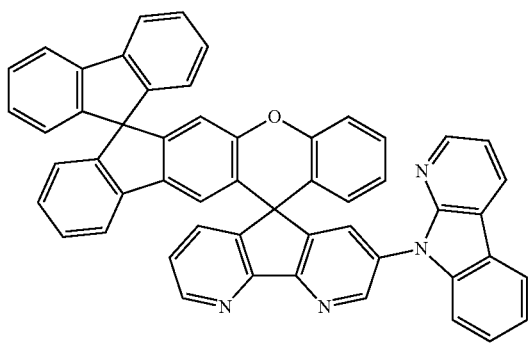
P89
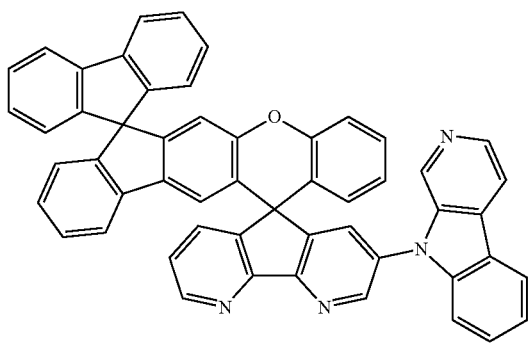
P90
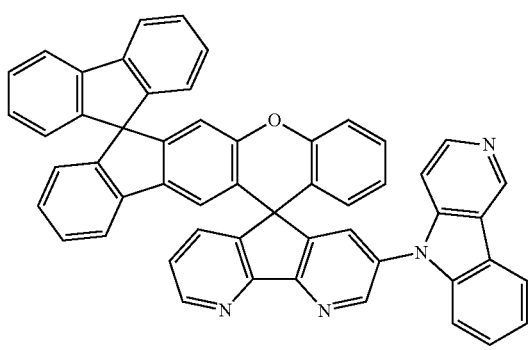

-continued
P91
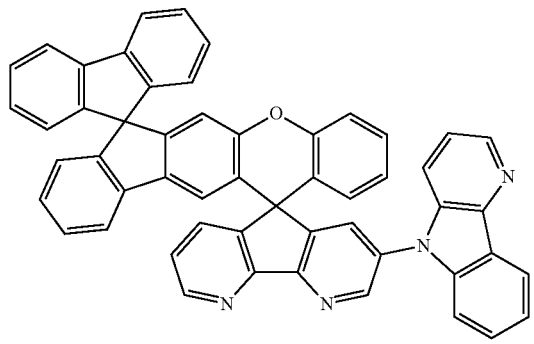
P92
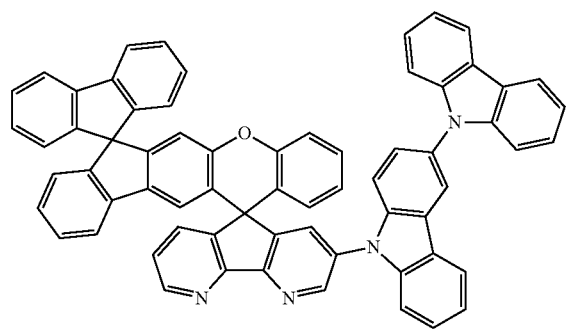
P93
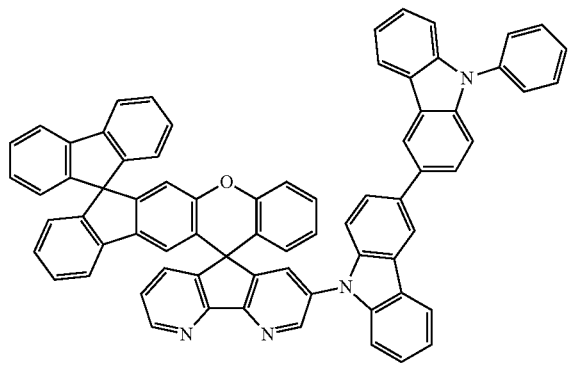
P94
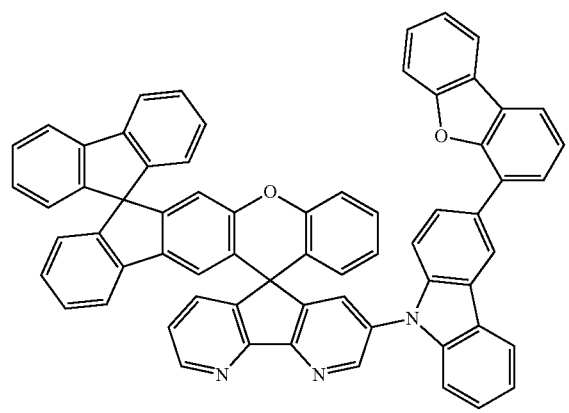
-continued
P95
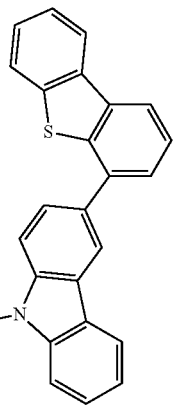
P96
P97
P98
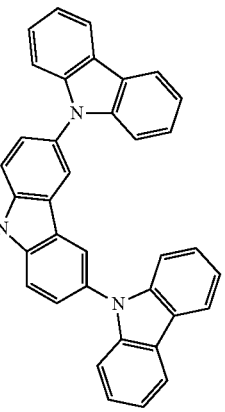

P99
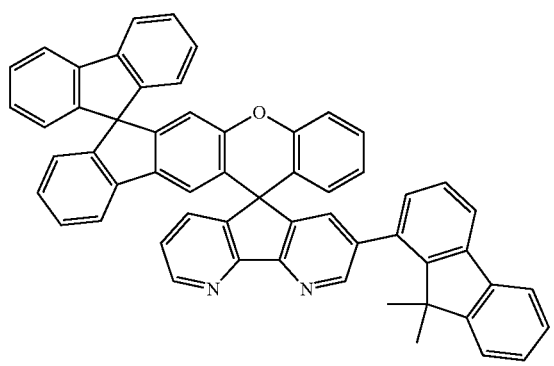
P100
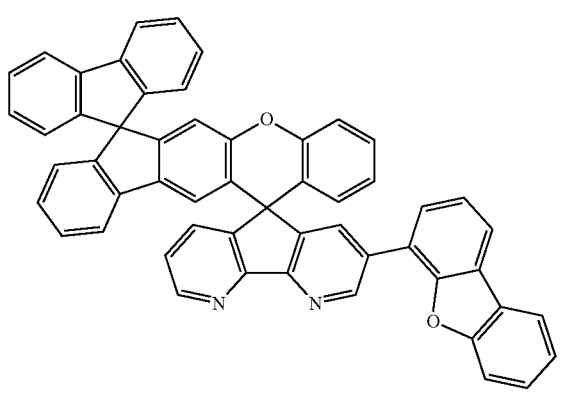
P101
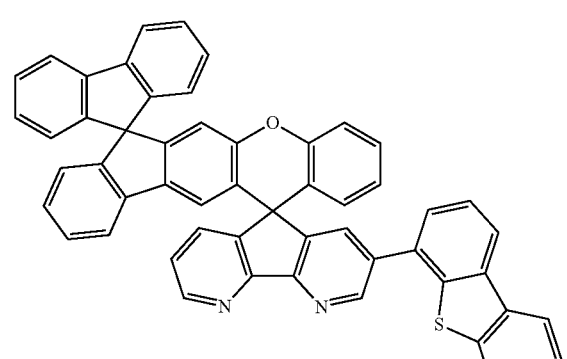
P102
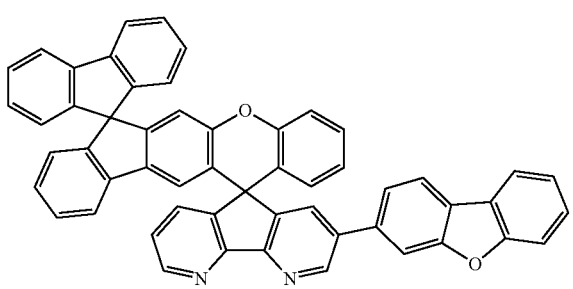
P103
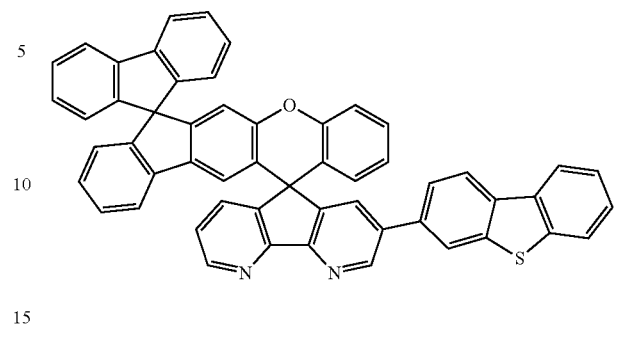
P104
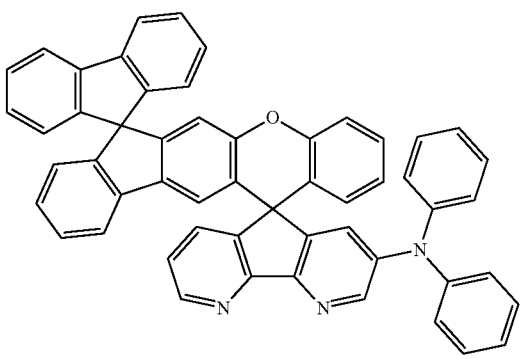
P105
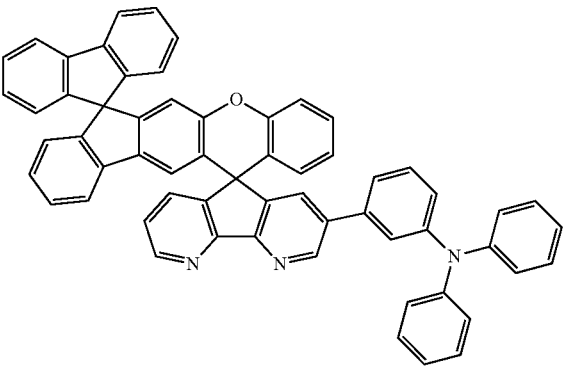
P106
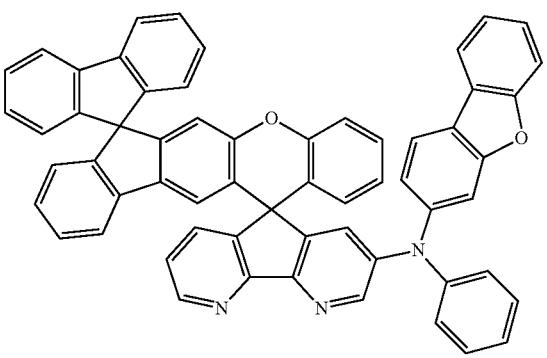

P107
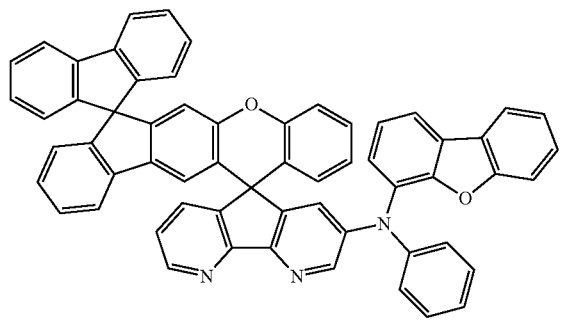
P108
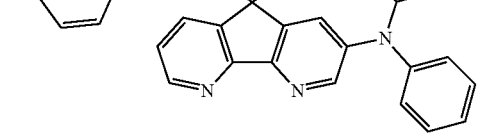
P109
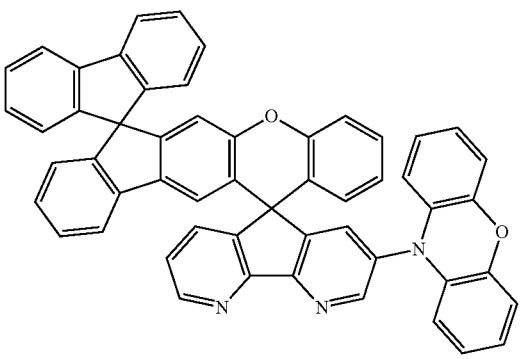
P110
P111
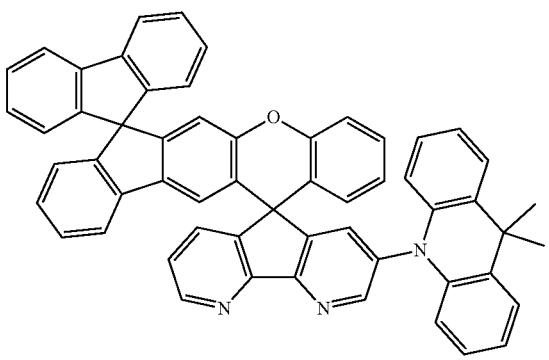
P112
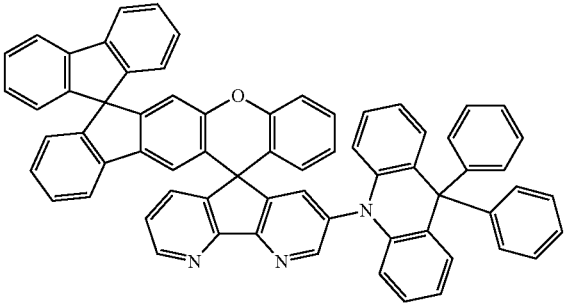
P113
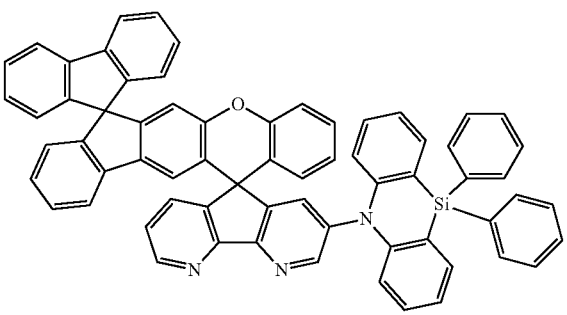
P114
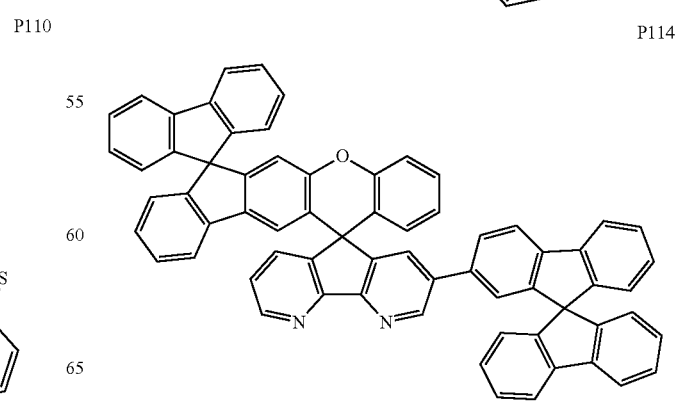

-continued
P115
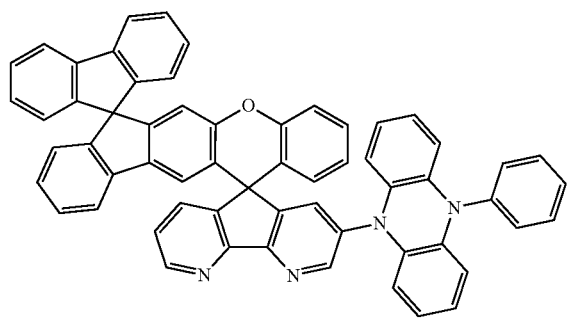
P116
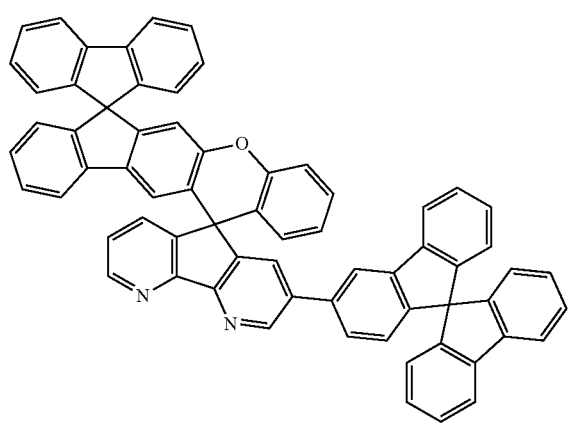
P117
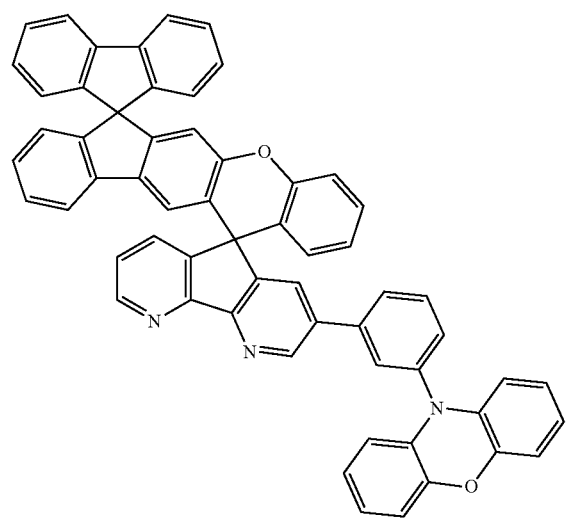
-continued
P118
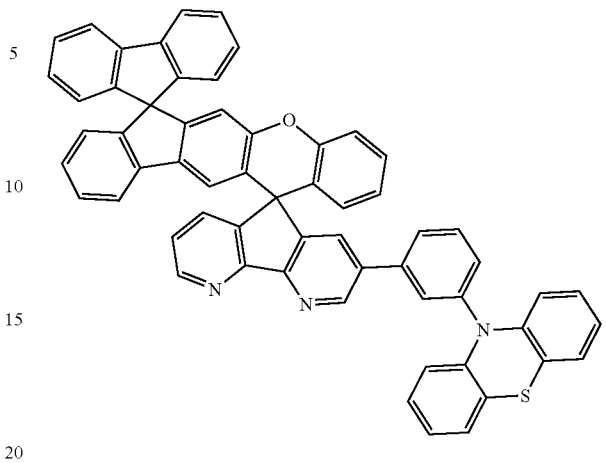
P119
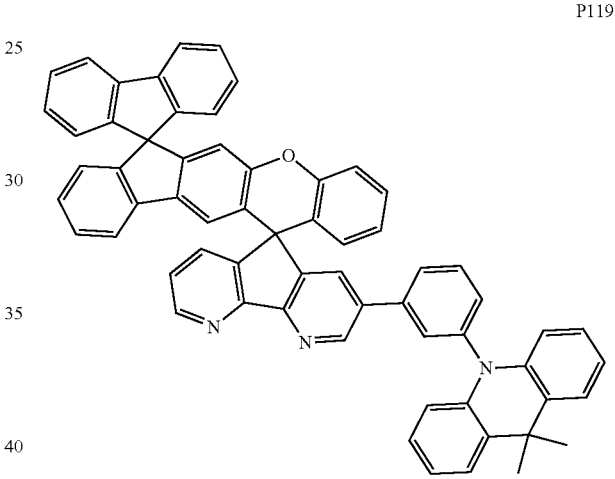
P120
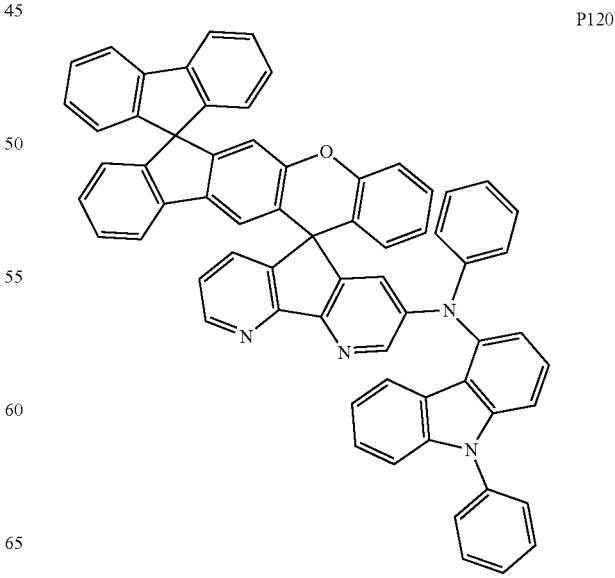

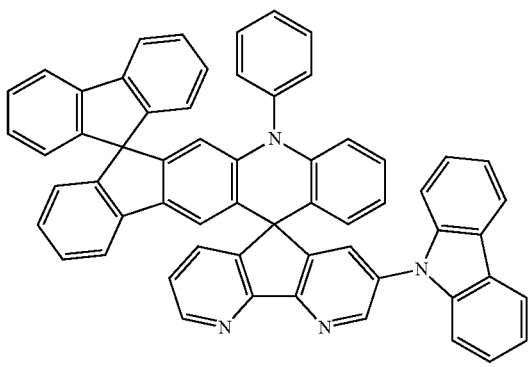
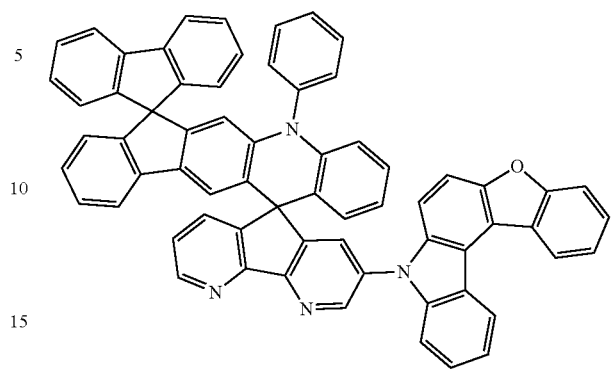
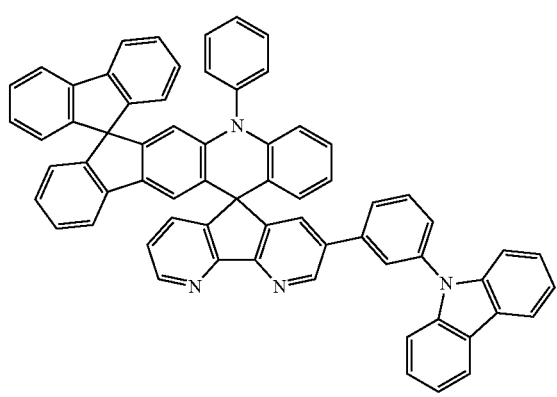

P129
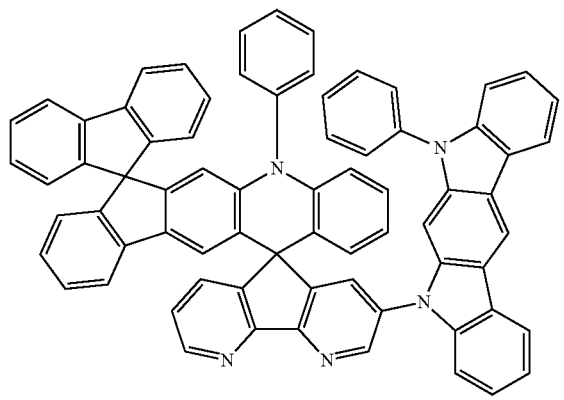
P130
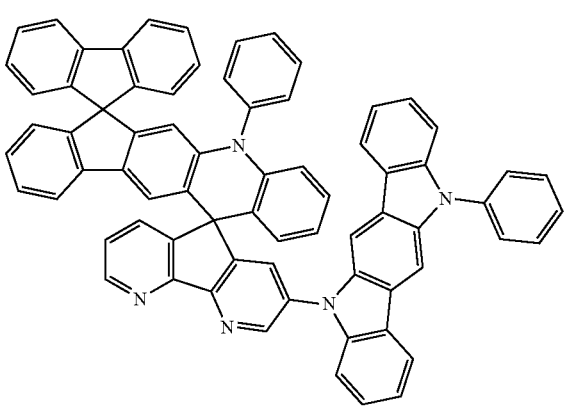
P131
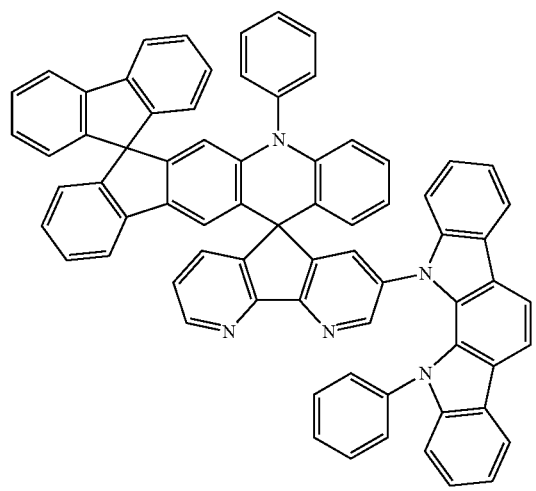
P132
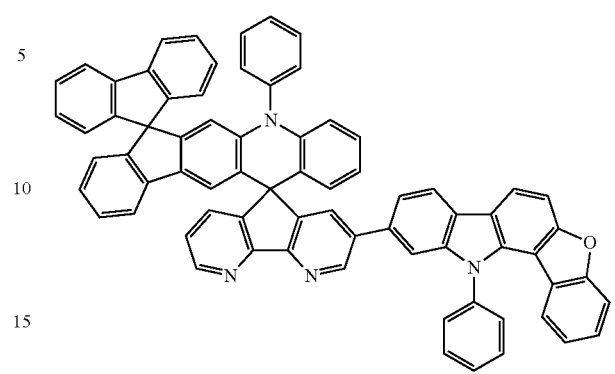
P133
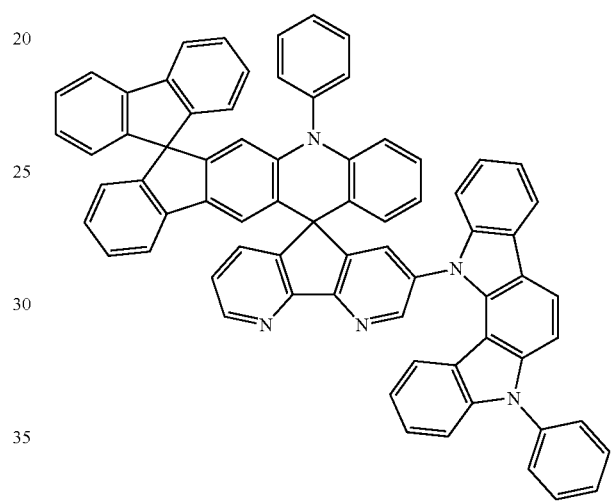
P134
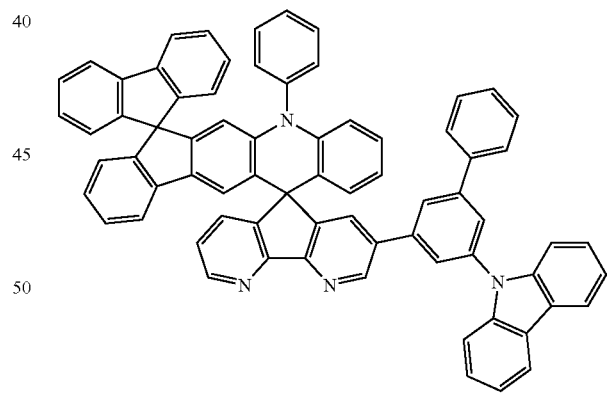
P135
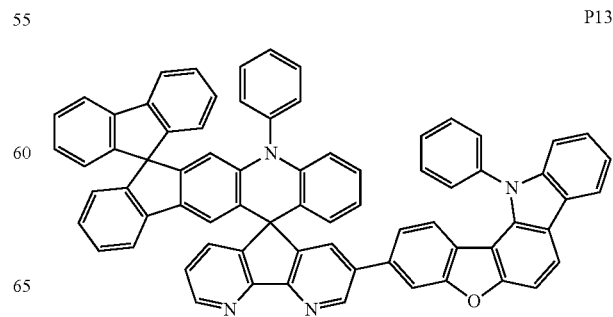

P136
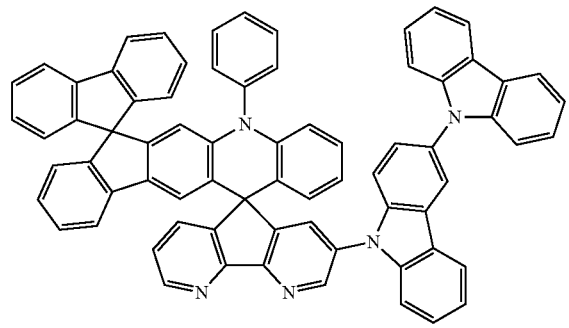
P137
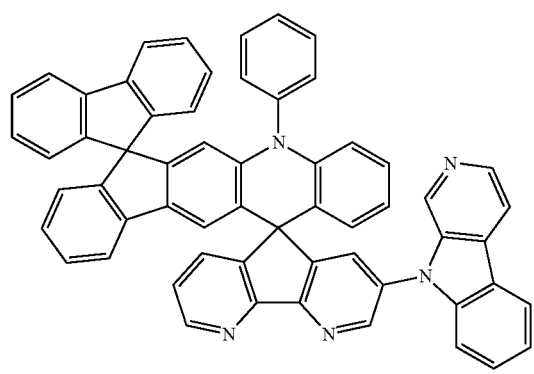
P138
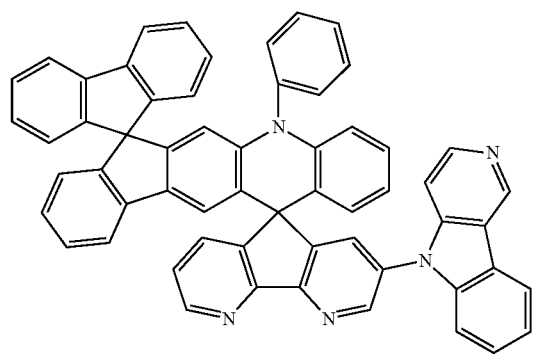
P139
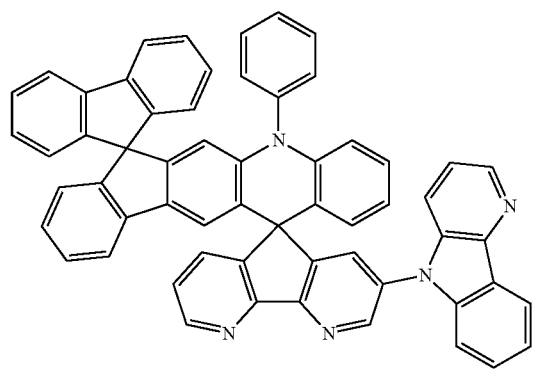
P140
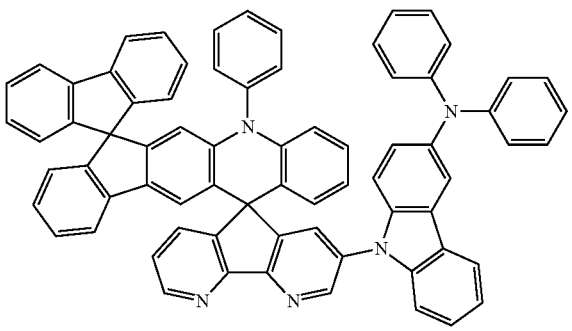
P141
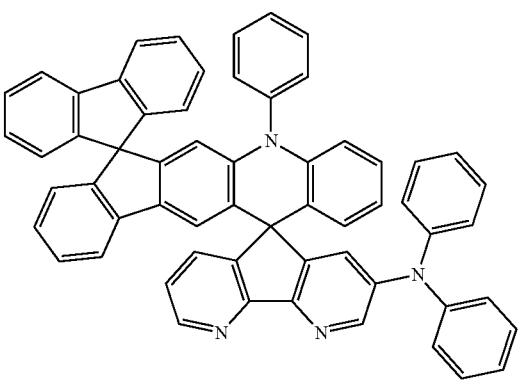
P142
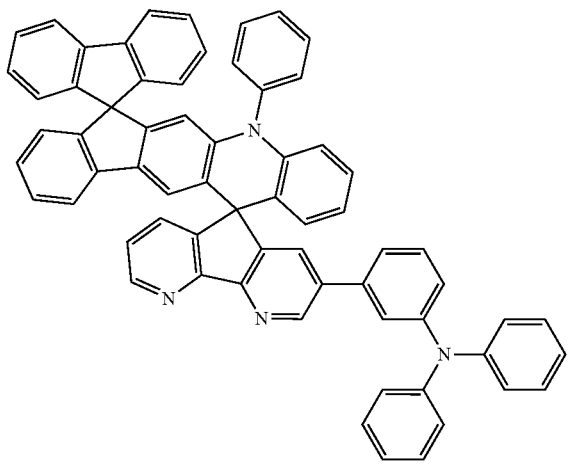
P143
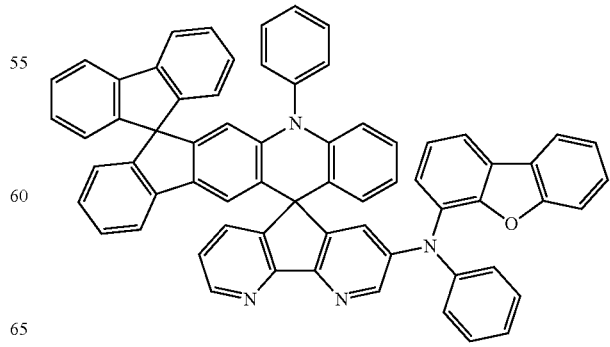

P144
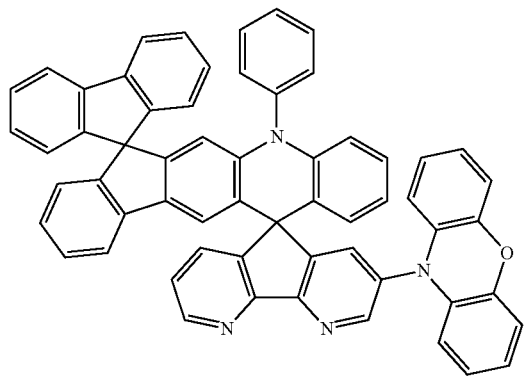
P145
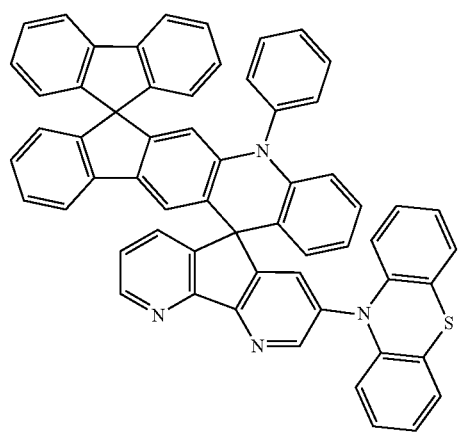
P146
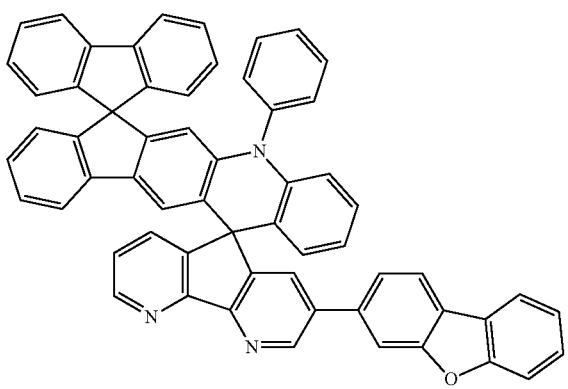
P147
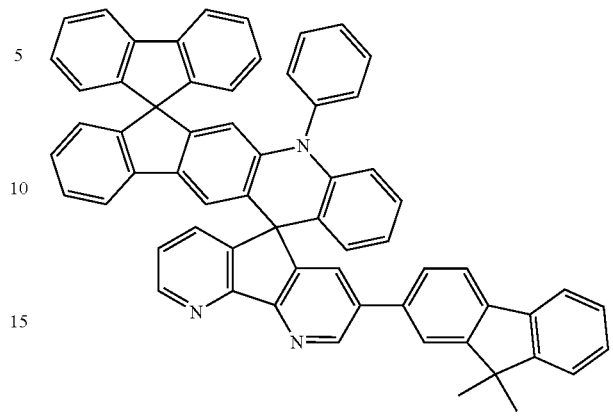
P148
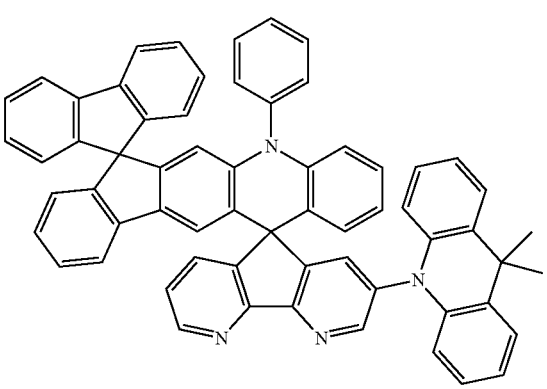
P149
P150
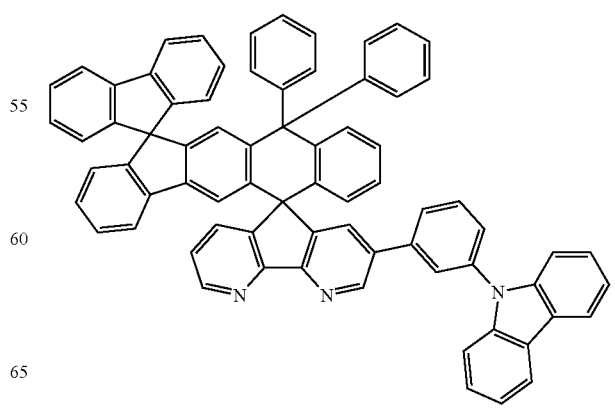

P151
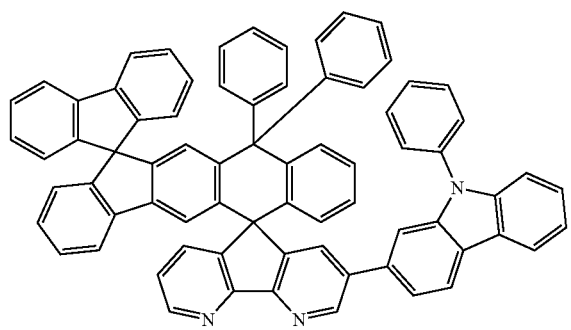
P152
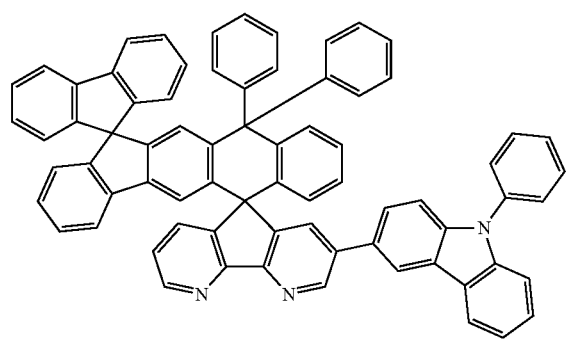
P153
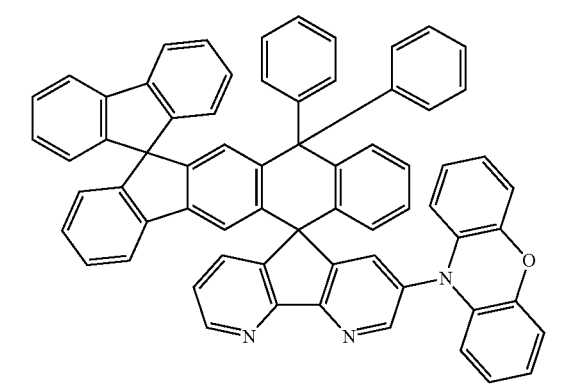
P154
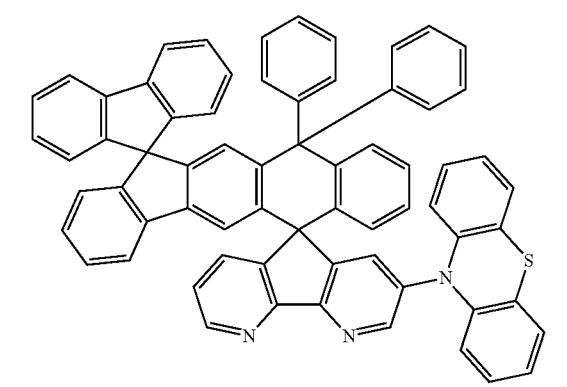
P155
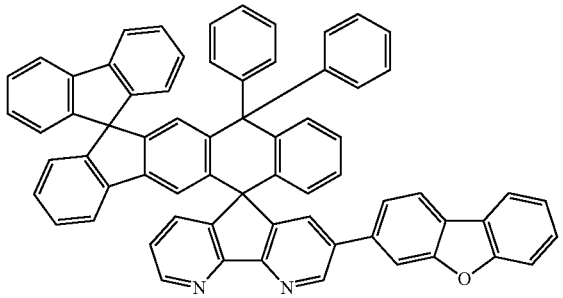
P156
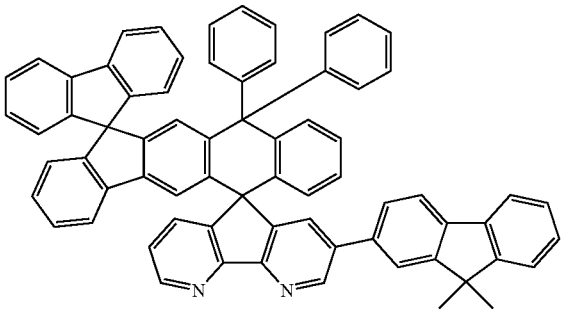
P157
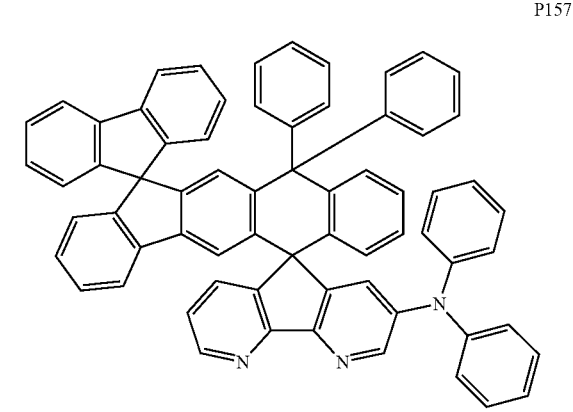
P158
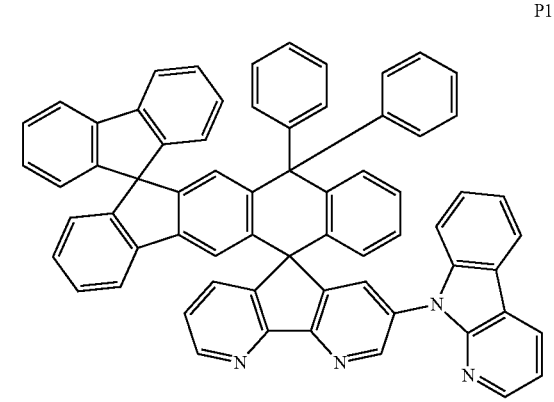

-continued
P159
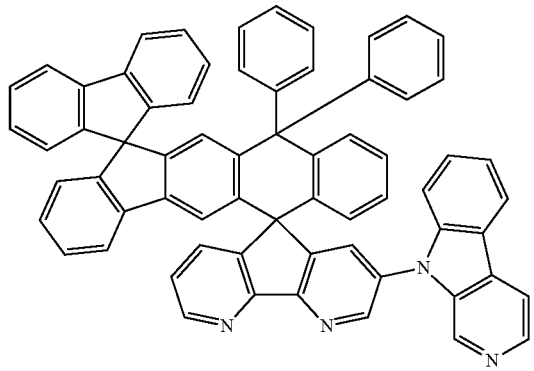
P160
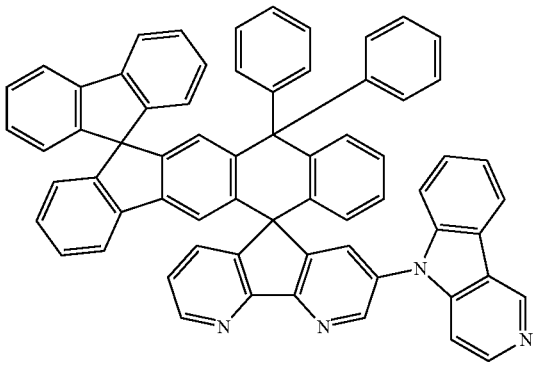
P161
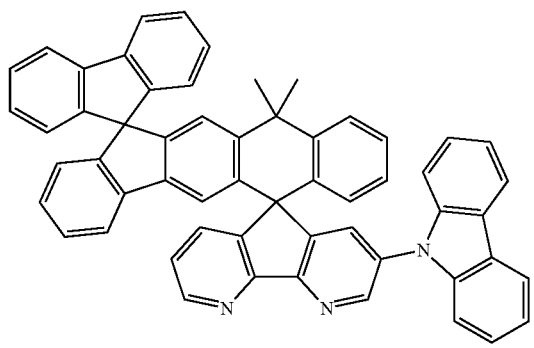
P162
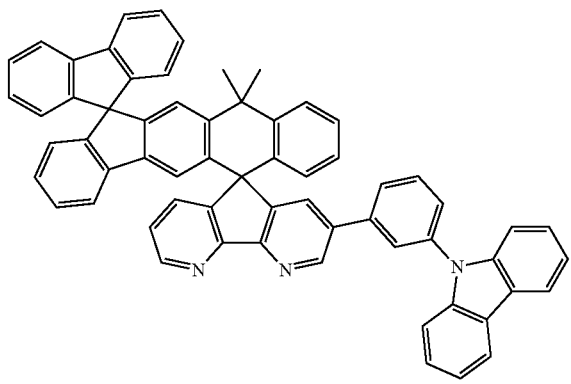
-continued
P163
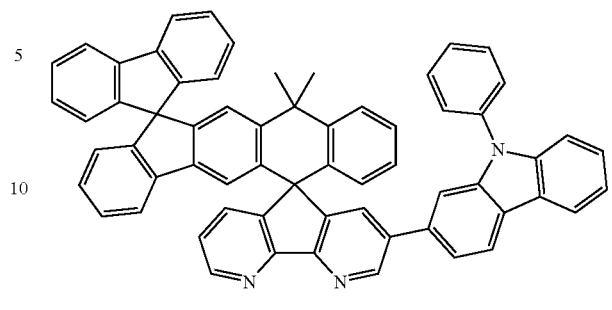
P164
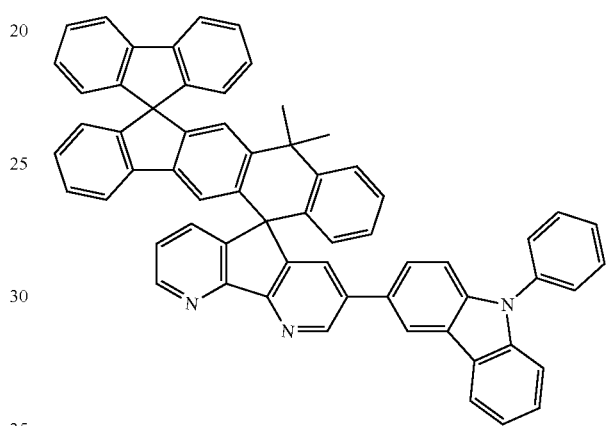
P165
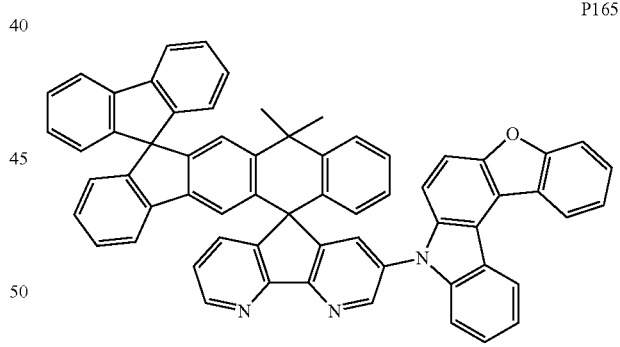
P166
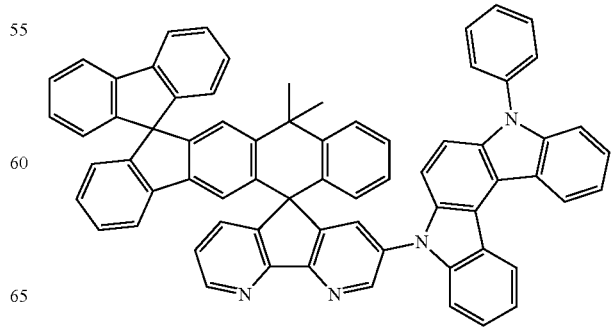

P167
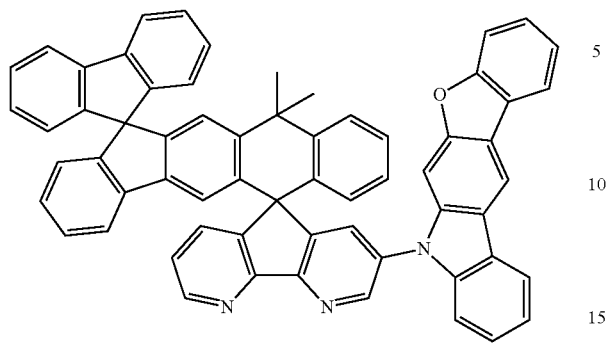
P168
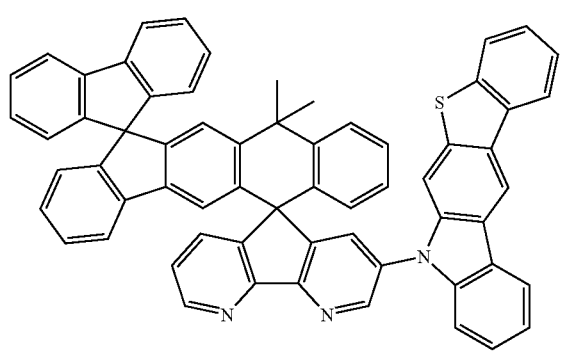
P169
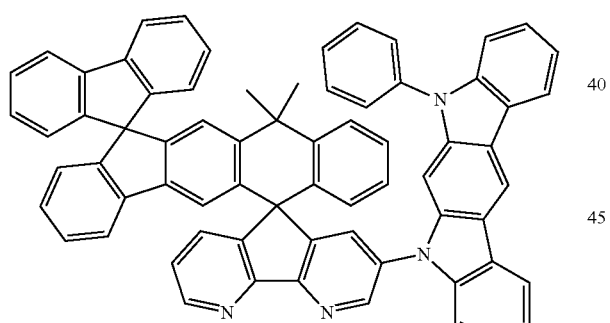
P170
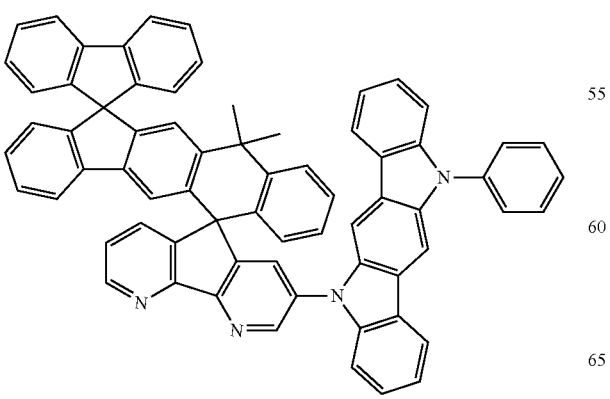
P171
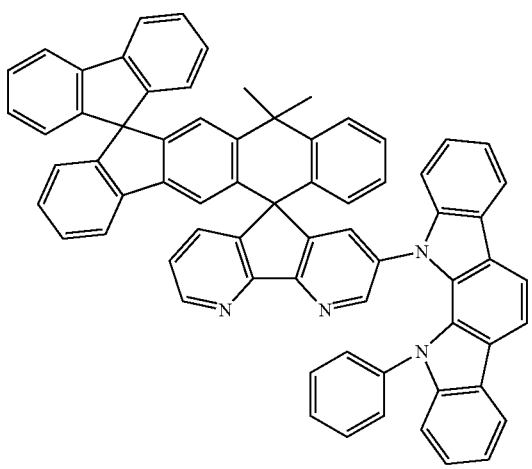
P172
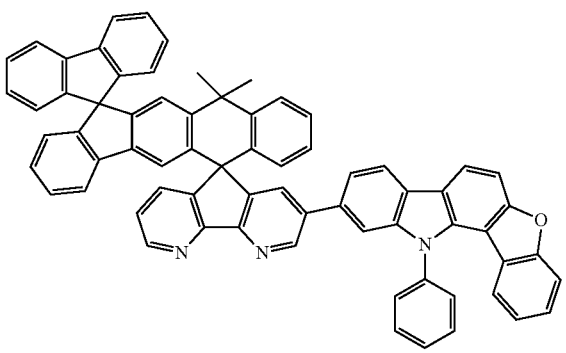
P173
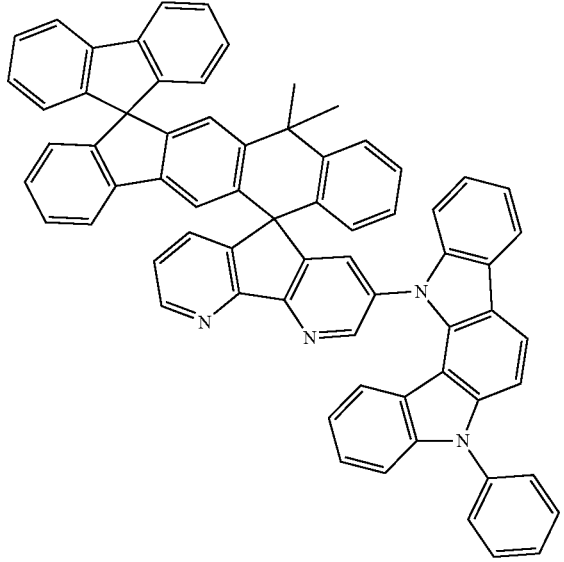

P174
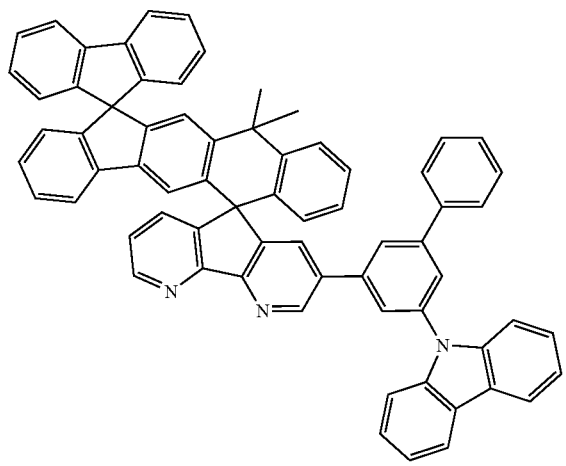
P175
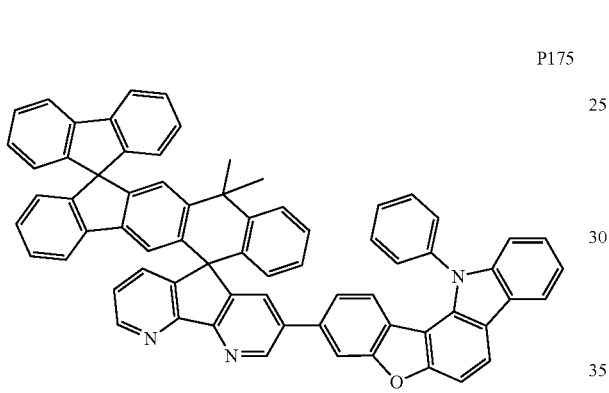
P176
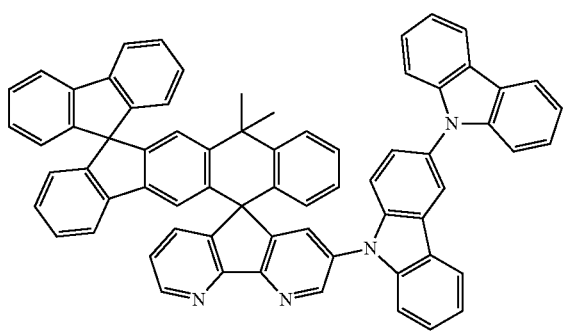
P177
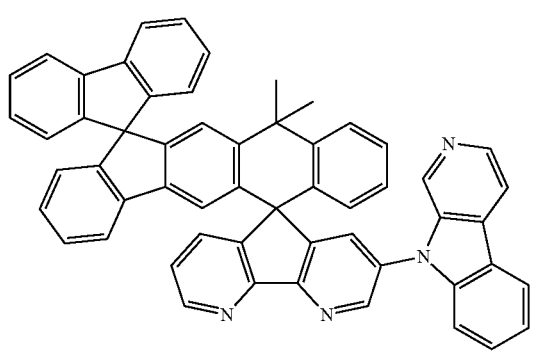
P178
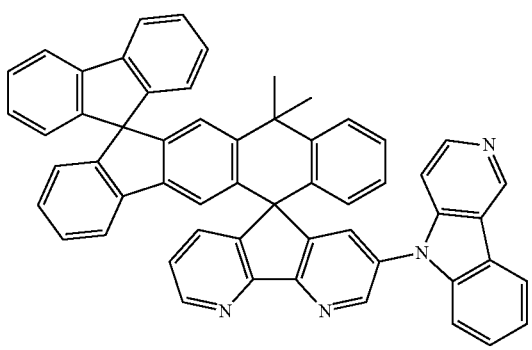
P179
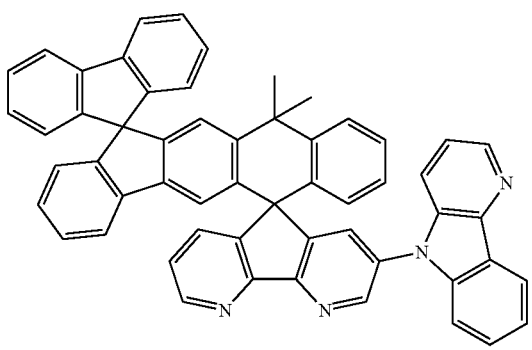
P180
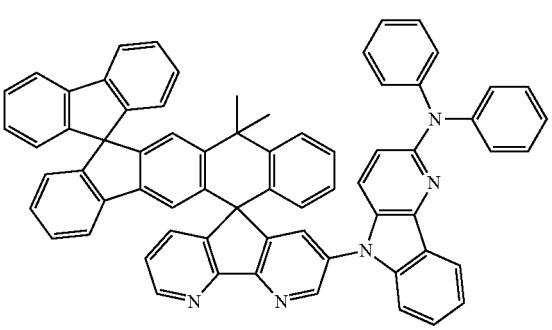
P181
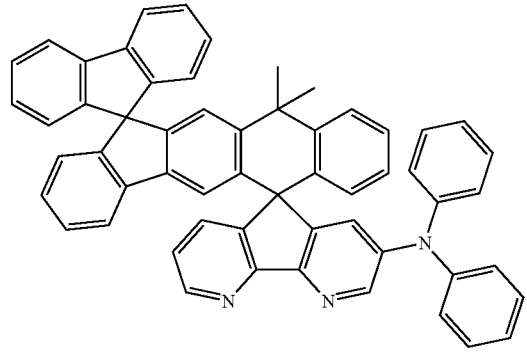

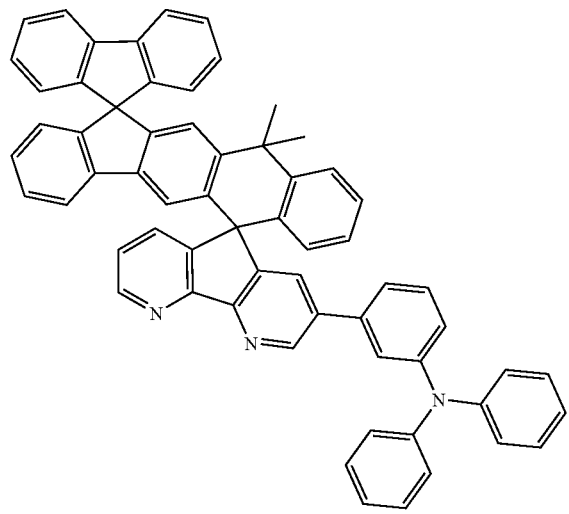
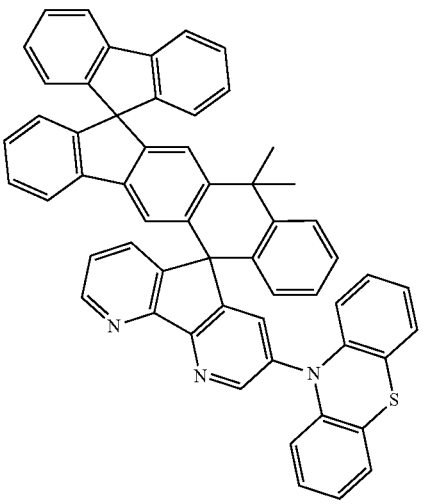
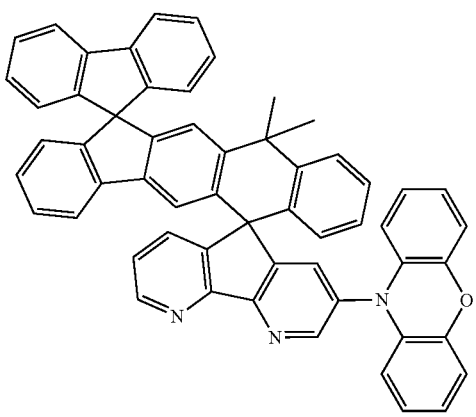

-continued
P189
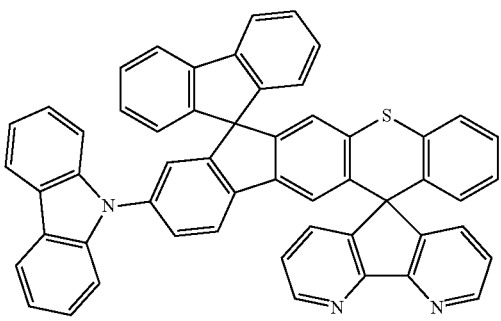
P190
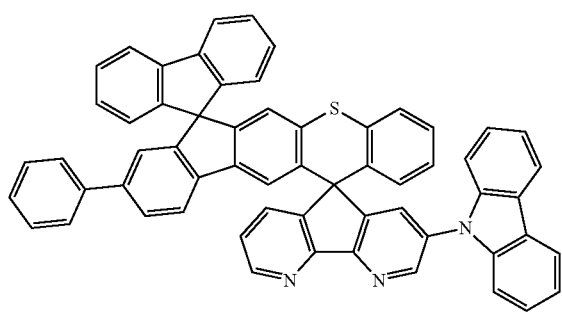
P191
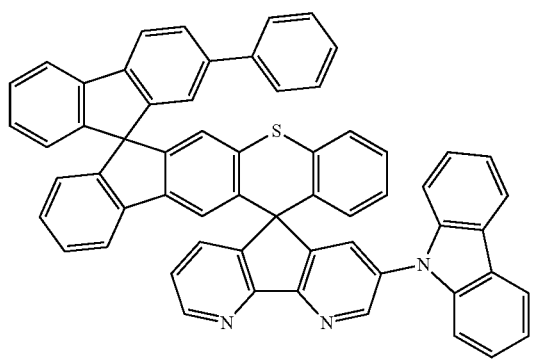
P192
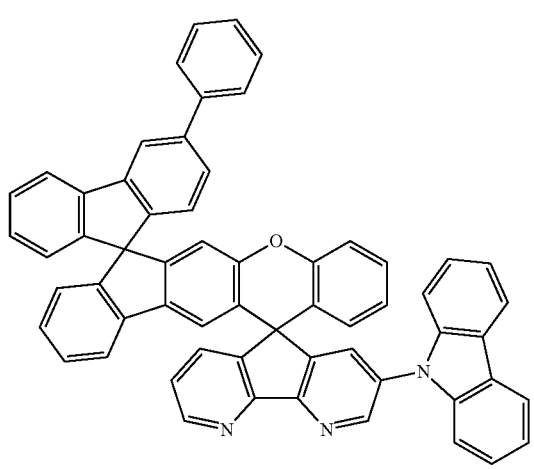
-continued
P193
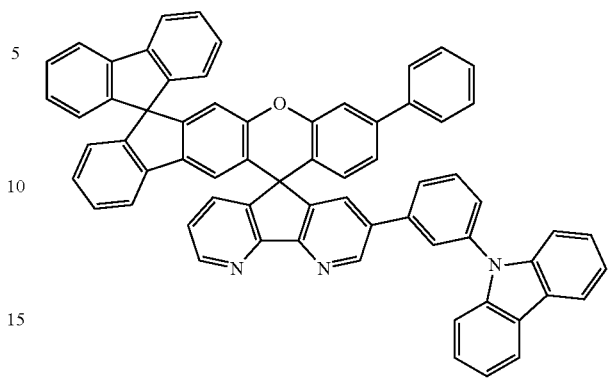
P194
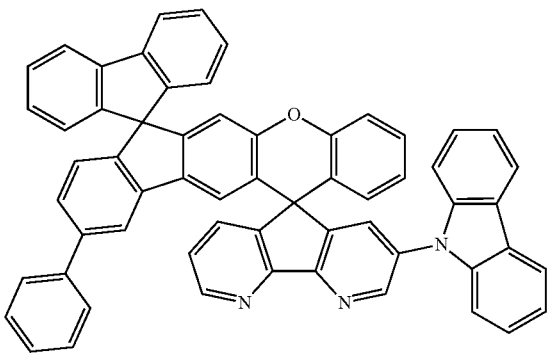
P195
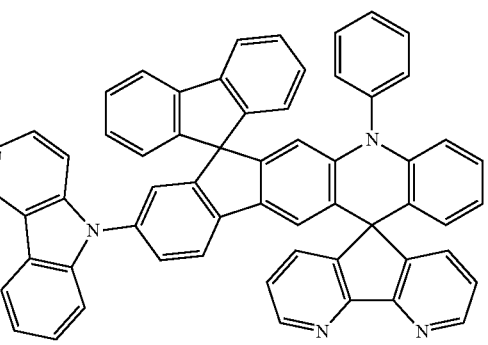
P196
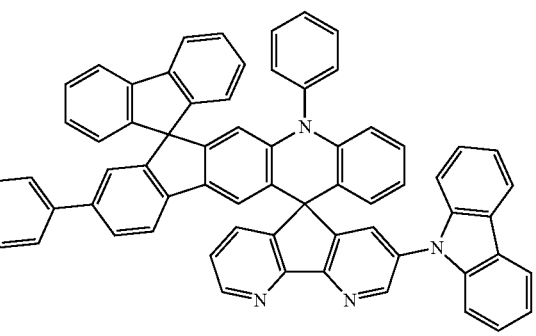

P197
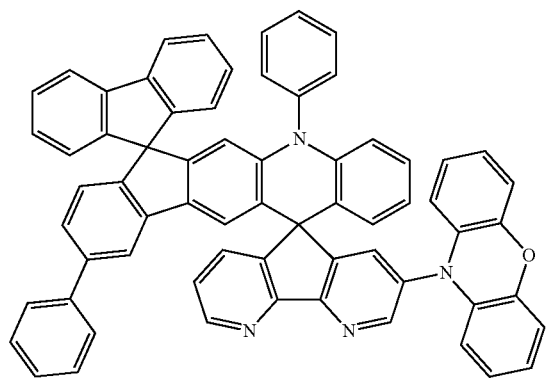
P198
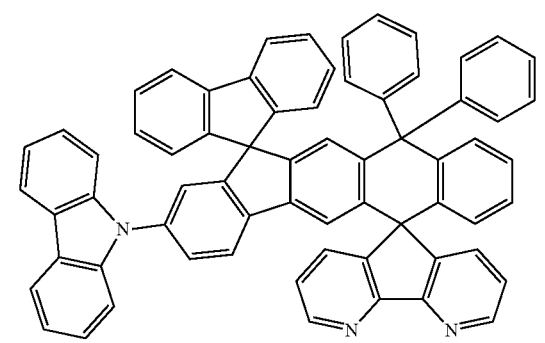
P199
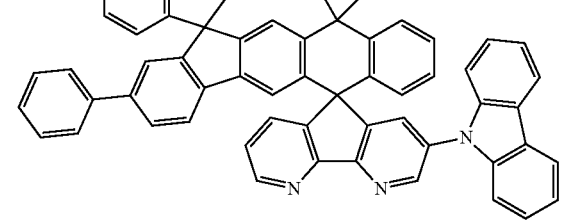
P200
P201
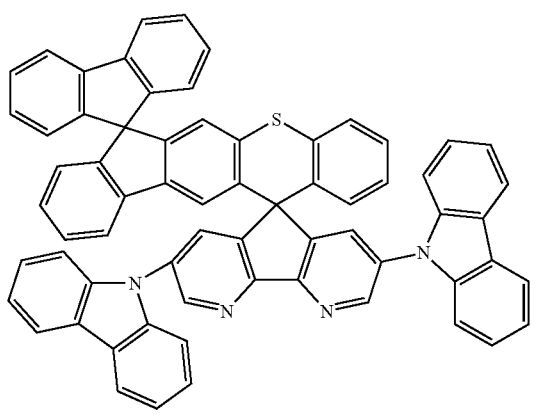
P202
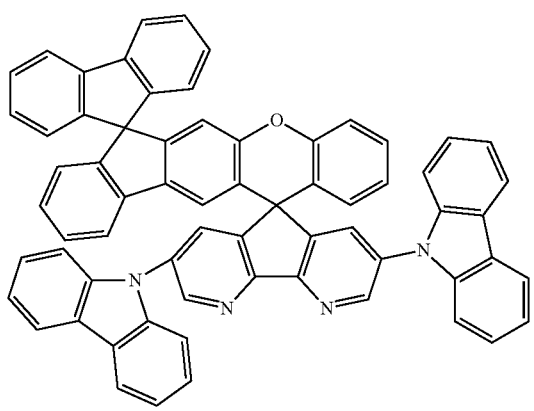
P203
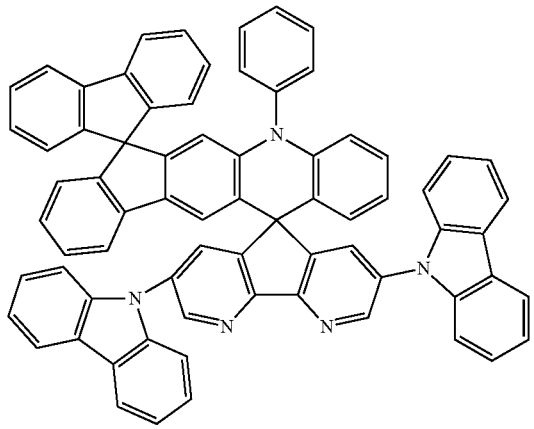

P204
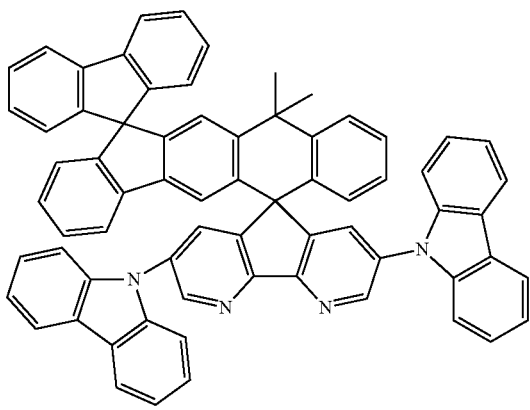
P205
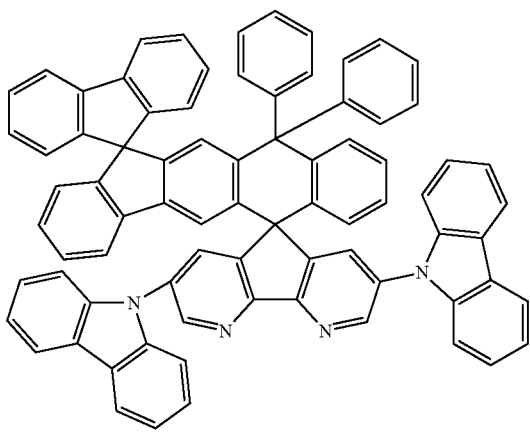
P206
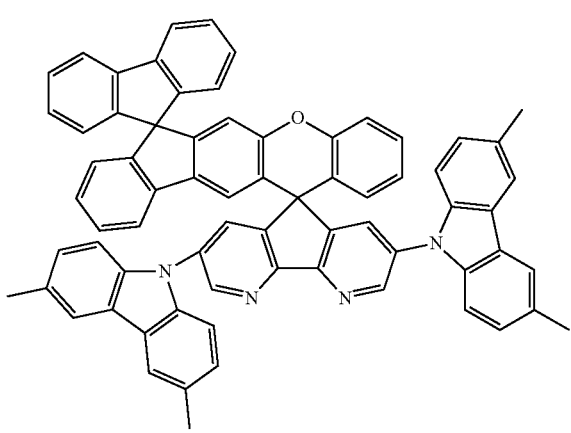
P207
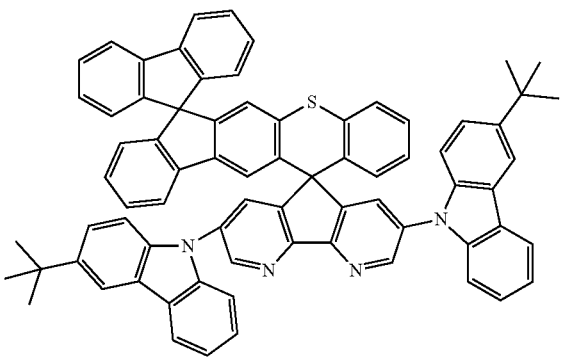
P208
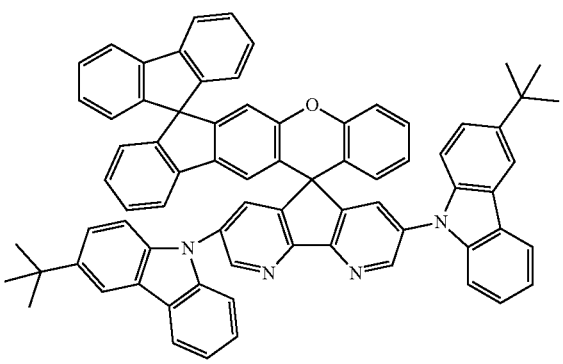
P209
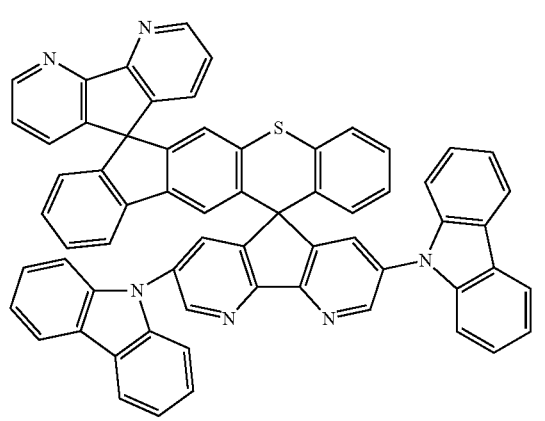
P210

-continued
P211
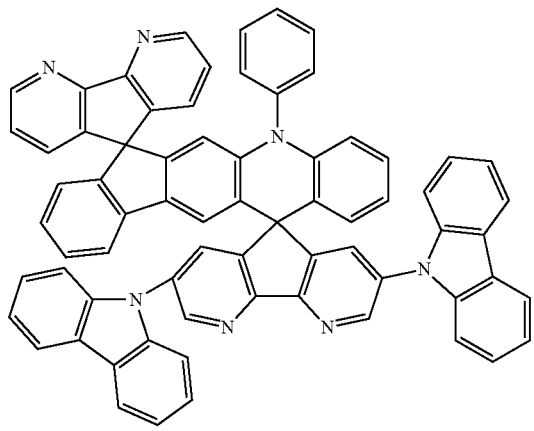
P212
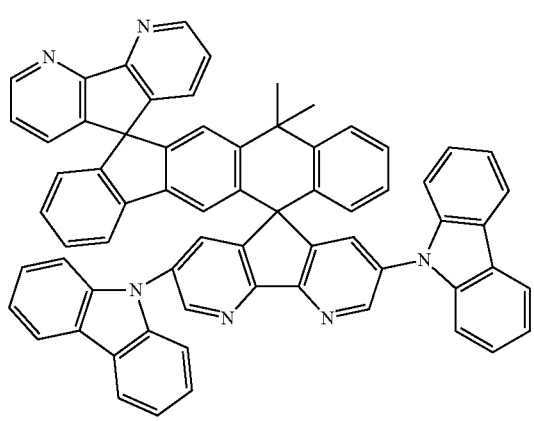
P213
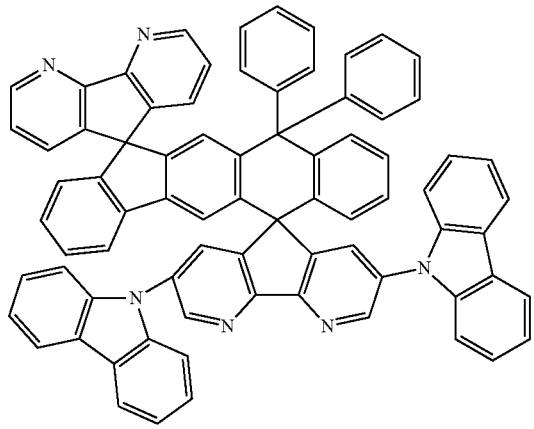
-continued
P214
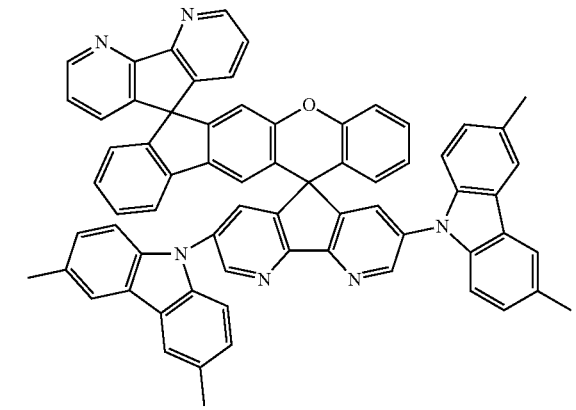
P215
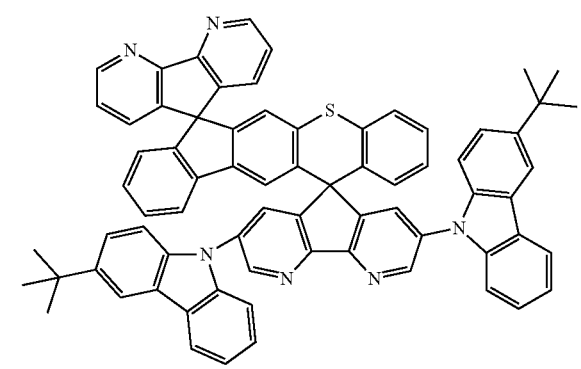
P216
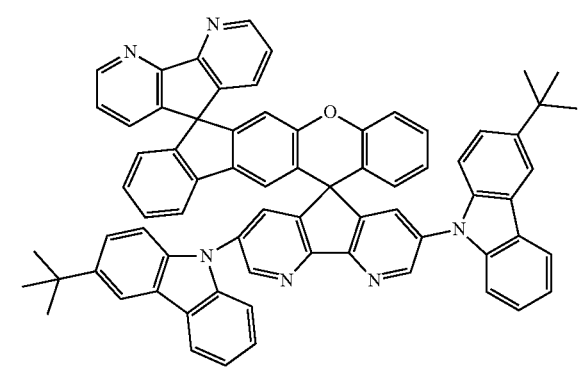
P217
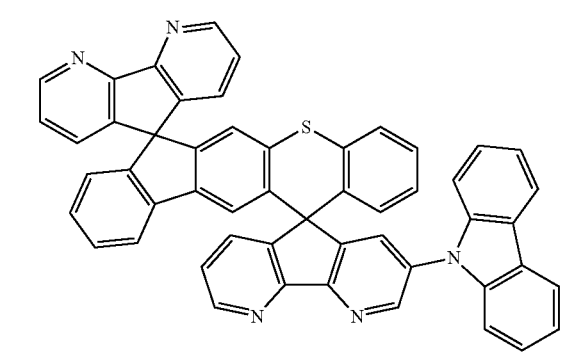

-continued
P218
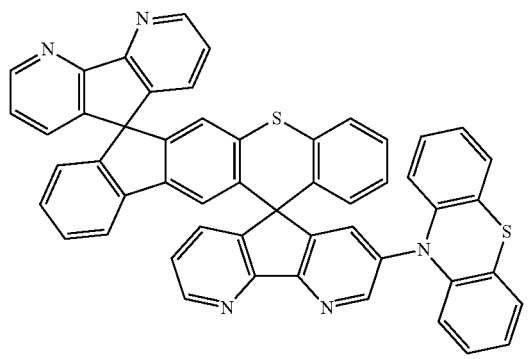
P219
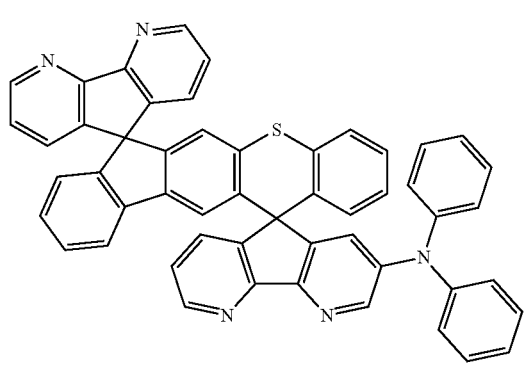
P220
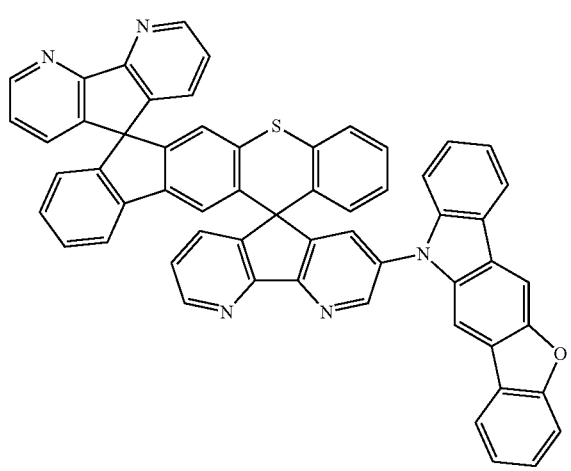
P221
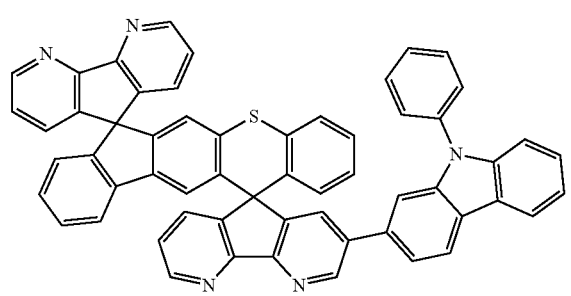
-continued
P222
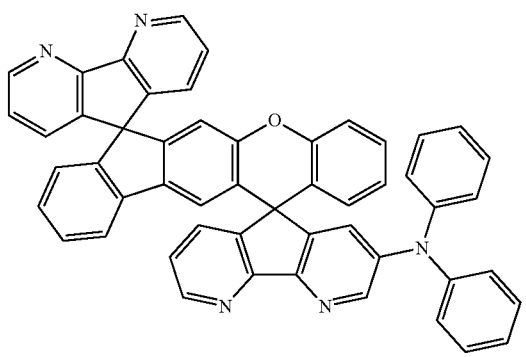
P223
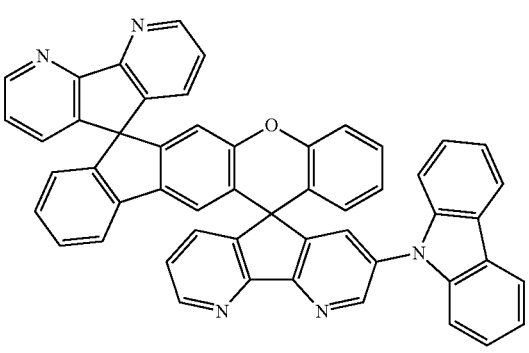
P224
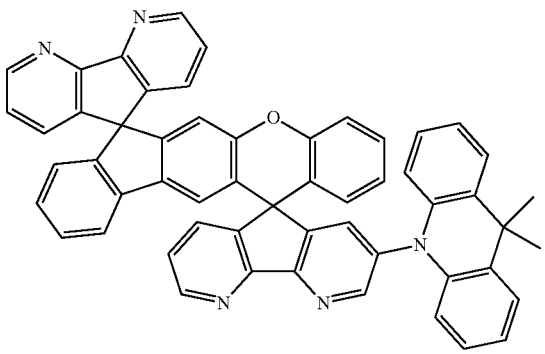
P225
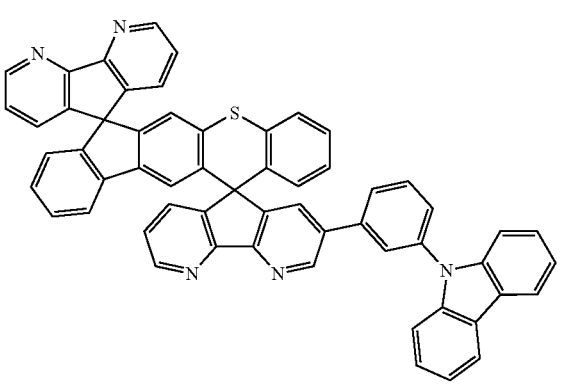

P226
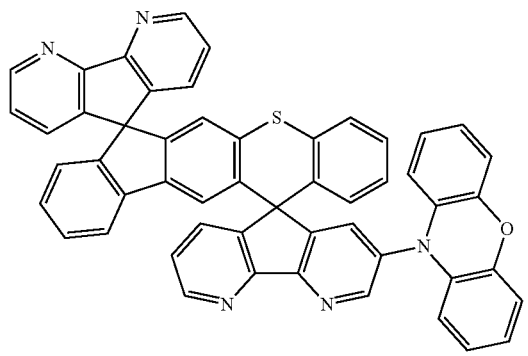
P227
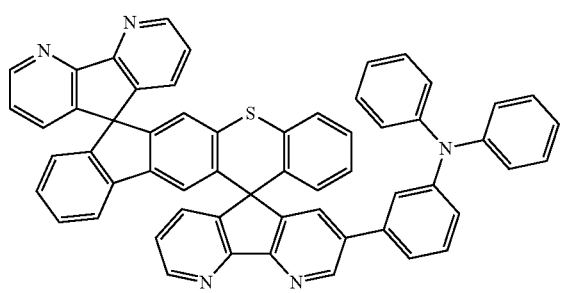
P228
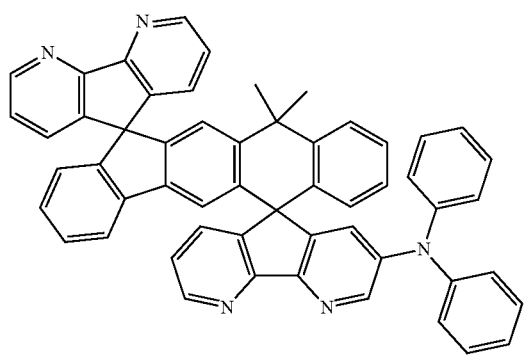
P229
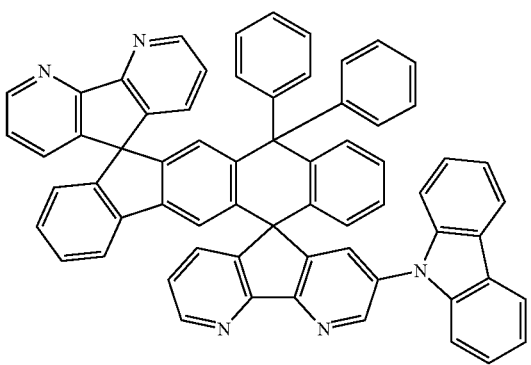
P230
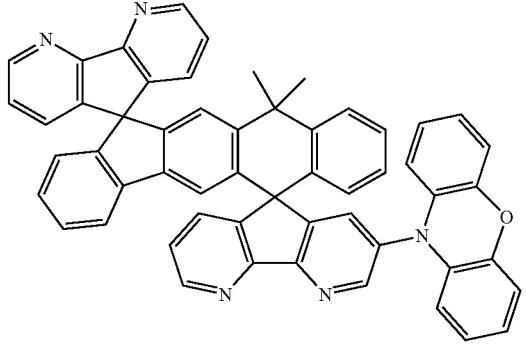
P231
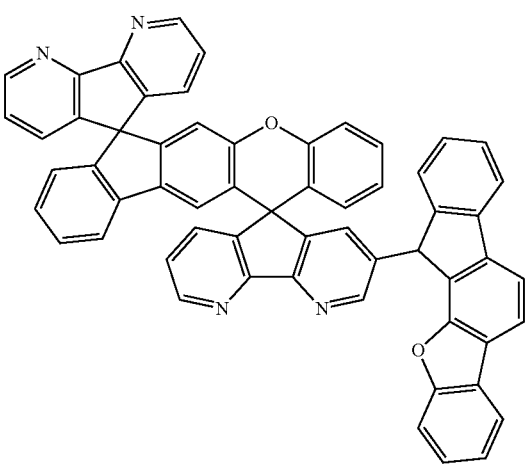
P232
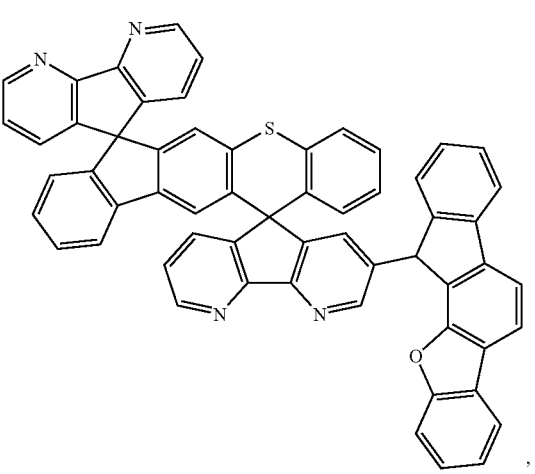
, and -continued

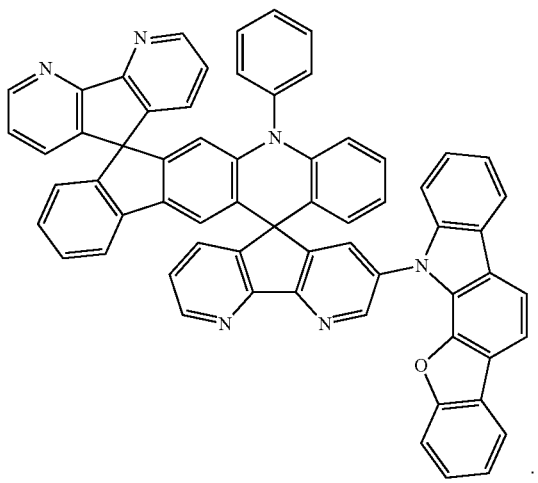

P233

11. An electroluminescent material, comprising the organic compound according to claim 1.

12. A display panel, comprising an OLED device, wherein the OLED device comprises an anode, a cathode, and an organic thin film layer between the anode and the cathode, and a material of the organic thin film layer comprises the electroluminescent material according to claim 11.

13. A display panel, comprising an OLED device, wherein the OLED device comprises an anode, a cathode, and an organic thin film layer between the anode and the cathode, wherein the organic thin film layer comprises a light emitting layer, and the material of the light emitting layer comprises the electroluminescent material according to claim 11.

14. The display panel according to claim 13, wherein the electroluminescent material is used as a phosphorescent host material of the light emitting layer.

15. A display panel, comprising an OLED device, wherein the OLED device comprises an anode, a cathode, and an organic thin film layer between the anode and the cathode, wherein the organic thin film layer comprises a hole blocking layer, and the material of the hole blocking layer comprises the electroluminescent material according to claim 11.

16. A display panel, comprising an OLED device, wherein the OLED device comprises an anode, a cathode, and an organic thin film layer between the anode and the cathode, wherein the organic thin film layer comprises an electron blocking layer, and the material of the electron blocking layer comprises the electroluminescent material according to claim 11.

17. An electronic device, comprising the display panel according to claim 12.

* * * * *